(12) United States Patent
Twardowski et al.

(10) Patent No.: US 9,267,212 B2
(45) Date of Patent: Feb. 23, 2016

(54) METHOD AND SYSTEM FOR PRODUCTION OF OXALIC ACID AND OXALIC ACID REDUCTION PRODUCTS

(71) Applicant: Liquid Light, Inc., Monmouth Junction, NJ (US)

(72) Inventors: Zbigniew Twardowski, Burnaby (CA); Emily Barton Cole, Houston, TX (US); Jerry J. Kaczur, North Miami Beach, FL (US); Kyle Teamey, Washington, DC (US); Kate A. Keets, Lawrenceville, NJ (US); Rishi Parajuli, Kendell Park, NJ (US); Alexander Bauer, Monmouth Junction, NJ (US); Narayanappa Sivasankar, Plainsboro, NJ (US); George Leonard, Princeton, NJ (US); Theodore J. Kramer, New York, NY (US); Paul Majsztrik, Cranbury, NJ (US); Yizu Zhu, North Andover, MA (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

(21) Appl. No.: 14/220,840

(22) Filed: Mar. 20, 2014

(65) Prior Publication Data
US 2014/0206895 A1 Jul. 24, 2014

Related U.S. Application Data

(63) Continuation of application No. PCT/US2013/077610, filed on Dec. 23, 2013, which is a continuation-in-part of application No. 13/724,996, filed on Dec. 21, 2012, now Pat. No. 8,691,069.

(Continued)

(51) Int. Cl.
*C07C 67/08* (2006.01)
*C07C 55/06* (2006.01)

(Continued)

(52) U.S. Cl.
CPC ............... *C25B 3/04* (2013.01); *C07C 29/149* (2013.01); *C07C 51/347* (2013.01); *C07C 67/08* (2013.01); *C25B 9/08* (2013.01)

(58) Field of Classification Search
CPC .... C07C 29/149; C07C 67/08; C07C 31/202; C07C 69/36; C07C 51/347; C07C 51/367; C25B 3/04; C25B 9/08
USPC ........... 560/204; 205/440; 204/265; 562/579; 568/864
See application file for complete search history.

(56) References Cited

U.S. PATENT DOCUMENTS 1,962,140 A * 6/1934 Dreyfus .................. 562/579
3,019,256 A 1/1962 Dunn (Continued)

FOREIGN PATENT DOCUMENTS

| | | |
|---|---|---|
| CN | 102190573 A | 9/2011 |
| DE | 1047765 A | 12/1958 |

(Continued)

OTHER PUBLICATIONS

Seshadri et al, "A new homogeneous catalyst for the reduction of carbon dioxide to methanol at low overpotential," Journal of Electroanalytical Chemistry, 372 (1994) 145-150.

(Continued)

*Primary Examiner* — Karl J Puttlitz
*Assistant Examiner* — Amy C Bonaparte
(74) *Attorney, Agent, or Firm* — Suiter Swantz pc llo

(57) ABSTRACT

The present disclosure is a method and system for production of oxalic acid and oxalic acid reduction products. The production of oxalic acid and oxalic acid reduction products may include the electrochemical conversion of $CO_2$ to oxalate and oxalic acid. The method and system for production of oxalic acid and oxalic acid reduction products may further include the acidification of oxalate to oxalic acid, the purification of oxalic acid and the hydrogenation of oxalic acid to produce oxalic acid reduction products.

12 Claims, 30 Drawing Sheets

Related U.S. Application Data

(60) Provisional application No. 61/745,204, filed on Dec. 21, 2012, provisional application No. 61/794,230, filed on Mar. 15, 2013, provisional application No. 61/816,531, filed on Apr. 26, 2013, provisional application No. 61/844,755, filed on Jul. 10, 2013, provisional application No. 61/846,944, filed on Jul. 16, 2013, provisional application No. 61/720,670, filed on Oct. 31, 2012, provisional application No. 61/703,232, filed on Sep. 19, 2012, provisional application No. 61/675,938, filed on Jul. 26, 2012.

(51) Int. Cl.
*C25B 3/04* (2006.01)
*C25B 9/08* (2006.01)
*C07C 29/149* (2006.01)
*C07C 51/347* (2006.01)

(56) References Cited

U.S. PATENT DOCUMENTS

| | | | |
|---|---|---|---|
| 3,088,990 | A | 5/1963 | Rightmire et al. |
| 3,236,879 | A | 2/1966 | Chiusoli |
| 3,293,292 | A | 12/1966 | Olivier et al. |
| 3,326,998 | A | 6/1967 | Reusser et al. |
| 3,341,615 | A | 9/1967 | Wulf et al. |
| 3,341,616 | A | 9/1967 | Vives |
| 3,344,046 | A | 9/1967 | Neikam |
| 3,347,758 | A | 10/1967 | Koehl, Jr. |
| 3,352,935 | A | 11/1967 | Mahan |
| 3,361,653 | A | 1/1968 | Miller |
| 3,401,100 | A | 9/1968 | Macklin |
| 3,492,209 | A | 1/1970 | Miller |
| 3,531,386 | A | 9/1970 | Heredy |
| 3,560,354 | A | 2/1971 | Young |
| 3,607,962 | A | 9/1971 | Krekeler et al. |
| 3,636,159 | A | 1/1972 | Solomon |
| 3,720,591 | A | 3/1973 | Skarlos |
| 3,745,180 | A | 7/1973 | Rennie |
| 3,764,492 | A | 10/1973 | Baizer et al. |
| 3,779,875 | A | 12/1973 | Michelet |
| 3,824,163 | A | 7/1974 | Maget |
| 4,072,583 | A | 2/1978 | Hallcher et al. |
| 4,087,470 | A | 5/1978 | Suzuki |
| 4,088,682 | A | 5/1978 | Jordan |
| 4,147,599 | A | 4/1979 | O'Leary et al. |
| 4,162,948 | A | 7/1979 | Yagii et al. |
| 4,219,392 | A | 8/1980 | Halmann |
| 4,245,114 | A | 1/1981 | Peltzman |
| 4,256,550 | A | 3/1981 | Niinobe et al. |
| 4,267,070 | A | 5/1981 | Nefedov et al. |
| 4,343,690 | A | 8/1982 | De Nora |
| 4,381,978 | A | 5/1983 | Gratzel et al. |
| 4,421,613 | A | 12/1983 | Goodridge et al. |
| 4,450,055 | A | 5/1984 | Stafford |
| 4,476,003 | A | 10/1984 | Frank et al. |
| 4,523,981 | A | 6/1985 | Ang et al. |
| 4,545,886 | A | 10/1985 | De Nora et al. |
| 4,547,271 | A | 10/1985 | Bharucha et al. |
| 4,563,254 | A | 1/1986 | Morduchowitz et al. |
| 4,595,465 | A | 6/1986 | Ang et al. |
| 4,608,132 | A | 8/1986 | Sammells |
| 4,608,133 | A | 8/1986 | Morduchowitz et al. |
| 4,619,743 | A | 10/1986 | Cook |
| 4,661,422 | A | 4/1987 | Marianowski et al. |
| 4,673,473 | A | 6/1987 | Ang et al. |
| 4,702,973 | A | 10/1987 | Marianowski |
| 4,732,655 | A | 3/1988 | Morduchowitz et al. |
| 4,810,596 | A | 3/1989 | Ludwig |
| 4,902,828 | A | 2/1990 | Wickenhaeuser et al. |
| 4,950,368 | A | 8/1990 | Weinberg et al. |
| 4,968,393 | A | 11/1990 | Mazur et al. |
| 5,074,974 | A | 12/1991 | Toomey, Jr. |
| 5,084,148 | A | 1/1992 | Kazcur et al. |
| 5,106,465 | A | 4/1992 | Kaczur et al. |
| 5,107,040 | A | 4/1992 | Repman et al. |
| 5,155,256 | A | 10/1992 | Chapman |
| 5,198,086 | A | 3/1993 | Chlanda et al. |
| 5,246,551 | A | 9/1993 | Pletcher et al. |
| 5,290,404 | A | 3/1994 | Toomey |
| 5,294,319 | A | 3/1994 | Kaczur et al. |
| 5,300,369 | A | 4/1994 | Dietrich et al. |
| 5,412,150 | A | 5/1995 | Wessel |
| 5,443,804 | A | 8/1995 | Parker et al. |
| 5,455,372 | A * | 10/1995 | Hirai et al. .................... 560/179 |
| 5,474,658 | A | 12/1995 | Scharbert et al. |
| 5,514,492 | A | 5/1996 | Marincic et al. |
| 5,536,856 | A | 7/1996 | Harrison et al. |
| 5,654,493 | A | 8/1997 | Wessel |
| 5,804,045 | A | 9/1998 | Orillon et al. |
| 5,961,813 | A | 10/1999 | Gestermann et al. |
| 6,001,500 | A | 12/1999 | Bass et al. |
| 6,024,935 | A | 2/2000 | Mills et al. |
| 6,251,256 | B1 | 6/2001 | Blay et al. |
| 6,312,655 | B1 | 11/2001 | Hesse et al. |
| 6,380,446 | B1 | 4/2002 | Drew et al. |
| 6,465,699 | B1 | 10/2002 | Grosso |
| 6,492,047 | B1 | 12/2002 | Peled et al. |
| 6,777,571 | B2 | 8/2004 | Chaturvedi et al. |
| 6,881,320 | B1 | 4/2005 | Krafton et al. |
| 7,138,201 | B2 | 11/2006 | Inoue et al. |
| 7,462,752 | B2 | 12/2008 | Fong et al. |
| 7,883,610 | B2 | 2/2011 | Monzyk et al. |
| 8,277,631 | B2 | 10/2012 | Eastman et al. |
| 8,313,634 | B2 | 11/2012 | Bocarsly et al. |
| 8,444,844 | B1 | 5/2013 | Teamey et al. |
| 8,663,447 | B2 | 3/2014 | Bocarsly et al. |
| 2001/0001798 | A1 | 5/2001 | Sharpless et al. |
| 2001/0026884 | A1 | 10/2001 | Appleby et al. |
| 2002/0022753 | A1 | 2/2002 | Drew et al. |
| 2002/0122980 | A1 | 9/2002 | Fleischer et al. |
| 2004/0115489 | A1 | 6/2004 | Goel |
| 2005/0245784 | A1 | 11/2005 | Carson et al. |
| 2006/0102468 | A1 | 5/2006 | Monzyk et al. |
| 2006/0269813 | A1 | 11/2006 | Seabaugh et al. |
| 2007/0004023 | A1 | 1/2007 | Trachtenberg |
| 2007/0012577 | A1 | 1/2007 | Bulan et al. |
| 2007/0224479 | A1 | 9/2007 | Tadokoro et al. |
| 2008/0223727 | A1 | 9/2008 | Oloman et al. |
| 2008/0248350 | A1 | 10/2008 | Little et al. |
| 2008/0283411 | A1 | 11/2008 | Eastman et al. |
| 2008/0286643 | A1 | 11/2008 | Iwasaki |
| 2008/0296146 | A1 | 12/2008 | Toulhoat et al. |
| 2008/0314758 | A1 | 12/2008 | Grosso et al. |
| 2009/0014336 | A1 | 1/2009 | Olah et al. |
| 2009/0030240 | A1 | 1/2009 | Olah et al. |
| 2009/0057161 | A1 | 3/2009 | Aulich et al. |
| 2009/0156867 | A1 | 6/2009 | Van Kruchten |
| 2010/0061922 | A1 | 3/2010 | Rauser et al. |
| 2010/0069600 | A1 | 3/2010 | Morelle et al. |
| 2010/0130768 | A1 | 5/2010 | Sato et al. |
| 2010/0187123 | A1 | 7/2010 | Bocarsly et al. |
| 2010/0187125 | A1 | 7/2010 | Sandoval et al. |
| 2010/0191024 | A1 | 7/2010 | Uenveren et al. |
| 2010/0196800 | A1 | 8/2010 | Markoski et al. |
| 2010/0248042 | A1 | 9/2010 | Nakagawa et al. |
| 2010/0270167 | A1 | 10/2010 | McFarland |
| 2010/0282614 | A1 | 11/2010 | Detournay et al. |
| 2010/0305629 | A1 | 12/2010 | Lund et al. |
| 2010/0330435 | A1 | 12/2010 | Nemeth et al. |
| 2011/0024288 | A1 | 2/2011 | Bhavaraju et al. |
| 2011/0083968 | A1 | 4/2011 | Gilliam et al. |
| 2011/0114501 | A1 | 5/2011 | Teamey et al. |
| 2011/0114502 | A1 | 5/2011 | Cole et al. |
| 2011/0114503 | A1 | 5/2011 | Sivasankar et al. |
| 2011/0114504 | A1 | 5/2011 | Sivasankar et al. |
| 2011/0143929 | A1 | 6/2011 | Sato et al. |
| 2011/0177398 | A1 | 7/2011 | Affinito et al. |
| 2011/0186441 | A1 | 8/2011 | LaFrancois et al. |
| 2011/0217226 | A1 | 9/2011 | Mosa et al. |
| 2011/0226632 | A1 | 9/2011 | Cole et al. |
| 2011/0237830 | A1 | 9/2011 | Masel |
| 2011/0303551 | A1 | 12/2011 | Gilliam et al. |

(56) References Cited

U.S. PATENT DOCUMENTS

| | | | |
|---|---|---|---|
| 2011/0318617 | A1 | 12/2011 | Kirchev et al. |
| 2012/0004448 | A1 | 1/2012 | Bhattacharyya et al. |
| 2012/0004449 | A1 | 1/2012 | Bhattacharyya et al. |
| 2012/0004454 | A1 | 1/2012 | Bhattacharyya et al. |
| 2012/0018311 | A1 | 1/2012 | Yotsuhashi et al. |
| 2012/0043301 | A1 | 2/2012 | Arvin et al. |
| 2012/0132537 | A1 | 5/2012 | Sivasankar et al. |
| 2012/0199493 | A1 | 8/2012 | Krafft et al. |
| 2012/0215034 | A1 | 8/2012 | McFarland |
| 2012/0228147 | A1 | 9/2012 | Sivasankar et al. |
| 2012/0277465 | A1 | 11/2012 | Cole et al. |
| 2012/0292196 | A1 | 11/2012 | Albrecht et al. |
| 2012/0295172 | A1 | 11/2012 | Peled et al. |
| 2012/0298522 | A1 | 11/2012 | Shipchandler et al. |
| 2012/0329657 | A1 | 12/2012 | Eastman et al. |
| 2013/0062216 | A1 | 3/2013 | Yotsuhashi et al. |
| 2013/0098772 | A1 | 4/2013 | Bocarsly et al. |
| 2013/0105304 | A1 | 5/2013 | Kaczur et al. |
| 2013/0105330 | A1 | 5/2013 | Teamey et al. |
| 2013/0118911 | A1 | 5/2013 | Sivasankar et al. |
| 2013/0134048 | A1 | 5/2013 | Teamey et al. |
| 2013/0134049 | A1 | 5/2013 | Teamey et al. |
| 2013/0140187 | A1 | 6/2013 | Teamey et al. |
| 2013/0180863 | A1 | 7/2013 | Kaczur et al. |
| 2013/0186771 | A1 | 7/2013 | Zhai et al. |

FOREIGN PATENT DOCUMENTS

| | | | |
|---|---|---|---|
| DE | 2301032 | A | 7/1974 |
| EP | 0028430 | A1 | 5/1981 |
| EP | 2329875 | A1 | 6/2011 |
| FR | 853643 | | 3/1940 |
| GB | 1223452 | A | 2/1971 |
| JP | 64-015388 | | 1/1989 |
| WO | WO 9724320 | A1 | 7/1997 |
| WO | 9850974 | A1 | 11/1998 |
| WO | WO 0015586 | A1 | 3/2000 |
| WO | WO 200467673 | A1 | 8/2004 |
| WO | 2006074335 | A2 | 7/2006 |
| WO | 2007041872 | A1 | 4/2007 |
| WO | WO 2007041872 | A1 | 4/2007 |
| WO | 2009108327 | A1 | 9/2009 |
| WO | 2011069008 | | 6/2011 |
| WO | WO2011069008 | * | 6/2011 |
| WO | 2011116236 | A2 | 9/2011 |
| WO | 2012015921 | A1 | 2/2012 |
| WO | WO 2012046362 | A1 | 4/2012 |

OTHER PUBLICATIONS

Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258. 1-page abstract only.
Li et al., "The Electro-Reduction of Carbon Dioxide in a Continuous Reactor", J. of Applied Electrochemistry (no month, 2005), vol. 35, pp. 955-965.
Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.
Yuan et al., "Electrochemical Activation of Carbon Dioxide for Synthesis of Dimethyl Carbonate in an Ionic Liquid", Electrochimica Acta (no month, 2009), vol. 54, pp. 2912-2915.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.
Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.
Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.
Fisher et al., "Electrocatalytic reduction of carbon dioxide by using macrocycles of nickel and cobalt", Journal of the American Chemical Society, vol. 102, No. 24, Sep. 1, 1980, pp. 7361-7363.
Ishida et al., Selective Formation of HC00—In the Electrochemical CO2 Reduction Catalyzed by URU(BPY)2(CO)2 3/4 2+ (BPY = 2,2'-Bipyridine), Journal of the Chemical Society, Chemical Communications, Chemical Society, Letchworth, GB, Jan. 1, 1987, pp. 131-132.
Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.
B. Eneau-Innocent et al., Electroreduction of carbon dioxide at a lead electrode in propylene carbonate: A spectroscopic study, Applied Catalysis B: Environmental 98 (2010) 65-71.
Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.
S. Gambino and G. Silvestri, On the electrochemical reduction of carbon dioxide and ethylene, Tetrahedron Letters No. 32, pp. 3025-3028, 1973, Pergamon Press, Printed in Great Britain.
K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.
James Grimshaw, Electrochemical Reactions and Mechanisms in Organic Chemistry, 2000, ISBN 978-0-444-72007-8. [retrieved on Jan. 3, 2014]. Retrieved from the Internet. <URL: http://f3.tiera.ru/ShiZ/Great%20Science%20TextBooks/Great%Science%20Textbooks%20DVD%20Library%202007%20-%20Supplement%20Five/Chemistry/Organic%20Chemistry/Electrochemical%20Reactions%20and%20Mechanisms%20-in%20Organic%20Chemistry%20-%20J.%20Grimshaw%20%28Elsevier,%202000%29%WW.pdf>.
Fischer, J. et al. "The production of oxalic acid from CO2 and H2O." Journal of Applied Electrochemistry, 1981, vol. 11, pp. 743-750.
Goodridge, F. et al., The electrolytic reduction of carbon dioxide and monoxide for the production of carboxylic acids.: Journal of applied electrochemistry, 1984, vol. 14, pp. 791-796.
Wu et al., "Electrochemical Reduction of Carbon Dioxide I. Effects of the Electrolyte on the Selectivity and Activity with Sn Electrode", Journal of the Electrochemical Society (no month, 2012), vol. 159, No. 7, pp. F353-F359.
Chaplin et al., "Effects of Process Conditions and Electrode Material on Reaction Pathways for Carbon Dioxide Electroreduction with Particular Reference to Formate Formation", Journal of Applied Electrochemistry (no month, 2003), vol. 33, pp. 1107-1123.
Jaime-Ferrer et al., "Three-Compartment Bipolar Membrane Electrodialysis for Splitting of Sodium Formate into Formic Acid and Sodium Hydroxide: Role of Diffusion of Molecular Acid", Journal of Membrane Science (no month, 2008), vol. 325, pp. 528-536.
Green et al., "Vapor-Liquid Equilibria of Formaldehyde-Methanol-Water", Industrial and Engineering Chemistry (Jan. 1955), vol. 47, No. 1, pp. 103-109.
Shibata et al., "Electrochemical Synthesis of Urea at Gas-Diffusion Electrodes Part VI. Simultaneous Reduction of Carbon Dioxide and

(56) References Cited

OTHER PUBLICATIONS

Nitrite Ions with Various Metallophthalocyanine Catalysts". J. of Electroanalytical Chemistry (no month, 2001), vol. 507, pp. 177-184.
Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).
Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.
Perez et al., "Activation of Carbon Dioxide by Bicyclic Amidines", J. Org. Chem. (no month, 2004), vol. 69, pp. 8005-8011.
Seshadri et al., A New Homogeneous Electrocatalyst for the Reduction of Carbon Dioxide to Methanol at Low Overpotential, Journal of Electroanalytical Chemistry, 372 (1994), 145-50.
Green et al., Vapor-Liquid Equilibria of Formaldehyde-Methanol-Water, Industrial and Engineering Chemistry (Jan. 1955), vol. 47, No. 1, pp. 103-109.
Scibioh et al., Electrochemical Reduction of Carbon Dioxide: A Status Report, Proc Indian Natn Sci Acad (May 2004), vol. 70, A, No. 3, pp. 407-462.
Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.
Perez et al., Activation of Carbon Dioxide by Bicyclic Amidines, J. Org. Chem. (no month, 2004), vol. 69, pp. 8005-8011.
Zaragoza Dorwald, Side Reactions in Organic Synthesis, 2005, Wiley-VCH Verlag GmbH & Co. KGaA, Weinheim, Preface. p. IX.
Liansheng et al, Journal of South Central University Technology, Electrode Selection of Electrolysis with Membrane for Sodium Tungstate Solution, 1999, 6(2), pp. 107-110.
Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.
Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.
Hori et al, chapter on "Electrochemical CO2 Reduction on Metal Electrodes," in the book "Modern Aspects of Electrochemistry," vol. 42, pp. 106 and 107, published in 2008.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("O") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.
Tinnemans et al., "Tetraaza-macrocyclic cobalt(II) and nickel(II) complexes as electron-transfer agents in the photo (electro)chemical and electrochemical reduction of carbon dioxide," Recl.Trav. Chim. Pays-Bas, Oct. 1984, 103: 288-295.
Bocarsly et al., "Photoelectrochemical conversion of carbon dioxide to methanol and higher alcohols, a chemical carbon sequestration strategy," Preprints of Symposia—American Chemical Society, Division of Fuel Chemistry, vol. 53, Issue: 1, pp. 240-241.
Nefedov and Manov-Yuvenskii, The Effect of Pyridine Bases and Transition-Metal Oxides on the Activity of PdCl2 in the Carbonylation of Aromatic Mononitro Compounds by Carbon Monoxide, 28 Bulletin of the Acad. of Sciences of the USSR 3, 540-543 (1979).
Vojinovic "Bromine oxidation and bromine reduction in propylene carbonate" Journal of Electroanalytical Chemistry, 547 (2003) p. 109-113.
Babic et al (Electrochimica Acta, 51, 2006, 3820-3826).
Yoshida et al. (Journal of Electroanalytical Chemistry, 385, 1995, 209-225).

\* cited by examiner

METHOD AND SYSTEM FOR PRODUCTION OF OXALIC ACID AND OXALIC ACID REDUCTION PRODUCTS

CROSS REFERENCE TO RELATED APPLICATIONS

The present application claims the benefit under 35 U.S.C. §120 of PCT application, International application No. PCT/US2013/077610 filed Dec. 23, 2013. PCT application, International application No. PCT/US2013/077610 filed Dec. 23, 2013 is incorporated by reference in its entirety.

PCT application, International application No. PCT/US2013/077610 filed Dec. 23, 2013 claims the benefit under 35 U.S.C. §119(e) of U.S. Provisional Application Ser. No. 61/745,204 filed Dec. 21, 2012, U.S. Provisional Application Ser. No. 61/794,230 filed Mar. 15, 2013, U.S. Provisional Patent Application Ser. No. 61/816,531 filed Apr. 26, 2013, U.S. Provisional Patent Application Ser. No. 61/844,755 filed Jul. 10, 2013 and U.S. Provisional Patent Application No. 61/846,944 filed Jul. 16, 2013. Said U.S. Provisional Application Ser. No. 61/745,204 filed Dec. 21, 2013, U.S. Provisional Application Ser. No. 61/794,230 filed Mar. 15, 2013, U.S. Provisional Patent Application Ser. No. 61/816,531 filed Apr. 26, 2013, U.S. Provisional Patent Application Ser. No. 61/844,755 filed Jul. 10, 2013 and U.S. Provisional Patent Application No. 61/846,944 filed Jul. 16, 2013 are hereby incorporated by reference in their entireties.

PCT application, International application No. PCT/US2013/077610 filed Dec. 23, 2013 claims the benefit under 35 U.S.C. §120 of U.S. patent application Ser. No. 13/724,996 filed Dec. 21, 2012. U.S. patent application Ser. No. 13/724,996 claims the benefit under 35 U.S.C. §119(e) of U.S. Provisional Application Ser. No. 61/720,670 filed Oct. 31, 2012, U.S. Provisional Application Ser. No. 61/703,232 filed Sep. 19, 2012 and U.S. Provisional Application Ser. No. 61/675,938 filed Jul. 26, 2012. Said U.S. patent application Ser. No. 13/724,996, said U.S. Provisional Application Ser. No. 61/720,670 filed Oct. 31, 2012, U.S. Provisional Application Ser. No. 61/703,232 filed Sep. 19, 2012 and U.S. Provisional Application Ser. No. 61/675,938 filed Jul. 26, 2012 are incorporated by reference in their entireties.

TECHNICAL FIELD

The present disclosure generally relates to the field of electrochemical reactions, and more particularly to a method and system for production of oxalic acid and oxalic acid reduction products.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY OF THE PREFERRED EMBODIMENTS

The present disclosure is directed to a method and system for production of oxalic acid and oxalic acid reduction products. The production of oxalic acid and oxalic acid reduction products may include the electrochemical conversion of $CO_2$ to oxalate and oxalic acid. The method and system for production of oxalic acid and oxalic acid reduction products may further include the acidification of oxalate to oxalic acid, the purification of oxalic acid and the hydrogenation of oxalic acid to produce oxalic acid reduction products.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Figure 1:
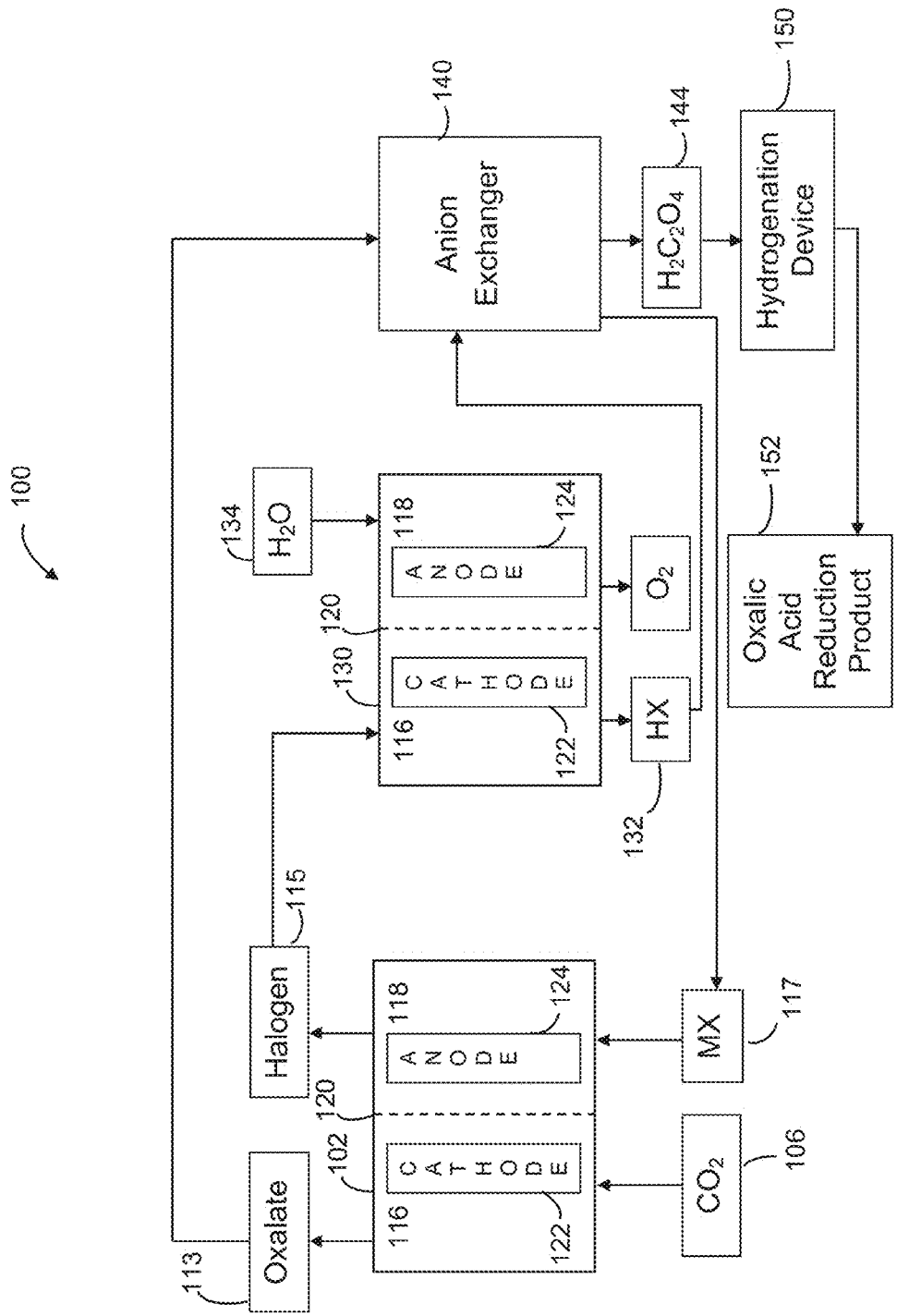
FIG. 1 is a schematic illustrating a system for the electrochemical reduction of carbon dioxide to oxalate; the conversion of oxalate to oxalic acid; and the conversion of oxalic acid to other products.

Reference will now be made in detail to the subject matter disclosed, which is illustrated in the accompanying drawings.

The present disclosure is directed to a method and system for production of oxalic acid and oxalic acid reduction products.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

The following definitions are used: TAA—tetraalkylammonium; TAAX—tetraalkylammonium halide; TBA—tetrabutylammonium; TBAX—tetrabutylammonium halide; TBABr—tetrabutylammonium bromide; TBAP—tetrabutylammonium perchlorate; TPABr—tetrapropylammonium bromide; TBAOx or TBA$_2$Ox or TBAO—tetrabutylammonium oxalate; PC—propylene carbonate; ACN—acetonitrile; CO$_2$—carbon dioxide; HBr—Hydrobromic acid; BUTY—Gamma butyrolactone, γ-butyrolactone; OA—oxalic acid; DEO—diethyl oxalate; DMO—dimethyl oxalate; EtOH—ethanol; BuOH—butanol; DBO—dibutyl oxalate Electrochemical conversion of CO$_2$ to oxalate may be undertaken in non-aqueous media to achieve high yields. However, oxalate is a salt that has limited utility. The acid form of oxalate, oxalic acid, has many more industrial uses and may advantageously be used as an intermediate for the production of a large variety of chemical compounds such as glyoxylic acid, glyoxylate, glycolic acid, glycolate, glyoxal, glycolaldehyde, ethylene glycol, acetic acid, acetaldehyde, ethanol, ethane, ethylene, and certain metal oxalates such as ferrous oxalate. An economical process of acidifying oxalate to oxalic acid in a combined process with CO$_2$ to oxalate conversion is therefore advantageous. As used herein, it should be understood that ethylene glycol may also be referred as monoethylene glycol and mono-ethylene glycol and may be simply referred as (MEG). As used herein, ethylene glycol, mono-ethylene glycol, monoethylene glycol and MEG may be used interchangeably and may refer to the chemical of C$_2$H$_6$O$_2$.

A second problem in non-aqueous CO$_2$ electrochemical conversion is finding an appropriate anodic process. Halogens may be produced, but these are not always marketable because of their high toxicity. The present disclosure may include a method and system for production of oxalic acid and oxalic acid reduction products which advantageously produces no toxic compounds. When production of a halogen is desired, however, another embodiment may include the anodic generation of a halogen and cathodic production of oxalate or oxalic acid depending upon the specific process employed.

Referring to FIG. 1, a schematic illustrating a system 100 for the electrochemical reduction of carbon dioxide to oxalate; the conversion of oxalate to oxalic acid; and the conversion of oxalic acid to other products is shown. System 100 may be configured for production of oxalic acid and oxalic acid reduction products in accordance with an embodiment of the present disclosure.

It is contemplated that system 100 may operate according to the overall chemical equation:

$$4CO_2 + 2H_2O \rightarrow 2H_2C_2O_4 + O_2 \qquad [1]$$

Advantageously, a halogen and halide salt may be recycled and may not be consumed in the reactions of system 100.

System 100 may include an electrochemical cell (also referred as a container, electrolyzer, or cell) 102. Electrochemical cell 102 may be implemented as a divided cell. The divided cell may be a divided electrochemical cell. Electrochemical cell 102 may include a first region 116 and a second region 118. First region 116 and second region 118 may refer to a compartment, section, or generally enclosed space, and the like without departing from the scope and intent of the present disclosure. First region 116 may include a cathode 122. Second region 118 may include an anode 124. First region 116 may include a catholyte, the catholyte including carbon dioxide which may be dissolved in the catholyte. Second region 118 may include an anolyte which may include MX 117.

Electrochemical cell 102, and all electrochemical cells described herein, uses an energy source, not shown, which may generate an electrical potential between the anode 124 and the cathode 122. The electrical potential may be a DC voltage. Energy source may also be configured to supply a variable voltage or constant current to electrochemical cell 102 or any electrochemical described herein.

Separator 120 may selectively control a flow of ions between the first region 116 and the second region 118. Separator 120 may include an ion conducting membrane, separator, or diaphragm material.

Electrochemical cell 102 is generally operational to reduce carbon dioxide in the first region 116 to a first product, such as an oxalate. Oxalate 113 may be referred as an oxalate salt and may include a general formula of $M_nC_2O_4$ where N=1 or 2. Oxalate 113 may be recoverable from the first region 116 while a second product, such as a halogen or trihalide anion 115, may be recoverable from the second region 118. Carbon dioxide source 106 may provide carbon dioxide to the first region 116 of electrochemical cell 102. In some embodiments, the carbon dioxide is introduced directly into the region 116 containing the cathode 122. It is contemplated that carbon dioxide source 106 may include a source of a mixture of gases in which carbon dioxide has been separated from the gas mixture.

It is contemplated that a first product, such as oxalate, may be extracted by a first product extractor, not shown. First product extractor may implement an organic product and/or inorganic product extractor. First product extractor may be generally operational to extract (separate) the first product, such as oxalate 113, from the first region 116. The extracted oxalate 113 may be presented through a port of the system 100 for subsequent storage and/or consumption by other devices and/or processes.

The anode side of the reaction occurring in the second region 118 of electrochemical cell 102, and any other electrochemical cells described herein, may include MX 117 supplied to the second region 118. MX 117 may also comprise $MX_2$ if two anions are need for charge balance. Salt MX 117 may act as both an anodic reactant as well as a supporting electrolyte. The second product recoverable from the second region 118 may be a halogen or trihalide ion 115. MX 117 may include a cation, as M may be $Li^+$, $Na^+$, $K^+$, $Ca^{++}$, $Ba^{++}$, $Sr^{++}$, $Mg^{++}$, a $R_1R_2R_3R_4N^+X^-$ where each of $R_{1-4}$ is independently selected from the group consisting of alkyl, branched alkyl, cycloalkyl, and aryl, tetraalkyl ammonium, tetramethylammonium, tetraethylammonium, tetrabutylammonium, tetraphenylphosphonium, tetrabutylphosphonium, tetraethylphosphonium, tetrahexylammonium, tetraoctylammonium, methyl tributylammonium, butyltrimethylammonium, 1-n-butyl-3-methylimidazolium, 1-ethyl-3-methylimidazolium, 1-ethyl-1-methylpyrrolidinium, di-n-decyldimethylammonium, choline, or ammonium. To increase electrolyte solubility, crown ethers, such as 12-crown-4, 15-crown-5, diphenyl-18-crown-6, and 18-crown-6, may be used with the cation such as $Li^+$, $Na^+$, or K. The electrolyte used will also determine the type of membrane or separator that may be selected for the electrochemical cell 102. Ionic liquids may also be employed as electrolytes, as well as CTAB, hexadecyltributyl phosphonium bromide, and the Stark catalyst. X may include F, Cl, Br, I, $BF_4$, $PF_6$, $ClO_4$, or an anion; and mixtures thereof.

It is contemplated that a second product, such as halogen or trihalide anion 115, may be extracted by a second product extractor, not shown. Second product extractor may implement an organic product and/or inorganic product extractor. Second product extractor may be generally operational to extract (separate) the second product, such as a halogen or trihalide anion 115, from the second region 118. The extracted halogen or trihalide anion 115 may be presented through a port of the system 100 for subsequent storage and/or consumption by other devices and/or processes. It is contemplated that first product extractor and/or second product extractor (not shown) may be implemented with electrochemical cell 102, or may be remotely located from the electrochemical cell 102. Additionally, it is contemplated that first product extractor and/or second product extractor may be implemented in a variety of mechanisms and to provide desired separation methods, such as fractional distillation or molecular sieve drying, without departing from the scope and intent of the present disclosure.

In one embodiment, electrochemical cell 102 may reduce $CO_2$ to an oxalate salt ($M_2C_2O_4$) at the cathode 122 and may oxidize a halogen containing salt of the formula MX, where M is a cation and X is a halide anion, at the anode 124 produce a halogen or trihalide anion 115. This liberates the cation ($M^+$) to be transferred across a membrane or separator 120 to pair with the oxalate anion in the first region 116, or also referred as the catholyte compartment. An oxidation resistant cation exchange membrane or separator may be employed as the separator 120.

Halogen or trihalide anion 115 may be fed to an electrochemical reduction cell 130. It is contemplated that electrochemical reduction cell 130 may be similar to electrochemical cell 102. For example, electrochemical reduction cell 130 may include a first region and a second region. First region and second region may refer to a compartment, section, or generally enclosed space, and the like without departing from the scope and intent of the present disclosure. First region may include a cathode. Second region 118 may include an anode 124. Electrochemical reduction cell 130 may reduce halogen or trihalide anion 115 to HX 132 at the cathode and oxidizes water 134 at the anode, producing oxygen ($O_2$) and liberating hydrogen ions ($H^+$) to be transferred across the membrane of the electrochemical reduction cell 130 to generate the HX 132.

Oxalate 113 may be fed to an anion exchanger 140. Anion exchanger 140 may refer to an ion exchanger that exchange negatively charged ions, the anions. Anion exchanger 140 may convert oxalate 113 to oxalic acid 144 using the HX 132 produced from electrochemical reduction cell 130. Anion exchanger 140 may further produce MX 117 which may be recycled to the second region 118 of electrochemical cell 102.

Oxalic acid 144 may be further converted to a range of more reduced two-carbon (or $C_2$) species. Oxalic acid 144 may be fed to a hydrogenation device 150, such as a thermal catalytic hydrogenation device or electrochemical reduction device. Oxalic acid 144 may be converted to an oxalic acid reduction product 152. Oxalic acid reduction product 152 may include two-carbon species such as glyoxylic acid, glyoxal, glycolic acid, glycolaldehyde, acetaldehyde, ethylene glycol, ethanol, acetic acid, ethane, or ethylene. Oxalic acid may also be converted to alkyl oxalates such as dimethyl oxalate by reaction with an alcohol.

Figure 2:
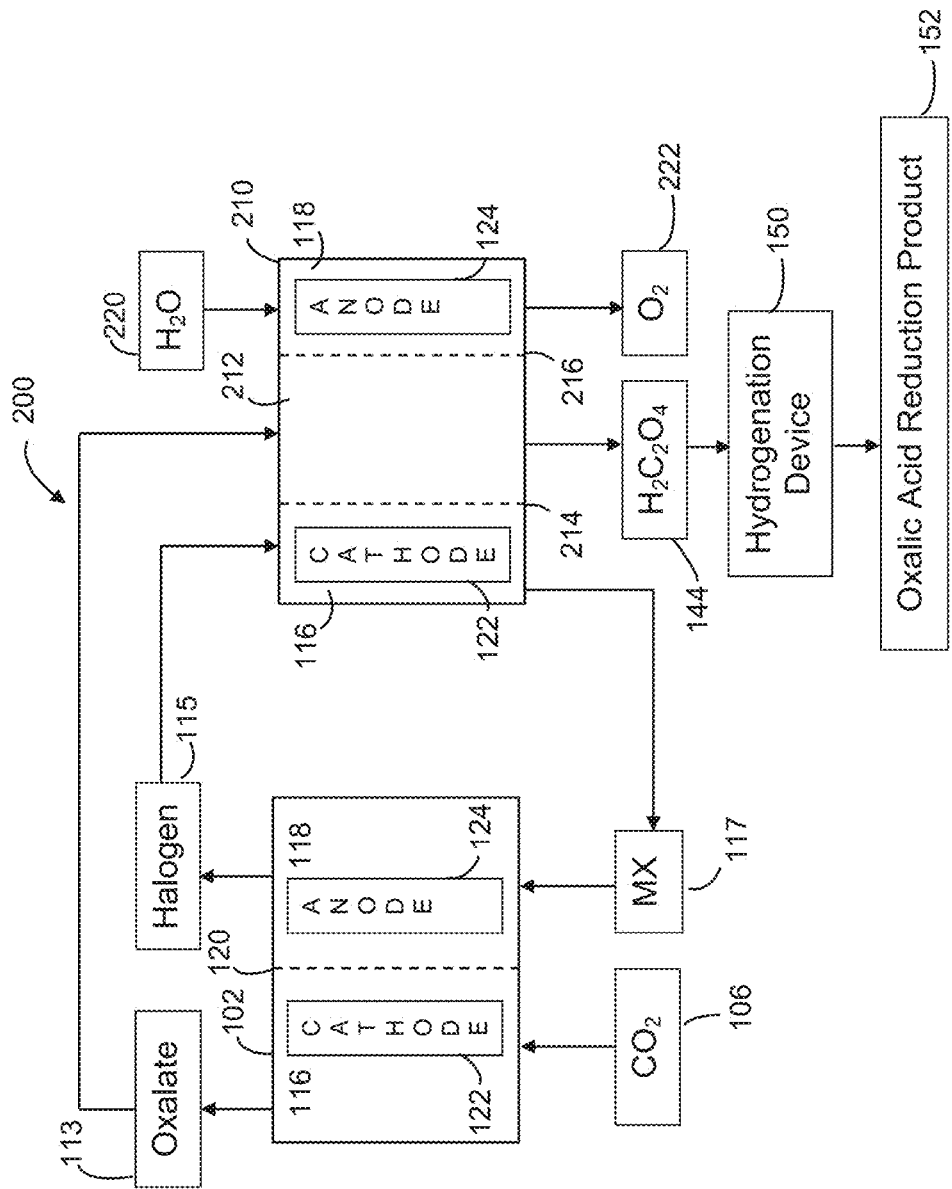
FIG. 2 is a schematic illustrating a system for the electrochemical reduction of carbon dioxide to oxalate; the conversion of oxalate to oxalic acid; and the conversion of oxalic acid to other products.

Referring to FIG. 2, a schematic illustrating a system 200 for the electrochemical reduction of carbon dioxide to oxalate; the conversion of oxalate to oxalic acid; and the conversion of oxalic acid to other products is shown. System 200 may include electrochemical cell 102, electrochemical cell 210 and hydrogenation device 150.

Similar to system 100, electrochemical cell 102 of system 200 may reduce $CO_2$ from carbon dioxide source 106 to an oxalate salt ($M_2C_2O_4$) at the cathode 122 and oxidizes a halogen containing salt of the formula MX, where M is a cation and X is a halide anion, at the anode 124 to produce a halogen or trihalide anion 115. This liberates the cation ($M^+$) to be transferred across a membrane or separator 120 to pair with the oxalate anion in the first region 116, or also referred as the catholyte compartment. An oxidation resistant cation exchange membrane may be employed as the separator 120.

Electrochemical cell 210, also referred to an electrochemical acidification unit, may include three regions or compartments. Electrochemical cell 210 may include a first region 116, a second region 118 and a third region 212. Third region 212 may be a central ion exchange region bounded by two cation exchange membranes or separators 214, 216. First region 116 may include a cathode 122 and may be fed halogen or trihalide anion 115 from the second region of electrochemical cell 102. Second region 118 may include an anode 124 and may be fed water 220. Electrochemical cell 210 may be configured to acidify the oxalate salt fed to the central ion exchange region 212 to produce oxalic acid 144. MX may be recoverable from first region 116 of electrochemical cell 210 and recycled to the second region 118 of electrochemical cell 102. In the second region 118 of electrochemical cell 210, the anode reaction may generate hydrogen ions that pass through the adjoining cation membrane 216 into the ion exchange region 212. Oxygen 222 may be produced from the oxidation of water that may be recoverable from the second region 118. It is contemplated that the second region 118 of electrochemical cell 210 may include an acid electrolyte such as sulfuric acid.

Oxalic acid 144 may be further converted to a range of more reduced two-carbon species. Oxalic acid 144 may be fed to a hydrogenation device 150, such as a thermal catalytic hydrogenation device or electrochemical reduction device. Oxalic acid 144 may be converted to an oxalic acid reduction product 152. It is contemplated that system 200 may operate according to the overall chemical equation:

$$4CO_2 + 2H_2O \rightarrow 2H_2C_2O_4 + O_2 \quad [2]$$

Figure 3:
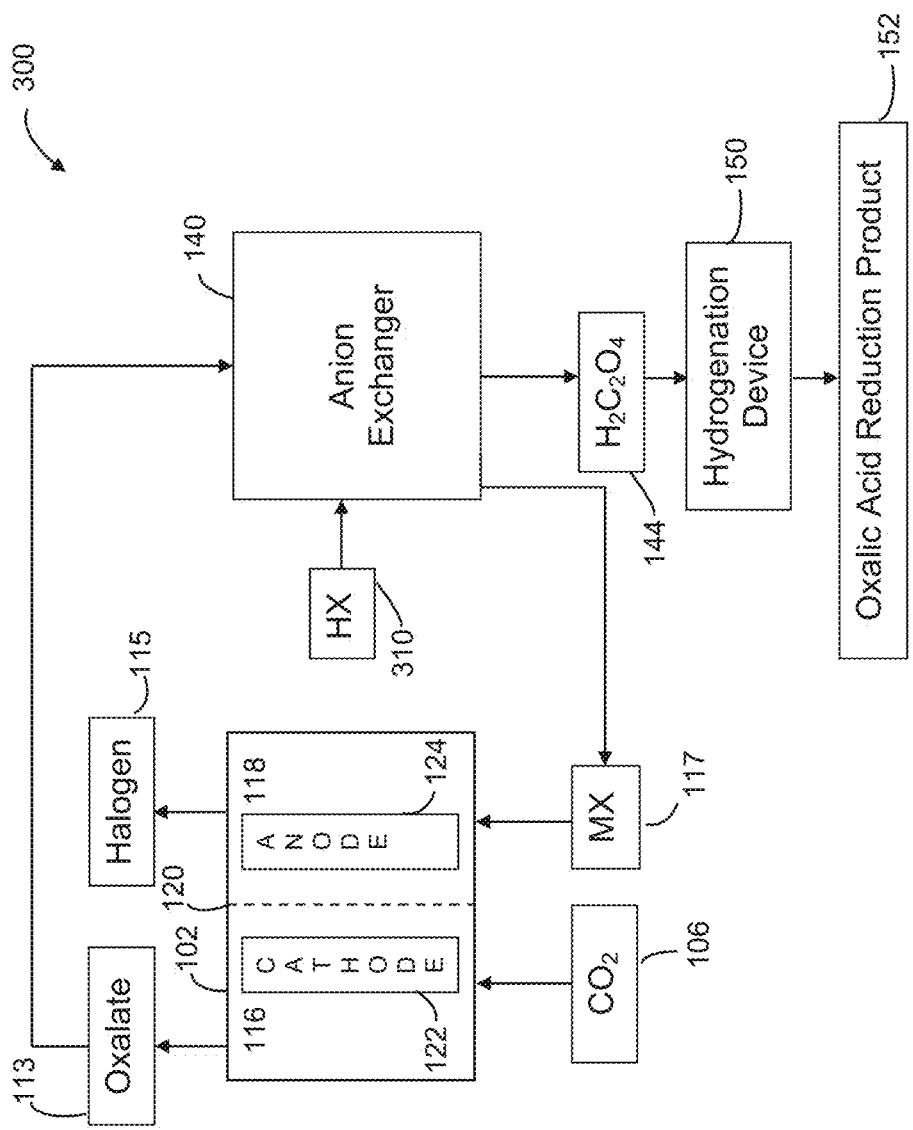
FIG. 3 is a schematic illustrating a system for the electrochemical reduction of carbon dioxide to oxalate; the conversion of oxalate to oxalic acid; and the conversion of oxalic acid to other products.

Referring to FIG. 3, a schematic illustrating a system 300 for the electrochemical reduction of carbon dioxide to oxalate; the conversion of oxalate to oxalic acid; and the conversion of oxalic acid to other products is shown. System 300 may include an electrochemical cell 102, an anion exchanger 140, and a hydrogenation device 150.

Similar to system 100, electrochemical cell 102 of system 300 may reduce $CO_2$ from carbon dioxide source 106 to an oxalate salt ($M_2C_2O_4$) at the cathode 122 and oxidize a halogen containing salt of the formula MX, where M is a cation and X is a halide anion, at the anode 124 to produce a halogen or trihalide anion 115. This liberates the cation ($M^+$) to be transferred across a membrane or separator 120 to pair with the oxalate anion in the first region 116, or also referred as the catholyte compartment. An oxidation resistant cation exchange membrane may be employed as the separator 120.

It is contemplated that halogen or trihalide anion 115 recoverable from the second region 118 of electrochemical cell 102 may be extracted as a saleable product or as a product that may be used in a separate process, such as a bromination reaction with an organic producing a brominated organic, such as the reaction of bromine with ethane to produce bromoethane, as well as other bromination reactions in producing fine chemicals.

Oxalate 113 may be fed to anion exchanger 140. Anion exchanger 140 may refer to an ion exchanger that exchanges negatively charged ions, the anions. Anion exchanger 140 may convert oxalate 113 to oxalic acid 144 using the HX received from an HX source 310. Anion exchanger 140 may further produce MX 117 which may be recycled to the second region 118 of electrochemical cell 102. The overall chemical reaction of system 300 may be represented by:

$$2CO_2 + 2HX \rightarrow H_2C_2O_4 + X_2 \quad [3]$$

The HX source 310, configured to flow as a HX stream could be a purchased reagent in the process or could be utilized as part of a larger process scheme involving further reactions, such that the HX is recycled—for example, from the bromination of organics, which produces an HX byproduct.

Figure 4:
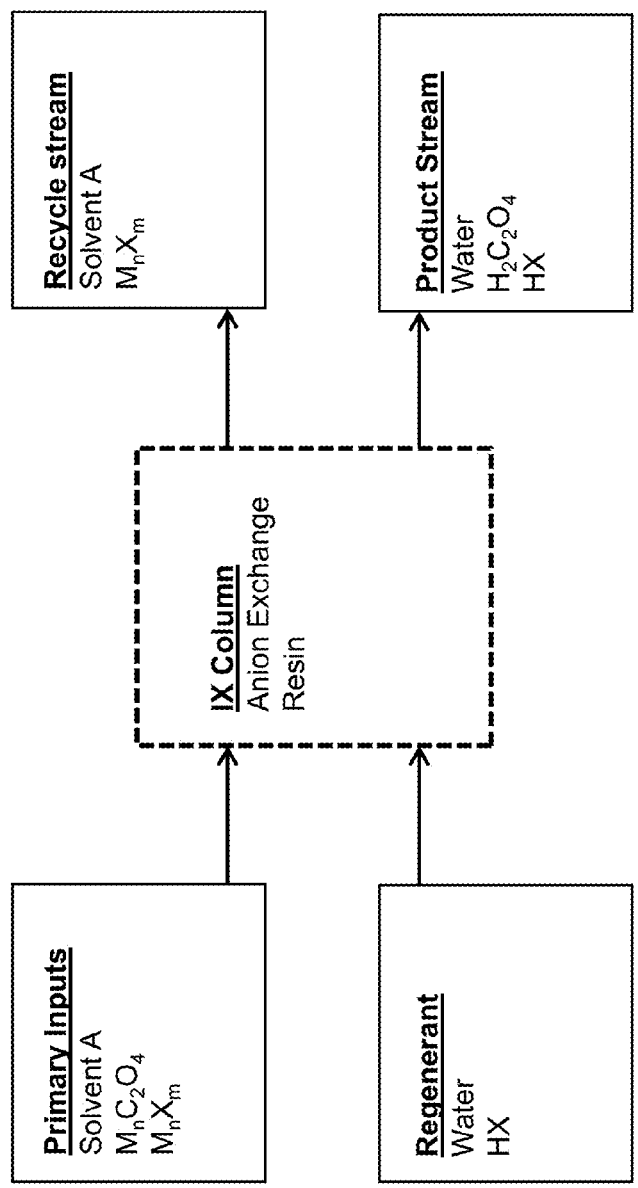
FIG. 4 is a schematic illustrating a process for converting oxalate salts to oxalic acid.
Figure 5:
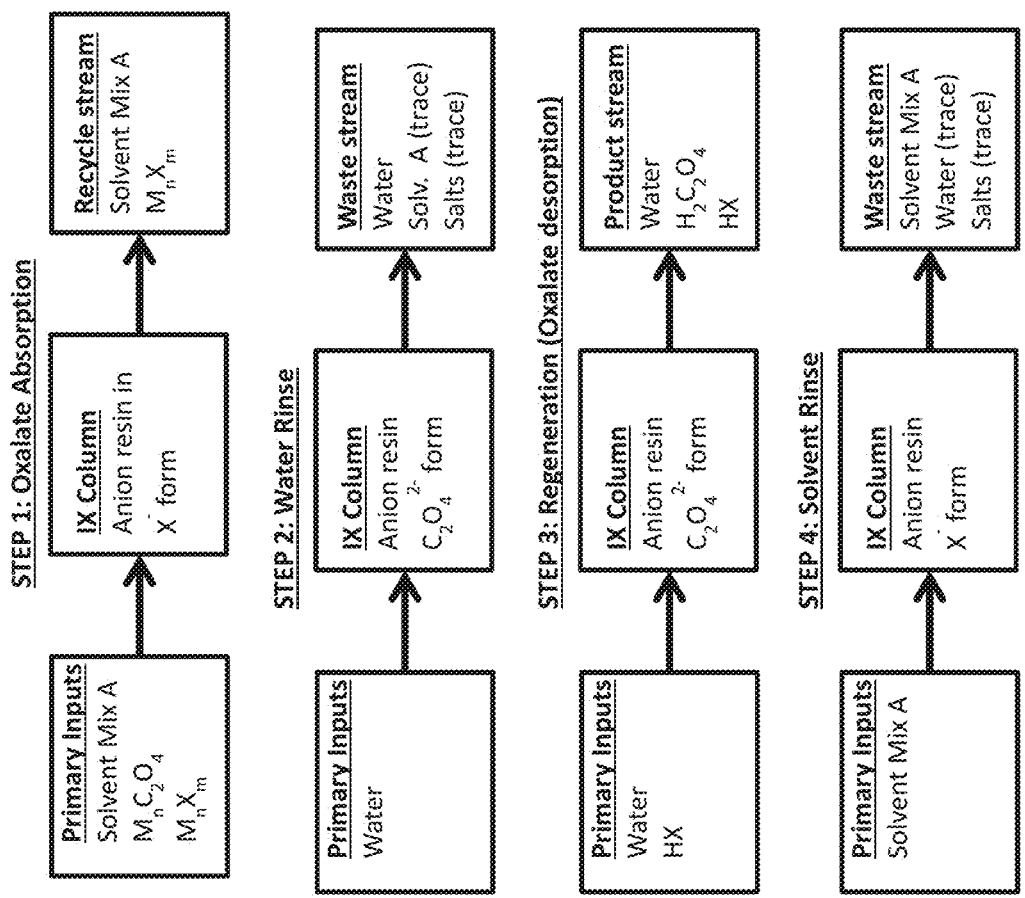
FIG. 5 is a schematic illustrating a process for converting oxalate salts to oxalic acid.

Referring to FIG. 4, a schematic illustrating a process for converting oxalate salts to oxalic acid is shown. The inputs of the anion exchange resin may include primary inputs such as a solvent, oxalate, and MX with regenerants such as water and HX. The anion exchange resin may produce a recycle stream that may include a solvent and MX and may produce a product stream of oxalic acid, water and HX. FIG. 5 is a schematic illustrating a process for converting oxalate salts to oxalic acid. Process may include an oxalate absorption process, a water rinse process, an oxalate desorption process 530 and a solvent rinse process.

Figure 6:
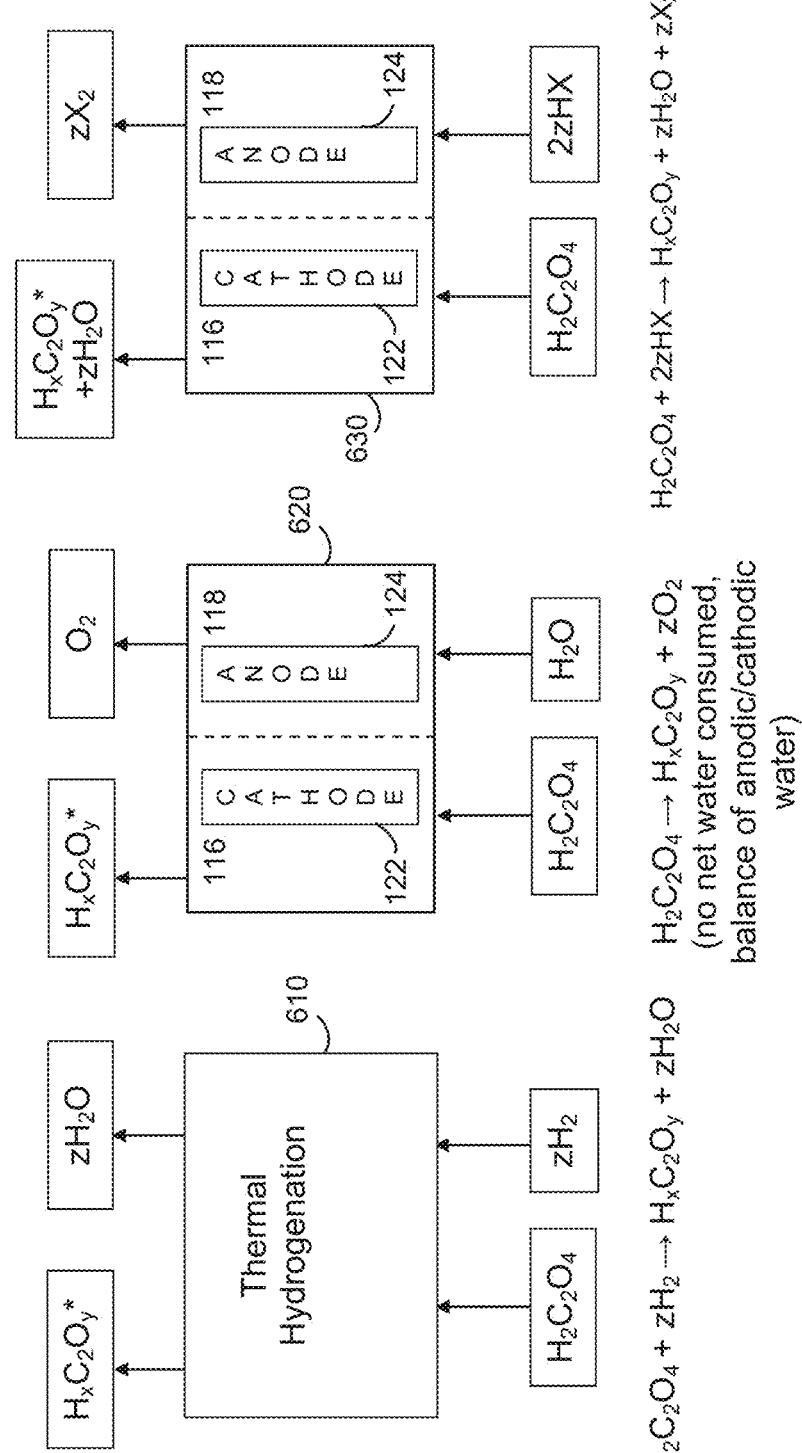
FIGS. 6A-6C are schematics illustrating hydrogenation devices for reducing oxalic acid to products.

Referring to FIGS. 6A-6C, schematics illustrating hydrogenation devices 150 for reducing oxalic acid to products are shown. FIG. 6A depicts a thermal catalytic hydrogenation device 610 that may receive oxalic acid and hydrogen and may produce an oxalic acid reduction product and water. FIG. 6B depicts an electrochemical hydrogenation cell 620. Electrochemical hydrogenation cell 620 may include an oxalic acid input to the catholyte region and a water input to the anolyte region. An oxalic acid reduction product may be recovered from the catholyte region and oxygen may be recovered from the anolyte region of the electrochemical reduction cell 620. FIG. 6C depicts an electrochemical reduction cell 630 in accordance with another embodiment of the present disclosure. Electrochemical reduction cell 630 may include an oxalic acid input to the catholyte region and a HX input to the anolyte region. An oxalic acid reduction product may be recovered from the catholyte region and a halogen may be recovered from the anolyte region of the electrochemical hydrogenation cell 630. It is contemplated that the structure of electrochemical hydrogenation cell 620, 630 may be similar to electrochemical cell 102 as previously described, including a first region having a cathode, such as a catholyte region and a second region having an anode, such as an anolyte region. The regions may be separated by a membrane or separator.

Figure 7:
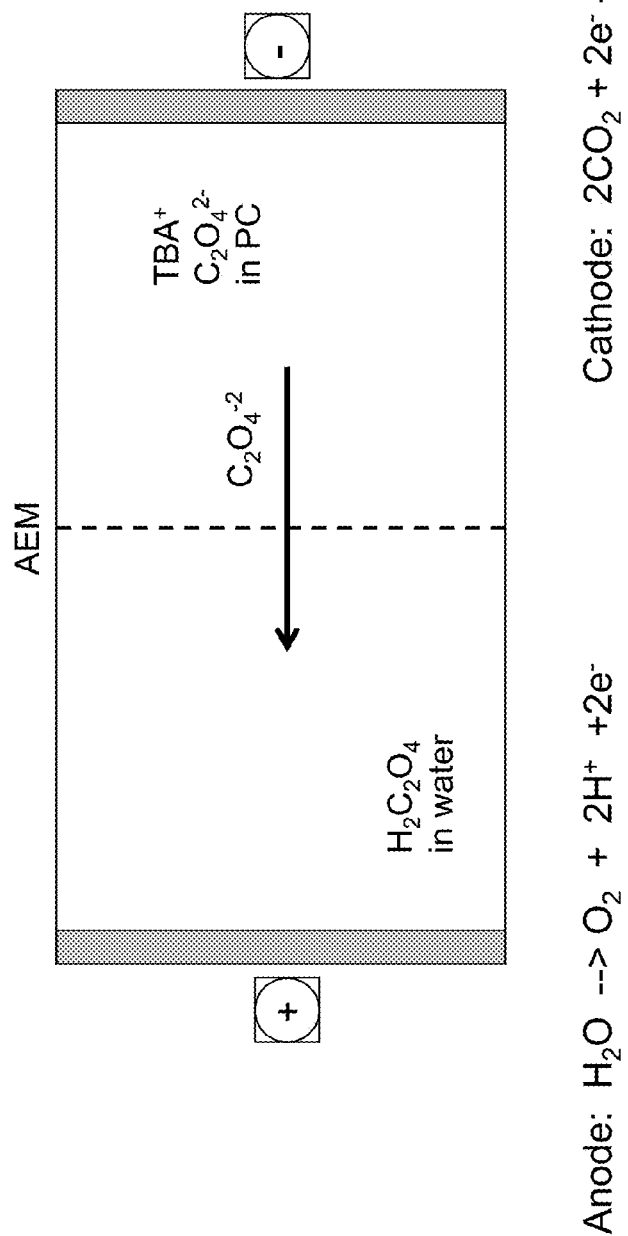
FIG. 7 is a schematic illustrating an electrochemical cell for converting oxalate salts to oxalic acid.

Referring to FIG. 7, a schematic illustrating an electrochemical cell 700 for converting oxalate salts to oxalic acid is shown. Electrochemical cell 700 may reduce $CO_2$ to an oxalate salt ($M_2C_2O_4$) at the cathode. Electrochemical cell 700 may be pre-charged with oxalic acid and the oxalate salt to enhance conductivity. The catholyte may include a non-aqueous aprotic solvent such as acetonitrile or propylene carbonate (PC). The oxalate ion may be transferred to the anolyte region through an anion exchange membrane (AEM). The anode reaction may include oxidation of water, a hydrogen halide, or any organic or inorganic species that when oxidized may liberate protons. The anolyte may include an aqueous solvent. The oxalate that would be transferred through the AEM would then be acidified by the generated protons to produce oxalic acid.

Figure 8:
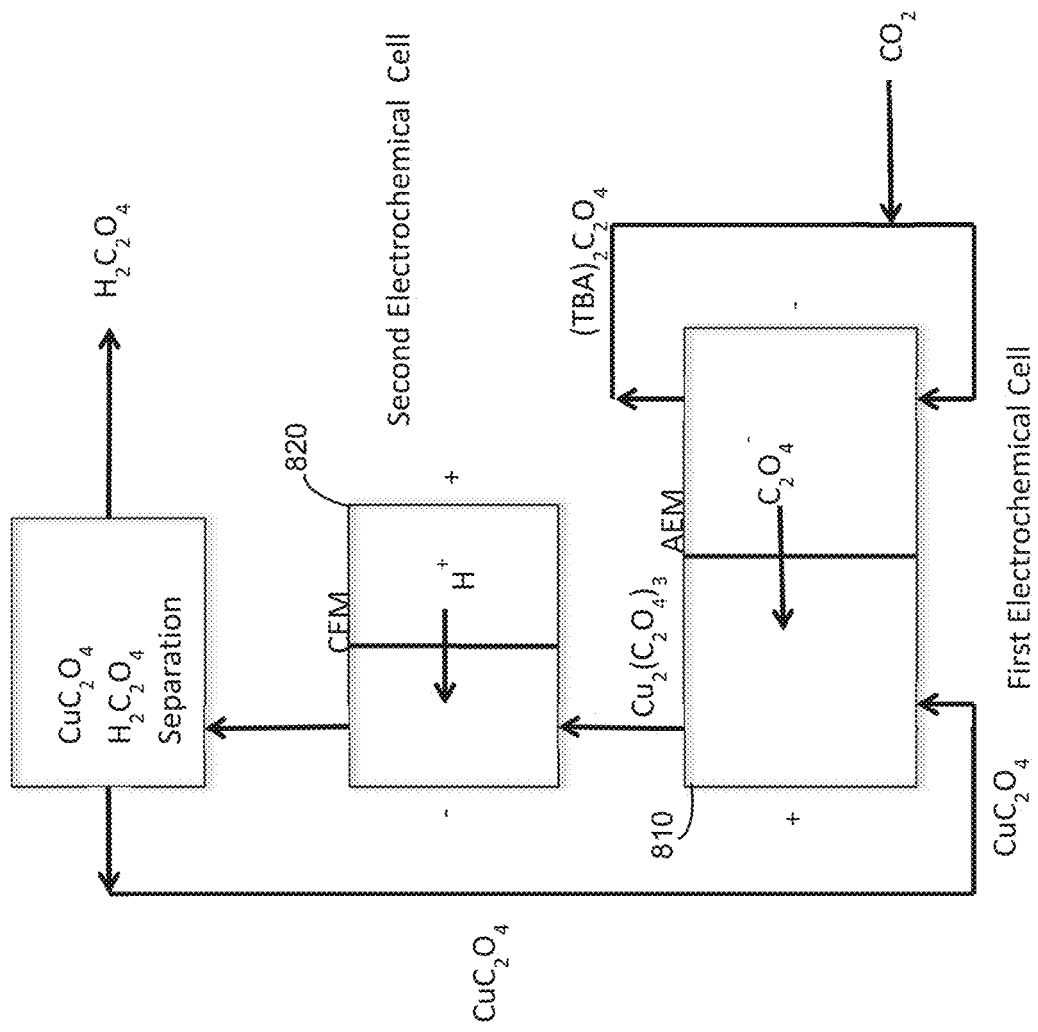
FIG. 8 is a schematic illustrating a system for converting carbon dioxide to oxalic acid.

Referring to FIG. 8, a schematic illustrating a system 800 for converting carbon dioxide to oxalic acid is shown. System 800 may include a first electrochemical cell 810 and a second electrochemical cell 820. In the first electrochemical cell 810, the anodic reaction in the first electrochemical cell 810 may involve a Cu(I)/Cu(II) couple. The advantage of using this reaction may be a lower half-cell voltage required compared to the likely voltages for operation of the electrochemical cell 700 of FIG. 7. Because of the low half-cell voltage achieved by using the Cu(I)/Cu(II) couple, the undesired oxidation of oxalic acid may be minimized. Therefore, a copper oxalate salt, $CuC_2O_4$ may be recoverable from the electrochemical cell 810. The copper oxalate salt may be acidified in a second electrochemical cell 820. In electrochemical cell 820, the anodic reaction may be water splitting, or oxidation of a hydrogen halide or other organic or inorganic species that under oxidation liberates protons. These protons would migrate across a cation exchange membrane or separator to the catholyte. The copper oxalate salt may be acidified to oxalic acid and the Cu(II) species reduced to Cu(I) to be recycled to the anodic compartment of the first electrochemical cell 810. System 800 would be operable to produce oxalic acid by employing the Cu(I)/Cu(II) couple acting as a mediator to the reaction.

Figure 9:
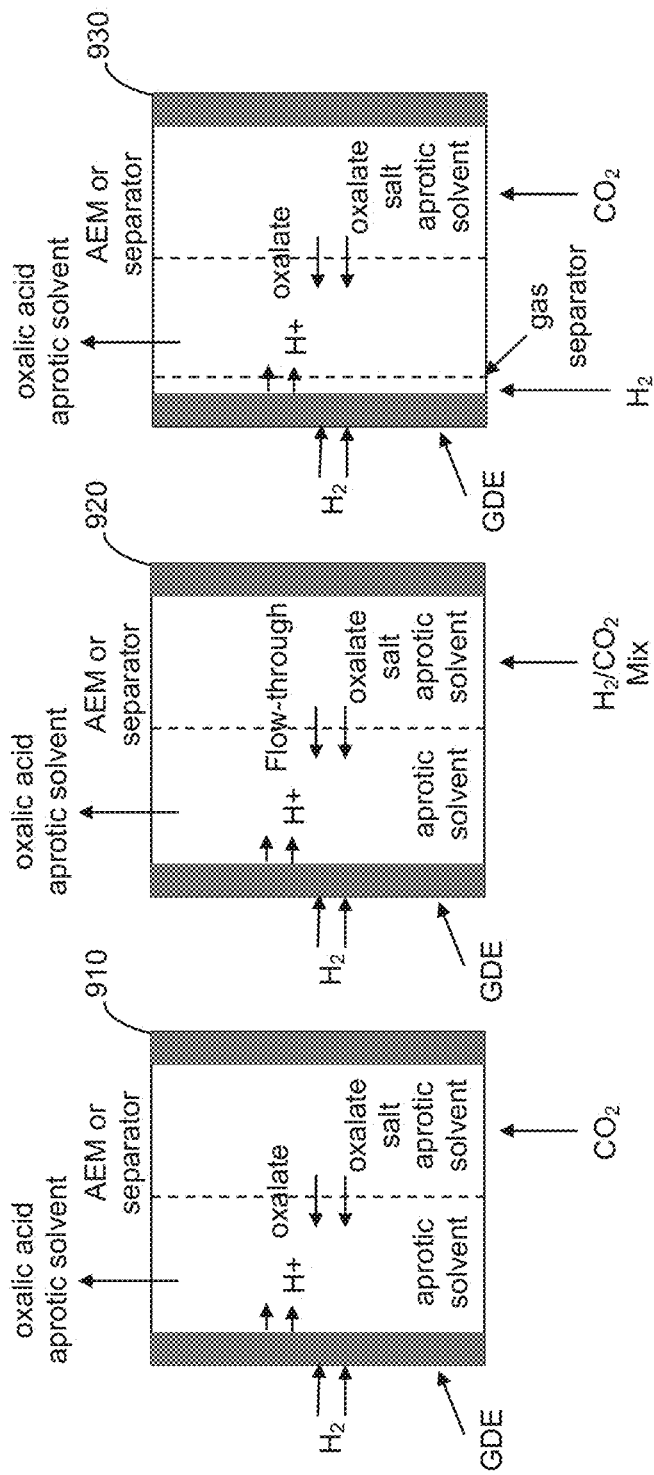
FIGS. 9A-9C are schematics illustrating a electrochemical cells for converting carbon dioxide to oxalic acid.

Referring to FIGS. 9A-9C, schematics illustrating electrochemical cells 910, 920, 930 for converting carbon dioxide to oxalic acid are shown. In each of electrochemical cells 910, 920, 930, a non-aqueous aprotic solvent (or solvents) is used for both the catholyte and the anolyte. In these modes of operation, a solvent used in the electrochemical cell 910, 920, 930 may be a non-aqueous solution and the anodes of electrochemical cells 910, 920, 930 are fed a hydrogen gas stream. The AEM would not be necessary, and likely a simple separator material may be employed. In this mode of operation, the hydrogen may serve as the anodic reactant and would be oxidized to hydrogen ions. In a similar mode of operation, the oxalate salt produced in the cathode compartment may be acidified in the anolyte to produce oxalic acid in electrochemical cell 910 as shown in FIG. 9A.

Referring to FIG. 9B, an electrochemical cell 920 which includes a mix of $H_2/CO_2$ fed into the catholyte region of the electrochemical cell 920. Electrochemical cell 920 may reduce the $CO_2$ to oxalate and the $H_2$ may be oxidized at the anode. Electrochemical cell 920 may be configured for convective flow-through of the catholyte to the anolyte region to ensure $H_2$ is available anodically and $CO_2$ is available cathodically. This may simplify the required gas feed to the electrochemical cell 920. In another embodiment, a stream of $H_2$ may be fed to the anolyte and a feed of $CO_2$ could be fed to the catholyte separately.

Referring to FIG. 9C, electrochemical cell 930 is shown. Electrochemical cell 930 may include a liquid permeable gas separator. $H_2$ gas could be fed either flow-by (as shown) or in a flow-through mode. It is contemplated that electrochemical cells 910, 920, 930 may include a similar structure as electrochemical cell 102 as previously described, unless otherwise described without departing from the scope and intent of the present disclosure.

Figure 10:
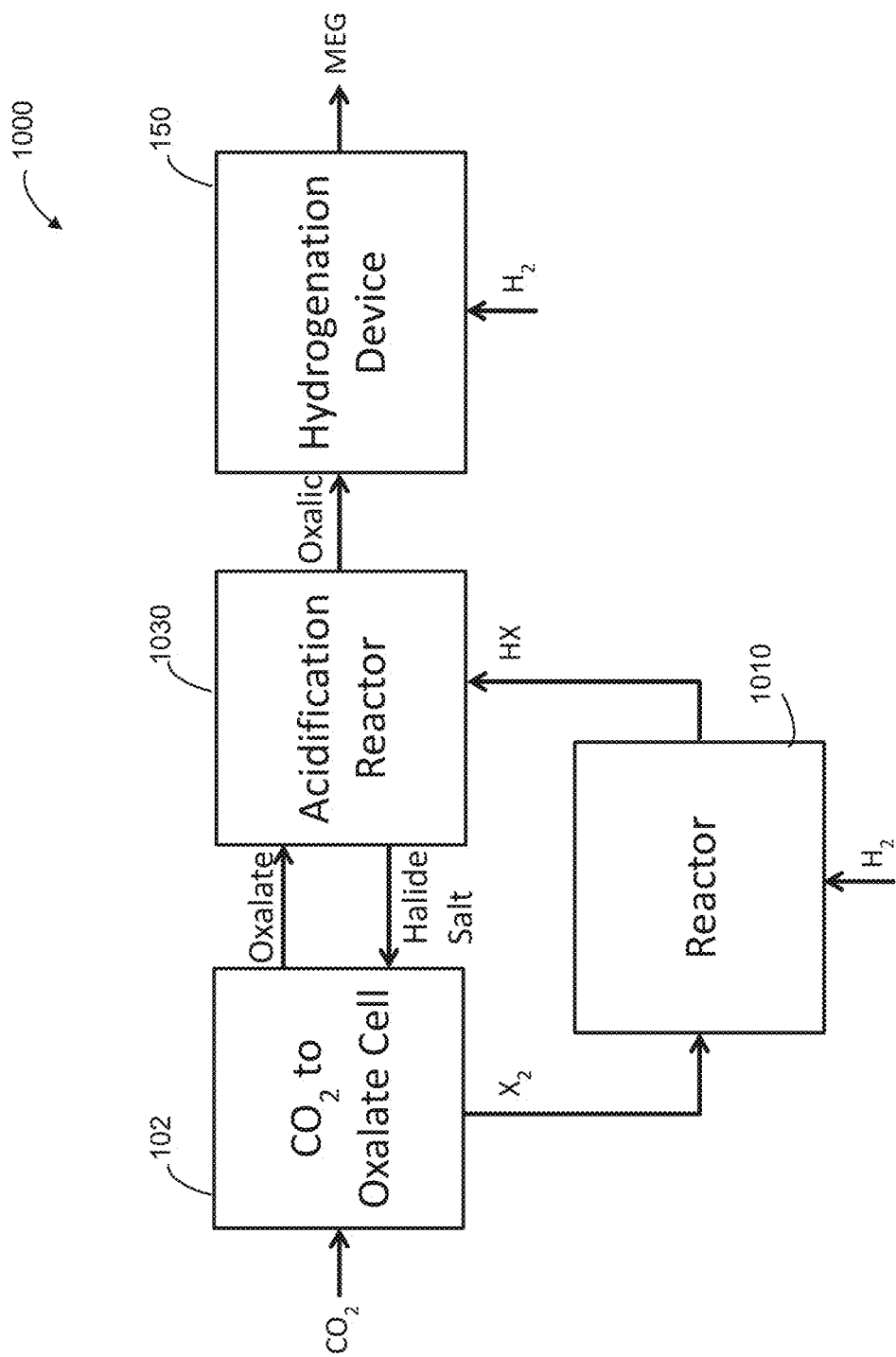
FIG. 10 is a schematic illustrating a system for the conversion of carbon dioxide to mono-ethylene glycol.

Referring to FIG. 10, a schematic illustrating a system 1000 for the conversion of carbon dioxide to mono-ethylene glycol is shown. System 1000 may include electrochemical cell 102, reactor 1010, acidification reactor 1030 and a hydogenation device 150. In electrochemical cell 102, carbon dioxide may be reduced to an oxalate salt, at the cathode of an electrochemical cell 102. A halide salt may be oxidized to a halogen or trihalide anion at the anode of the electrochemical cell 102. The reactions of electrochemical cell 102 may preferably occur in a non-aqueous solvent.

In a reactor 1010, halogen or trihalide anion produced by electrochemical cell 102 may be reacted with hydrogen to form a hydrogen halide. Reactor 1010 may be a burner or combustor wherein a significant amount of thermal energy is produced in addition to hydrogen halide. The thermal energy may then be used in other operations, such as distillation, the separation of products, and electric power generation. Alternatively, reactor 1010 may be a fuel cell. The resulting electricity may be used in a variety of ways, for example to offset some of the electrical requirements of the $CO_2$ reduction in electrochemical cell 102. Hydrogen halide from reactor 1010 may be reacted with oxalate salt from electrochemical cell 102 in an acidification reactor 1030 to produce a oxalic acid, and a halide salt. The halide salt may then be recycled to the electrochemical cell 102. The oxalic acid may be fed to hydrogenation device 150 where it is reduced to an oxalic acid reduction product, such as monoethylene glycol.

Figure 11:
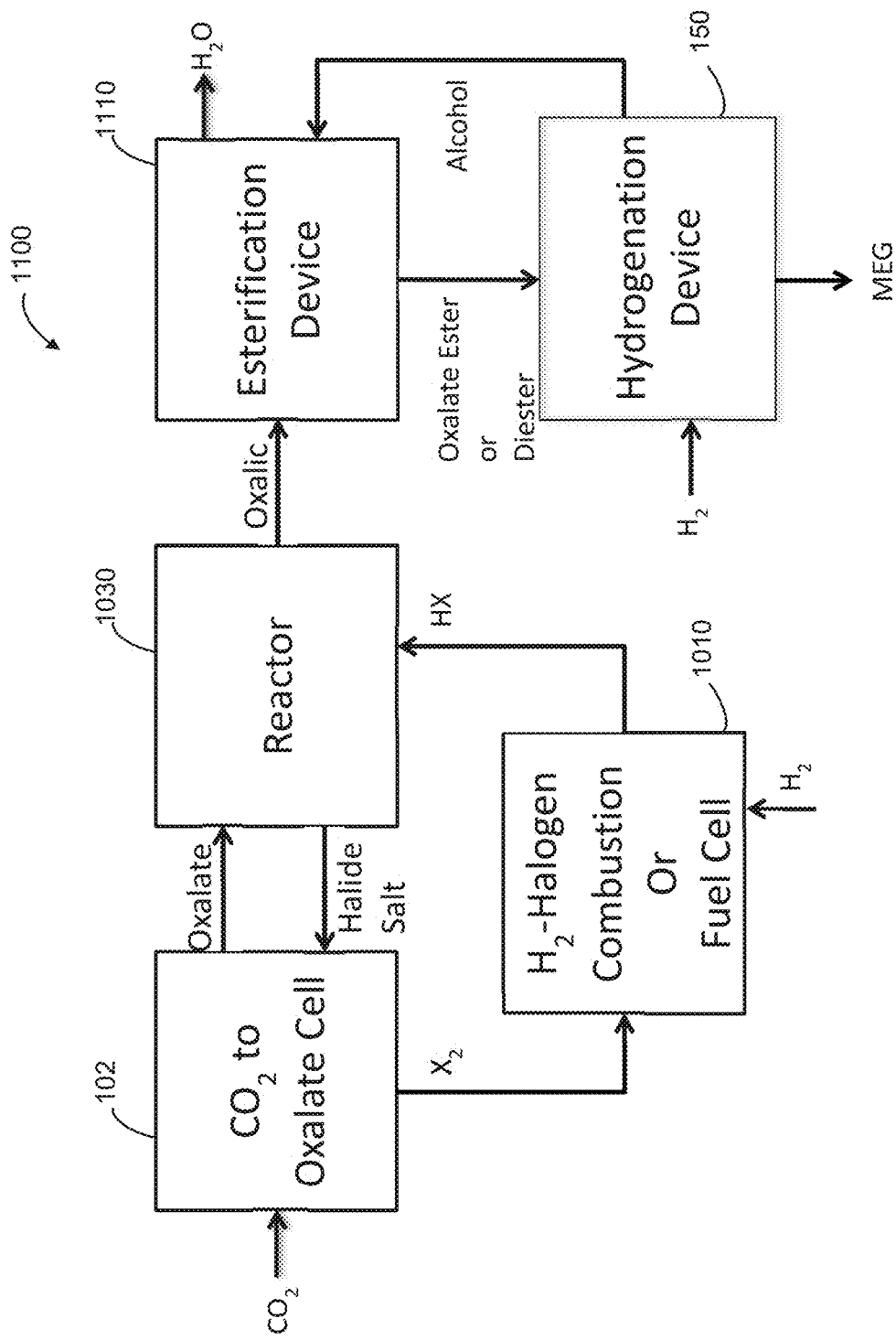
FIG. 11 is a schematic illustrating a system for the conversion of carbon dioxide to mono-ethylene glycol.

Referring to FIG. 11, a schematic illustrating a system 1100 for the conversion of carbon dioxide to mono-ethylene glycol is shown. System 1100 may include electrochemical cell 102, reactor 1010, acidification reactor 1030, esterification device 1110 and hydogenation device 150. System 1100 may include an esterfication device 1110 which may receive oxalic acid from reactor 1030 whereby the oxalic acid is reacted with an alcohol in the esterfication device 1110 to produce an oxalate ester or oxalate diester that is fed to hydrogenation device 150. In one embodiment, the oxalate ester or oxalate diester may be hydrogenated to make mono-ethylene glycol (MEG). Other products may include glyoxylic acid, glycolic acid, glyoxal, glycolaldehyde, acetic acid, acetaldehyde, ethanol, ethane, diethylene glycol, triethylene glycol, ethers, esters, polyglycols, unsaturated chemicals such as crotonaldehyde, alcohols, diols, carboxylic acids, aldehydes, and four carbon products. It is contemplated that hydrogenation device may recycle the alcohol and any oxalate ester or oxalate diester to the esterification device 1110.

Figure 12:
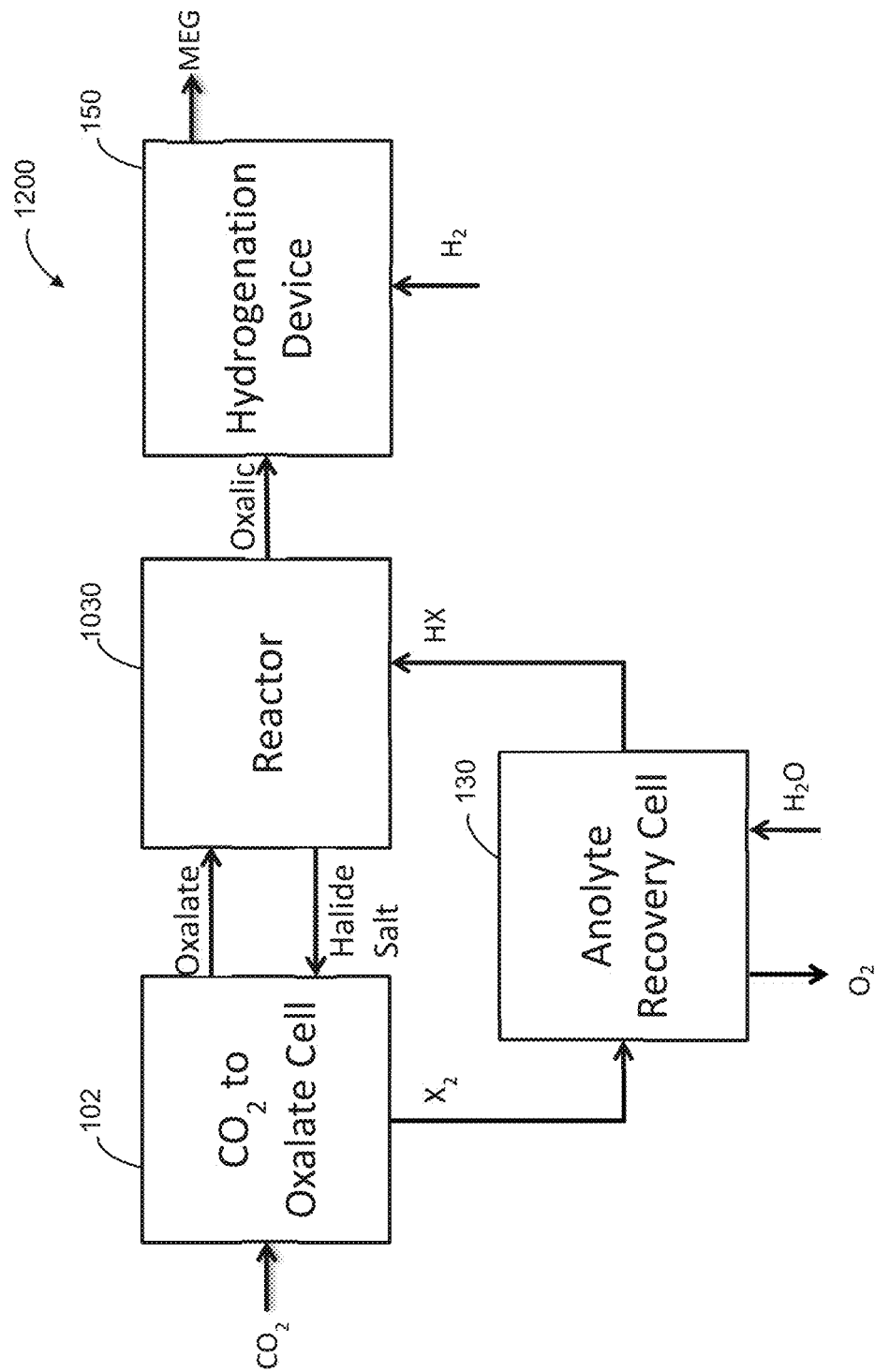
FIG. 12 is a schematic illustrating a system for the conversion of carbon dioxide to mono-ethylene glycol.

Referring to FIG. 12, a schematic illustrating a system 1200 for the conversion of carbon dioxide to mono-ethylene glycol is shown. System 1200 may include electrochemical cell 102, an anolyte recovery electrochemical cell 130, acidification reactor 1030 and hydrogenation device 150. Anolyte recovery electrochemical cell 130 may receive a halogen from electrochemical cell 102. Anolyte recovery electrochemical cell 130 may also receive water and produce HX and an oxygen byproduct. Acidification reactor 1030 is configured to receive oxalate and HX and produce a carboxylic acid, such as oxalic acid, and a halide salt. The halide salt may then be recycled to the electrochemical cell 102. The oxalic acid may be fed to hydrogenation device 150 where it is reduced to an oxalic acid reduction product, such as monoethylene glycol.

Figure 13:
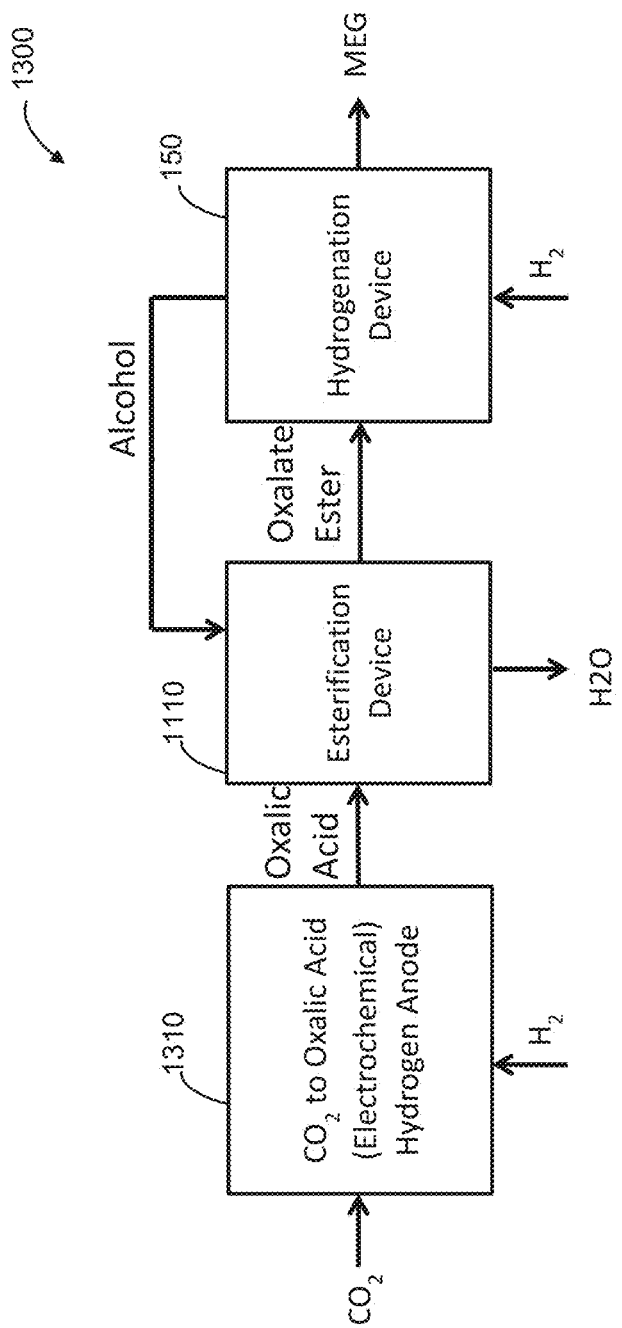
FIG. 13 is a schematic illustrating a system for the conversion of carbon dioxide to mono-ethylene glycol.

Referring to FIG. 13, a schematic illustrating a system 1300 for the conversion of carbon dioxide to mono-ethylene glycol is shown. System 1300 may include an electrochemical cell 1310 which includes a hydrogen fed anode, an esterification device 1110 and a hydrogenation device 150. Electrochemical cell 1310 may be implemented as electrochemical cells 910, 920, 930 as shown in FIGS. 9A-9C.

Figure 14:
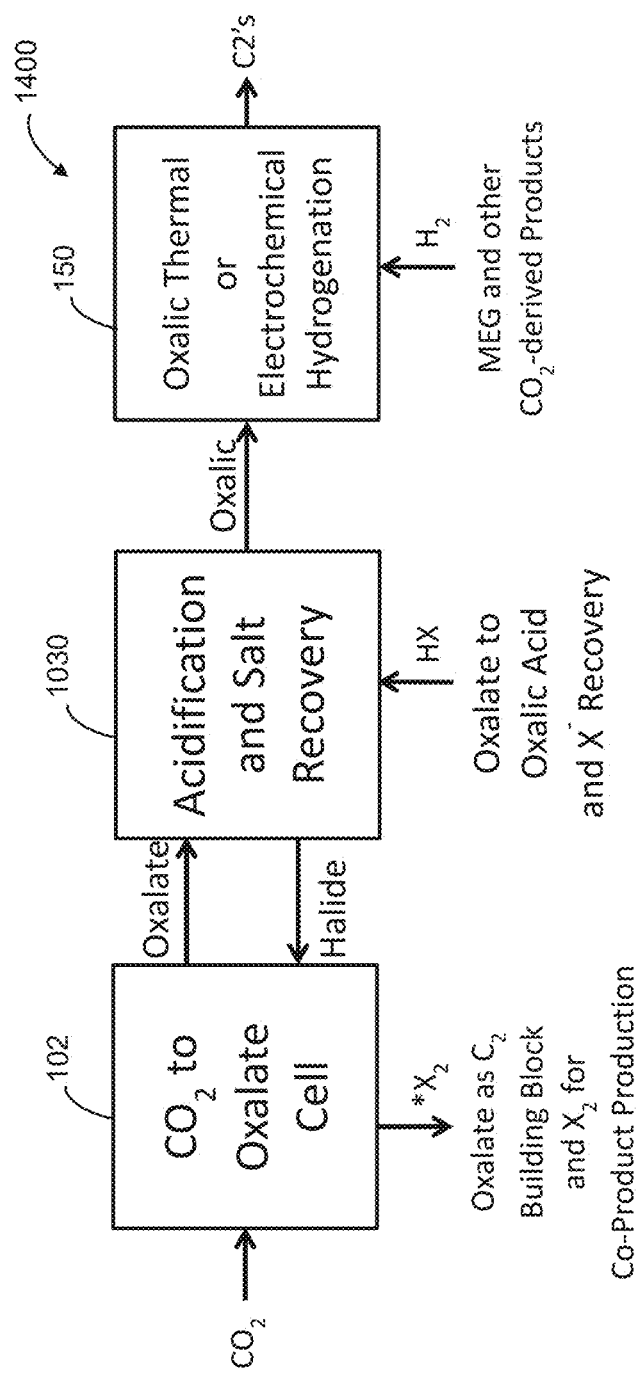
FIG. 14 is a schematic illustrating a system for the conversion of carbon dioxide to mono-ethylene glycol and other two-carbon products.

Referring to FIG. 14, a schematic illustrating a system 1400 for the conversion of carbon dioxide to mono-ethylene glycol and other two-carbon products. System 1400 may include electrochemical cell 102, acidification reactor 1030 and hydogenation device 150. Hydrogen halide may be reacted with carboxylate salt, such as an oxalate, from electrochemical cell 102 in an acidification reactor 1030 to produce a carboxylic acid, such as oxalic acid, and a halide salt. The halide salt may then be recycled to the electrochemical cell 102. The oxalic acid may be fed to hydrogenation device 150 where it is reduced to an oxalic acid reduction product, such as monoethylene glycol.

In addition to mono-ethylene glycol, systems 1000, 1100, 1200, 1300 and 1400 may produce a variety of multi-carbon chemicals. If oxalic acid is produced, it may be further reduced, for example, by electrochemical reduction, catalytic reduction or other reduction methods.

Electrochemical Cell Operating Conditions

Referring once again to electrochemical cell 102 as shown in at least FIG. 1, a solvent may be employed. The solvent may be a non-aqueous solvent or mix of solvents including propylene carbonate, ethylene carbonate, dimethyl carbonate, diethyl carbonate, dimethylsulfoxide, dimethylformamide, acetonitrile, ammonia, acetone, tetrahydrofuran, N,N-dimethylacetamide, dimethoxyethane, diethylene glycol dimethyl ester, butyrolnitrile, 1,2-difluorobenzene, γ-butyrolactone, N-methyl-2-pyrrolidone, sulfolane, 1,4-diaxane, nitrobenzene, nitromethane, acetic anhydride, alkanes, cycloalkanes, perfluorocarbons, linear carbonates, aromatics, benzene, toluene, aromatic derivatives, dichloromethane, chloroform, ethers, chlorobenzene, polyols, glymes, diglymes, triglymes, tetraglymes, alcohols, alkenes, trifluorotoluene, anisole, m-cresol, and ionic liquids to include those containing cations of the types: 1,3 dialkyimidazolium, N,N dialkylpyrrolidinium, and 1-alkyl-2,3-dimethylimidazolium, hexafluorophosphate, tetrafluoroborate, bis(trifluoromethanesulfonyl)imide, perfluoroalkylphosphate, or halide ions.

Many cathode materials may be used to effect the reduction of $CO_2$ to oxalate. Cathode materials may include Al, Au, Ag, Bi, Carbon (e.g. graphite), Cd, Co, Cr, Cu, $Cu_2O$, Cu alloys (e.g., brass and bronze), Fe, Fe alloys (e.g. Fe—Ti), Ga, Hg, In, Mo, Mo alloys (e.g. Mo—Ni), Nb, Ni, $NiCo_2O_4$, Ni alloys (e.g., Ni 625, NiHX), Ni—Fe alloys, Pb, Pb alloys, Pd alloys (e.g., PdAg), Pt, Pt alloys (e.g., PtRh), Rh, Sn, Sn alloys (e.g., SnAg, SnPb, SnSb), Ti, V, W, W alloys, Zn, stainless steel (SS) (e.g., SS 2205, SS 304, SS 316, SS 321), austenitic steel, ferritic steel, duplex steel, martensitic steel, Nichrome in various ratios (e.g., NiCr 60:16 (with Fe)), elgiloy (e.g., Co—Ni—Cr), and various Haynes International Inc. trade name nickel-cobalt alloys called Hastelloys, such as Hastelloy 276, Hastelloy C. Metal carbides as cathodes may also be used and could include iron carbide, molybdenum carbide, and chromium carbide.

A range of screens/meshes, non-woven materials, sintered metals, layered materials, foams, and gradients are suitable for use as cathode materials for the electrochemical cell. Cathodes may be coated with nanoparticles and nano-features through template electroplating, etching, and deposition. For example, nickel nanoparticles may be used to coat the cathode surfaces. An exemplary cathode may comprise of multilayers of 316 SS screen made of alternating layers of 400 mesh and 15 mesh stainless steel. A quantity of 12 or 22 micron non-woven 316 stainless steel, such as those available from Bekaert, may be used as a flow channel/electrical contact between the back plate and the layered mesh assembly. Another cathode may comprise corrugated screens with flow channels built in, wherein layers are spot welded or sintered together. The 3D electrode may be sintered or welded to suitable thickness 316 SS plate current distributor to make a complete integrated cathode assembly.

Cathode Structures

Suitable cathode structures also include the following forms:
  Metal plates
  Packed bed consisting of metal spheres or fibers
  Assembly of screens/meshes
  Metal foams
  Metal non-woven materials including needeled felts
  Sintered or partially sintered non-wovens
  Metal wools
  Layered materials
  Layered metal meshes or screens
  Welded layered meshes, such as those used as filtration media for PE extrusion
  Sintered metal fibers and powders
  Woven metal felts
  Other metal woven fibrous metals in various weaves or twills comprising various metal fiber sizes and thicknesses
  Metal coated carbon materials, such as nickel on carbon fibers, or metal coated ceramic fibers The electrochemical cell cathode may also comprise one or more cathode materials, one or more structure types, and with one or more combinations of metal and metal coating compositions. For example, the cathode may consist of a nickel fiber structure adjacent to the separator, and utilize a 304 SS structure towards the cathode backplate, which may be 304 SS or another metal alloy. The selection of the metal alloys and metallic coatings on the cathode is used to maximize the cathode reduction of carbon dioxide reaction. Cathode coatings on the cathode structure materials may be applied by electroplating, chemical vapor deposition (CVD) or other methods to all or various sections of the cathode structure. The cathode coatings may be metal or metal oxides, or converted to the metal or oxide by hydrogen reduction (metal oxide to metal) or thermal oxidation in air (formation of oxide coatings). The metals are the same group noted as the single metals or alloys specified. The coatings may also consist of multiple coatings of different layers of materials for providing stability.

Table 0 shows the effect of cathode materials on oxalate faradaic yield operated at constant current of −3.5 to −5 $mA/cm^2$. The working electrode, as listed, was immersed in a 0.2M TBABr solution in propylene carbonate saturated with $CO_2$. The reference electrode was a Ag wire. A three chamber electrochemical cell was used, with the compartments separated by porous glass frits. A two compartment electrochemical cell was used in some cases, the compartments separated by a Vicor® glass frit. The counter electrode was a Zn foil immersed in 0.2M tetrabutylammonium perchlorate (TBAP) in propylene carbonate.

Typically, the water content was 100-200 ppm at the start of the experiment and 120-150 at the end of the experiment. Experiments were typically run for 6 hrs. Approximately 10% Faradaic yield of oxalate was lost to the center compartment chamber when the three compartment cell was used, therefore true oxalate Faradaic yields are typically higher than listed.

TABLE 0

| Cathodes | Oxalate FY (%) |
| --- | --- |
| Stainless steel 2205 | 47-56 |
| Stainless steel 304 | 63-85 |
| Stainless steel 316 | 50-72 |
| Ni:Cr (60:16) | 40-53 |
| Ni:Cr (80:20) | 80-100 |
| Ni:Fe:Mo | 68-86 |
| Ni (99.994% purity) | 74-80 |
| Nickel | 58-67 |
| Mo | 72 |
| Fe:Co (80:20) | 68* |
| Co:Cr:Mo (60:30:10) | 0 |
| Hastelloy C Mesh | 28-35 |
| Co | 73-85 |
| W | 78-88 |
| Cu:Ni (55:45) | 31 |
| Fe:Mo (80:20) | 72* |
| Co:Cr:Mo (60:30:10) | 68* |
| Fe:Ni:B:Mo Metallic Glass | 6* |
| FeTi | 0* |
| FeB | 0* |
| $MoB_2$ | 2* |

TABLE 0-continued

| Cathodes | Oxalate FY (%) |
|---|---|
| Ni:Mo (80:20) | 37* |
| Mo:Ti (80:20) | 9* |
| W:Co (50:50) | 2* |
| WC:Co (94:6) | 0 |

*Represents the average of 2-3 independent experiments

In addition, the cathode material could be chemically modified to improve or enhance the cathode reaction efficiency and selectivity. For metallic surfaces, modification may include using thiols, primary amines, pyrrolidones, heterocyclic amines, and surfactants containing carboxylate groups, phosphonate groups, phosphine groups, and citrate groups. For oxide and carbide materials, silanes, diazomethanes, alkyl ammonium ions, cycloketones, cycloalkylidenes, and ionic liquid cations may be employed to modify the cathode surfaces.

To passivate stainless steel electrodes, electrodes of a required size are cut from bulk material. The electrodes are cleaned by polishing with alumina powder, followed by rinsing with deionized water, then dipping in acetone for approximately 2 minutes, followed by rinsing and sonication in deionized water. A 15 wt % citric acid in deionized water solution is prepared. Cleaned electrodes are immersed in 15 wt % solution of citric acid for approximately four hours at room temperature (25° C.). The electrodes are taken out of the solution, rinsed 3 times with deionized water and dried under argon. Treated electrodes may then be stored in closed glass vials until needed.

It is contemplated that the high surface area cathode/anode electrode may include the following characteristics, such as a preferred void volume ranging from 30% to 98%. The electrodes may include specific surface areas from 2 $cm^2/cm^3$ to 500 $cm^2/cm^3$ or higher. Surface areas also may be defined as total area in comparison to the current distributor/conductor back plate, with a preferred range of 2× to 1000× or more.

Table 00 shows the effect of corrosion inhibitors on oxalate faradaic yield when an electrochemical cell is operated at constant current of −3.5 $mA/cm^2$. The working electrode (304 SS) was immersed in a 0.2M TBABr solution in propylene carbonate saturated with $CO_2$. The reference electrode was a Ag wire. A three chamber electrochemical cell was used, with the compartments separated by porous glass frits. The counter electrode was a Zn foil immersed in 0.2M TBAP in propylene carbonate.

TABLE 00

| Cathode | Concentration (ppm) | Yield Oxalate (%) |
|---|---|---|
| Imidizole | 500 | 45.5 +/− 26% |
| 2-pyrrolydinone | 500 | 82.4 +/− 6.4% |
| EDTA | 500 | 82.2 |

Electrochemical Flow Cell Examples

An electrochemical cell was assembled with a 316 SS back conductor plate on the cathode side and a graphite back conductor plate on the anode side. A single layer of hydrophobic PVDF with a pore diameter of about 0.45 micron and thickness of about 150 micron was used as a separator between the cathode compartment and anode compartment. The cathode compartment contained a multi-layered high surface area 316 SS cathode. The cathode consisted of a non-woven fiber mat with a fiber diameter of 22 micron, which was in direct contact with the back plate. The thickness of the fiber mat was approximately 0.5 mm in its compressed state when installed in the cell. Between the non-woven material and the separator an assembly of layers of mesh was placed having two alternating opening sizes, fine (400×400) mesh with a thickness of 0.15 mm and an opening size of 0.0015 inches and an open area of 38%, and a coarse (15×15) mesh with a thickness of 0.4 mm and an opening size of 0.057 inches and an open area of 73%. In total eight layers of mesh were used. A 0.35 mm thick porous PTFE screen was placed between the separator and the cathode to minimize the risk of a short circuit. The anode compartment contained 4 layers of carbon cloth, the first of which was in direct contact with the separator. A sheet of porous glassy carbon, i.e., reticulated vitreous carbon with a pore density of 60 pores per inch, was placed between the layer and the other 3 carbon cloth layers. The thickness of a single carbon cloth layer and the RVC was 0.35 mm and 3.65 mm, respectively. Both electrode compartments were assembled in a zero-gap configuration, i.e., no open space left on either side of the separator.

The electrochemically active area of the cell was in the range of 50-100 $cm^2$. Electrolyte was fed to the respective electrodes via high density polyethylene flow plates having flow channels with a circular cross section. The flow entered the active electrode compartment on the bottom of the cell and was directed upward, parallel to the separator.

Example 1

PC Room Temperature Operation

A flow cell experiment was run using propylene carbonate with 0.5 M TBABr as the electrolyte. The anolyte and catholyte were purged with nitrogen and sparged with carbon dioxide, respectively. The current density was 75 mA/cm2 and was conducted at room temperature (25° C.). The flow rate for the catholyte was 150 ml/min and for the anolyte was 100 ml/min. The cell voltage was about 15V. The current efficiency was approximately 30% while the highest oxalate concentration was 0.37% by weight (3700 ppm).

Example 2

PC High Temperature Operation

A flow cell experiment was executed using propylene carbonate with 0.5 M TBA-Br and 10 mM benzonitrile as the electrolyte. The anolyte and catholyte were purged with nitrogen and sparged with carbon dioxide, respectively. The current density was 75 $mA/cm^2$ and was conducted at 60° C. The flow rates for both the anode and cathode were 1.1 L/min. The cell voltage was between 6.8 and 7 volts. The current efficiency was between 15% and 30%. The highest oxalate concentration was 0.24% by weight (2400 ppm).

Example 3

ACN as a Anolyte/Catholyte Solvent

A flow cell experiment was performed using acetonitrile as a solvent with 0.75 M TBABr as the electrolyte. The anolyte and catholyte were purged with nitrogen and sparged with carbon dioxide, respectively. The current density was 75 mA/cm2. The run was conducted at ambient temperature and pressure. The anode and cathode flow rate was 1.1 L/min. The cell voltage was in the range of 5.7-6.5 V. The current efficiency was 50% for oxalate and 40% for the anolyte tribromide generation. The highest oxalate concentration was 2.5% by weight (25,000 ppm).

Example 4

Nickel Cathode

In an embodiment of the disclosure, it has been found that nickel cathodes may improve cell voltages. When using stainless steel cathodes, voltages of 5.5V at 75 mA/cm2 are typically observed. With thick Ni cathodes voltages of about 5 V or less are observed. (Table 1). As shown in Table 2, a thin electrode configuration in conjunction with Ni brings the voltage to about 4.1V. Both tests were executed with a PTFE separator (0.45 micron pore size). A PVDF separator (0.1 micron pore size) may also be used. A test of a PTFE separator using a stainless steel cathode resulted in yields similar to what is shown on Table 1 (about 70% for the first hour of the run, see Table 3).

The nickel cathode may be formed as a mesh including either 2 or 4 layers of mesh bonded together. To form the cathodes used in the experiments, three to five pieces of mesh were cut (depending on cathode thickness), which were then folded once, yielding 6 or 10 layers of bonded mesh in the cathode compartment. The current collector plate may also comprise nickel.

TABLE 1

Thick Nickel Cathode Run With PTFE Separator
Cell Configuration: 5x double layer (folded) of multi-layer Ni-mesh
[85 × 70 0.006], 1 PTFE Screen, 0.45 micron PTFE hydrophilic
separator (rough side facing anode.
Description: Run with 0.75M TBA-Br in ACN thick electrode
configuration (¼")

| Time (min) | I Current (Amperes) | Cell Voltage (Volts) | Oxalate Concentration mg/L | Oxalate Faradaic Yield % At Time Intervals |
|---|---|---|---|---|
| 0 | 7.7 | 5.06 | 593.60 | |
| 30 | 7.7 | 4.74 | 2953.98 | 77.9% |
| 60 | 7.7 | 4.82 | 5293.01 | 75.2% |

TABLE 2

Thin Nickel Cathode Run With PTFE Separator
Cell Configuration: 3x double layer (folded) of multi-layer Ni-mesh
[85 × 70 0.006], 0.45 micron PTFE hydrophilic separator
(rough side facing anode)
Description: Run with 0.75M TBA-Br, thin electrode configuration (⅛")

| Time (min) | I Current (Amperes) | Cell Voltage (Volts) | Oxalate Concentration mg/L | Oxalate Faradaic Yield % At Time Intervals |
|---|---|---|---|---|
| 0 | 7.7 | 4.36 | 413.52 | |
| 30 | 7.7 | 4.14 | 2356.78 | 64.4% |
| 60 | 7.7 | 4.05 | 4017.87 | 54.4% |
| 90 | 7.7 | 4.09 | 5543.32 | 49.5% |
| 120 | 7.7 | 4.06 | 6839.26 | 42.2% |

TABLE 3

Stainless Steel Cathode with PTFE separator
Cell configuration: PTFE, hydrophilic PTFE separator.
(0.45 µm), C cloth
Run Description: Run with 0.75M TBABr in ACN, 0.45M hydrophilic
PTFE separator

| Time (min) | I Current (Amperes) | Cell Voltage (Volts) | Oxalate Concentration mg/L | Oxalate Faradaic Yield % At Time Intervals |
|---|---|---|---|---|
| 0 | 7.7 | 6.11 | 122.27 | |
| 30 | 7.7 | 7.04 | 2139.99 | 69.0% |
| 60 | 7.7 | 6.74 | 4116.19 | 67.1% |
| 90 | 7.7 | 6.82 | 5979.04 | 55.0% |
| 120 | 7.7 | 6.95 | 7738.92 | 56.8% |

It is further contemplated that additives may be utilized to increase salt solvation and conductivity in electrochemical cell 102. Additives may be used to enhance salt solvation and may also increase conductivity in an additive or co-solvent role. Additive concentrations may range from ppm levels to 100% by weight. In general, the additive or multiple additives will be used in addition to one or more solvents listed above. Additives may include carbonates such as dimethyl carbonate, ethylmethyl carbonate, diethyl carbonate, dipropyl carbonate, and dibutyl carbonate. Carbonates with other akyl groups are also claimed. In addition phosphates such as benzyl phosphate, denzyl dimethyl phosphate, allyl phosphate, dibenzyl phosphate, and diallyl phosphates may be used. Some organic sulfates such as methyl benzyl sulfate, ethylbenzylsulfate, diallyl sulfate, propyl allyl sulfate and butylallylsulfate may also be used as additives to increase the conductivity.

Additives may also include the ionic liquids listed previously as well as their mixtures and other variations. Surfactants may also be used. Crown ethers may be added to increase the solvation of hard cations such as $Li^+$, $Na^+$, and $K^+$. The crown ether employed for $Li^+$, $Na^+$ and $K^+$ are 12-crown-4, 15-crown-5, diphenyl-18-crown-6, and 18-crown-6, respectively. Similarly, cryptands may also be used to increase solvation for hard cations. These include 2.2.2-cryptand, 2.2.1-cryptand, 2.1.1-cryptand, 2.2.2B-cryptand, and 5-decyl-4,7,13,16,21-pentaoxa-1,10-diazabicyclo(8.8.5)tricosane. Larger cryptands and those available from EMD Millipore under the trade name of Kryptofix may also be employed.

Anion acceptors may also be used to increase solvation of the halide anion. These include borane and boroxine derivatives to include, but not limited to, tris(isopropyl)borane and trimethoxyboroxin.

Glymes may increase conductivity, increasing ion solvation and also may lower solution viscosity. Glymes include glyme, diglyme, triglyme, and tetraglyme as well other glyme variations. Metal nanoparticles, zwitterions, and micelles or reverse micelles could also be employed.

A range of organic homogenous catalysts, capable of being reduced to a radical anion at the cathode interface and transfering an electron to $CO_2$ may be used. These include, but are not limited to, benzophenone methyl 4-methyl-3-nitrobenzoate, tetracyanoquinodimethane, cyclooctatetraene, diphenylethanedione (benzil) and benzonitrile.

Anion catalysts to help effect the oxidation of halide ions to halogens could include nitroxides, nitronyl nitroxides, azephenylenyls, perchlorophenylmethyl radicals, TEMPO (2,2,6,6-Tetramethyl-1-piperidinyloxy) and tris(2,4,6-trichlorophenyl)methyl radicals. The radical of each compound may also be used. Other catalysts could include succinimide, N-bromosuccinimide, or other imides.

The minimum voltage for the cathodic half cell may be −0.71 V vs. SCE. The operating cathodic half cell voltage is usually between −1.2 and −3 V vs. SCE. The minimum voltage for the anodic half cell is 0.83 V vs. SCE. The operating anodic half cell voltage is usually between 1 and 3 V vs. SCE. The overall voltage for the complete cell is usually between 2 and 20 V.

Catholyte operating temperature may be in a range of −10 to 240° C., and more preferably 5-60° C. The lower temperature may be limited by the electrolytes used and their freezing points. In general, the lower the temperature, the higher the solubility of $CO_2$ in the solution phase of the electrolyte. Higher carbon dioxide concentrations may help in obtaining higher conversion and current efficiencies. The drawback is that the operating electrolyzer cell voltages may be higher, so there is an optimization that would be done to produce the chemicals at the lowest operating cost. Anolyte operating temperature operating temperature may be in a range of −10 to 240° C., more preferably 5-60° C.

Operating the electrochemical cell catholyte at a higher operating pressure allows more dissolved $CO_2$ to dissolve in the solvent. Typically, electrochemical cells may operate at pressures up to about 20 to 30 psig in multi-cell stack designs, although with modifications, they could operate at up to 100 psig. The electrochemical cell anolyte would also need to be operated in the same pressure range to minimize the pressure differential on the membrane separating the two electrode compartments. Special electrochemical designs are required to operate electrochemical units at higher operating pressures up to about 60 to 100 atmospheres or greater, which is in the liquid $CO_2$ and supercritical $CO_2$ operating range.

In another embodiment, a portion of the catholyte recycle stream may be separately pressurized using a flow restriction with backpressure or using a pump, with $CO_2$ injection, such that the pressurized stream is then injected into the catholyte region of the electrochemical cell, and potentially increasing the amount of dissolved $CO_2$ in the aqueous solution to improve the conversion yield.

The catholyte cross sectional area flow rate range may be 2-3,000 gpm/ft$^2$ or more (0.0076-11.36 m$^3$/m$^2$) and may include a flow velocity range of 0.002 to 20 ft/sec (0.0006 to 6.1 m/sec).

The electrochemical cell design may include Zero-Gap, flow-through with a recirculating catholyte electrolyte with various high surface area cathode materials. Additional designs may include flooded co-current packed and trickle bed designs with the various high surface area cathode materials. Bipolar stack cell designs and High pressure cell designs may also be employed for the electrochemical cells.

The operating cell voltages for the electrochemical cells disclosed in the embodiments in this disclosure may range from about 1.0 to about 20 volts depending on the anode and cathode chemistry employed in addition to the cell operating current density. The operating current density of the electrochemical cells may range from 5 ma/cm$^2$ to as high as 500 ma/cm$^2$ or more.

For bromine and iodine anode oxidation chemistry, carbon and graphite are particularly suitable for use as anodes. The anode may include electrocatalytic coatings applied to the surfaces of the base anode structure. For the oxidation of HBr, acid anolytes, and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar electrochemical cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as precious metals such as platinum and precious metal oxides such as ruthenium oxide in addition to other transition metal oxide catalysts.

The electrochemical cell anode may comprise flat carbon/graphite plates, RVC (reticulated vitreous carbon) foams, carbon cloth, carbon felts/tissue may be used. Carbon cloth may be used as an electrically conductive material to ensure good electrical contact with the anode back plate.

Suitable Anode structures include:
Plates (carbon/graphite/graphene)
RVC
Carbon cloth
Woven with and without activated carbon layer
Various loadings of PTFE
Carbon tissue
Carbon felts
Carbon fibers
Conductive diamond films
Iridium oxide on titanium
Ruthenium oxide plated or deposited onto a carbon felt or carbon cloth as a catalyst
Graphene Cation ion exchange type membranes may be preferred as separators for 120 in embodiments for electrochemical cell 102, especially those that have a high rejection efficiency to anions and allowing cations to pass. Examples of these membrane types having a fluorinated hydrocarbon backbone are perfluorinated sulfonic acid based cation ion exchange membranes such as DuPont Nafion® brand unreinforced types N117 and N120 series, more preferred PTFE fiber reinforced N324 and N424 types, and similar related membranes manufactured by Japanese companies under the supplier trade names such as Flemion®.

Other multi-layer perfluorinated ion exchange membranes used in the chlor alkali industry have a bilayer construction of a sulfonic acid based membrane layer bonded to a carboxylic acid based membrane layer, which efficiently operates with an anolyte and catholyte above a pH of about 2 or higher. These membranes have a much higher anion rejection efficiency. These are sold by DuPont under their Nafion® trademark as the N900 series, such as the N90209, N966, N982, and the 2000 series, such as the N2010, N2020, and N2030 and all of their types and subtypes.

Hydrocarbon based membranes, which are made from of various cation ion exchange materials may also be used if the anion rejection is not as critical, such as those sold by Sybron under their trade name Ionac®, AGC Engineering (Asahi Glass) under their Selemion® trade name, and Tokuyama Soda among others on the market. These hydrocarbon based membranes may be specially prepared from ion exchange materials that are bonded together in a suitable bonding matrix such as polyethylene, polypropylene, and polyvinylchloride (PVC) as examples. Other membrane types may use a microporous separator and have an impregnated ion exchange material that may be chemically bonded or adhered to the separator, such as Nafion infused or bonded to a PVDF or PTFE separator, or other ionic materials, such as ionic liquids that can be used to prepare solid gel-type membranes and the like, as long as they are chemically suitable with the liquid phase solutions contemplated in electrochemical cell 102. All of the membrane and separator materials suggested or described in this invention may also be employed in the various other electrochemical cells designs and methods disclosed in this application which are non-aqueous or aqueous based.

Microporous separators may also be employed in some electrochemical system options such as microporous PVDF (polyvinylidiene difluoride) based, PTFE (polytetrafluoroethylene), or glass fiber based materials as well as commercial diaphragms available for the chlor alkali industry. These microporous separators may also be prepared and constructed in various other plastics or polymers or their combinations that are chemically suitable for the solvent and salts employed in electrochemical cell 102. In addition, multiple layers may be employed using one or more separator types. In addition, ceramic based porous separators, which may be in flexible sheet forms, may be employed, for example aluminum oxide (alumina) based, silicon oxide based, and zirconium oxide based and their various combinations in addition to boron carbides and the like.

Another suitable membrane separator material, being marketed by CeramHyd, under the trade name CERAPEM, employs an activated boron nitride in a PTFE matrix may also be suitable for some of the various electrochemical cells described in this disclosure.

Alternative ceramic based membranes may also be employed as separators, especially those that may conduct and operate at the low temperatures, 5° C. to 200° C., for the various electrochemical cells that may be used in this disclosure. These membranes may be selective in various cations such as alkali metal or even hydrogen ions.

Suitable electrochemical separators include commercially available PVDF (polyvinylidene difluoride) filtration material with a 0.1-0.45 micron pore size, available with a thickness of approximately 145 microns thick may be used. Such as material is manufactured by Meissner and distributed by Tisch scientific. Lithium ion battery materials, for example from W. L. Gore and Associates (polytetrafluoroethylene PTFE based), may also be used. Other lithium battery battery separator materials may include inorganic compounds tomprovide dimensional stability The selection of the separator is based on the compatibility of the separator or membrane with the solvent(s) selected and stability to the anode reaction product.

Other separator materials that may be used in the electrochemical cell include:
Polymeric porous separators for lithium ion batteries and filtration processes
  a. PVDF, PTFE, Polyolefin, HDPE, PEEK (polyether ether ketone), nylon
  b. Composite polymer matrix with inorganic particle and fiber fillers
  c. Fiber (woven polymer) supported polymers Inorganic filtration materials
  a. Ceramics comprising silica, alumina, titania, and zirconia in a woven or nonwoven form, with and without binders
  b. Partially sintered glass fiber and and ceramic materials
Perfluorinated ionomers
  a. Nafion® brand perfluorinated sulfonic acid based membranes and cation exchange related membrane materials
  b. Composite perfluorinated ionomers which incorporate inorganic particles or fibers in the ionomer matrix
Combination hybrid Organic-Inorganic membranes having an inorganic within a polymer matrix Partially fluorinated and hydrocarbon-based ionomers (e.g., PEEK-S)
Solid state ion conductors and composites including these materials
  a. E.g., ceramic membrane composed of boron nitride with PTFE matrix
Hydrocarbon based membranes, which may be fabricated from ion exchange resin materials The electrochemical cells described herein may be independently configured in three ways: Three major flow configurations may be used:
  Flow-in (flow inside a 3D electrode structure parallel to the separator)
  Flow-by (flow in a plenum/open mesh along the 3D electrode surface parallel to separator)
    flow along either the side facing the separator or the side facing the back plate
  Flow-thru (flow through the electrode, perpendicular to separator)
    flow towards and away from separator Referring once again to FIGS. 1 and 12, electrochemical reduction cell 130, also referred as the anolyte recovery electrochemical cell, may be similar to electrochemical cell 102. Electrochemical reduction cell 130 may include a first region and a second region. First region and second region may refer to a compartment, section, or generally enclosed space, and the like without departing from the scope and intent of the present disclosure. First region 116 may include a cathode. Second region 118 may include an anode. Electrochemical reduction cell 130 may reduce a halogen or trihalide anion 115 to HX 132 at the cathode and oxidize water 134 at the anode, producing oxygen ($O_2$) and liberating hydrogen ions ($H^+$) to be transferred across the membrane of the electrochemical reduction cell 130 to generate the HX 132.

Electrochemical reduction cell 130 may produce an acid, such as HX, that may be used to acidify oxalate and allow the recycle of the halogen or multivalent material for reuse to electrochemical cell 102. There are several ways to configure the electrochemical cell 130. A two region electrochemical reduction cell, including a catholyte region and an anolyte region separated by a cation ion exchange membrane may be used. The anode reaction may be the oxidation of water in an inorganic acid producing hydrogen ions and oxygen. The hydrogen ions may then pass through the membrane into the cathode compartment. In the cathode compartment, the feed of halogen, such as $Br_2$, may then be reduced at the cathode to bromide ions (Bo, and then combine with the hydrogen ions to produce HBr. The cathode reaction may require a high surface area structure to efficiently convert the $X_2$ halogen or $X_3^-$ halide anion to the HX acid. An aqueous or non-aqueous catholyte with the addition of water may also be used. For instance, the non-aqueous solvent from the anode region 118 of electrochemical cell 102 may be fed directly into electrochemical cell 130 for bromine reduction, or the bromine might be separated from the anolyte of electrochemical cell 102 and introduced to the catholyte of electrochemical cell 130 for reduction. The HX may then passed on to the next reactor the acidification reactor 1030 to acidify and convert alkali metal oxalate or tetraalkylammonium oxalate to oxalic acid.

Referring once again to FIG. 2, electrochemical cell 210, also referred as an electrochemical acidification cell, is configured to convert oxalate to oxalic acid. Hydrogen ions may be generated in the anode, or anolyte region 118 and pass through a central ion exchange region 212 bounded by two cation ion exchange membranes 214, 216. The M-oxalate solution is passed through the ion exchange compartment 212 where the M-cations are exchanged for the hydrogen ions, producing oxalic acid, and the M-cations pass through the adjoining second cation membrane 214 into the catholyte region 116. In the catholyte region, the $X_2$ or $X_3^-$, such as bromine or tribromide, is reduced at the cathode 122, forming $X^-$, such as bromide, which combines with the M-cations to form an MX reduced product. The MX 117 may then be recycled to electrochemical cell 102.

Electrochemical cell 210 may include three regions, a first region 116 such as a catholyte region, a second region 118 such as an anolyte region and a third region 212 such as central ion exchange region by two cation exchange membranes on each side. The second region 118 includes an anode 124 suitable to oxidize water. In a preferred implementation, the anode 124 is a titanium anode having an anode electrocatalyst coating which faces the adjacent cation exchange membrane 216. The first region 116 includes a cathode 122 suitable to reduce water and to generate an alkali metal hydroxide.

In a preferred implementation, hydrogen ions ($H^+$) or protons are generated in the second region 118 a potential and current are applied to the electrochemical cell 210. The hydrogen ions ($H^+$) or protons pass through the adjacent cation exchange membrane 216 into the central ion exchange region 212. An alkali metal oxalate, or tetraalkylammonium oxalate, stream is preferably introduced to the electrochemical cell 210 into the bottom of the central ion exchange region 212, where the hydrogen ions ($H^+$) or protons displace the ions (e.g., lithium or tetraalkylammonium ions) in the product stream to acidify the stream and produce the oxalic acid 144. The displaced cations may pass through the adjoining cation exchange membrane 214 into the first region 116 to combine with hydroxide ions ($OH^-$) formed from water reduction at the cathode 122 to form a hydroxide, such as lithium or tetraalkylammonium hydroxide.

The central ion exchange region 212 may include a plastic mesh spacer (not shown) to maintain the dimensional space in the central ion exchange region 212 between the cation exchange membranes 214, 216. In an embodiment, a cation ion exchange material may be included in the central ion exchange region 212 between the cation exchange membranes 212, 214. It is contemplated that the cation ion exchange material may increase electrolyte conductivity in the ion exchange region solution.

The second region 118 generally may include an anode feed stream that includes an acid anolyte solution, such as a sulfuric acid solution, or an HX solution, and may produce a gaseous oxygen product 222. A deionized water source 220 and an acid make-up source may maintain anolyte acid strength and volume for the anode recycle loop, not shown.

The first region 116 may include a cathode feed stream that includes water and may include an alkali metal hydroxide that circulates through the catholyte recycle loop. The reaction products, which may include an alkali metal hydroxide and hydrogen gas, may exit the first region 116.

It is contemplated that electrochemical cell 210 may include a catholyte disengager configured to process a cathode exit stream into a hydrogen stream, a catholyte recycle stream, and a catholyte overflow stream which may include hydroxide. The hydrogen stream may be vented from the catholyte disengager. The catholyte recycle stream preferably includes an alkali metal hydroxide, such as lithium hydroxide, or tetraalkylammonium hydroxide. The catholyte stream may have a deionized water source to control the concentration of the hydroxide.

It is contemplated that electrochemical cell 210 may include a variety of characteristics to improve performance. High surface area cathode structures are preferred. Carbon materials such as high surface area carbon and graphite felts may be employed for the reduction of the halogen. The cathode may include preferred void volume, ranging from 30% to 98%, a specific surface area from 2 $cm^2/cm^3$ to 500 $cm^2/cm^3$ or higher. The surface area also can be defined as total area in comparison to the current distributor/conductor back plate, with a preferred range of 2× to 1000× or more.

For the anode reaction with the generation of oxygen, electrocatalytic coatings of precious metals, such as platinum, and precious metal oxides such as ruthenium and iridium oxides and their combinations as metals and oxides on valve metal substrates such as titanium, tantalum, or niobium are suitable. As described herein, high surface area anode structures may also be used.

Dilute inorganic acids may be used as the anolyte, such as HX acids or sulfuric acid or phosphoric acid with the addition of water into the anolyte compartment to compensate for water losses as needed.

Referring once again to FIG. 3, anion exchanger 140, also referred as an acidification and separation unit, is configured to recycle salt to electrochemical cell 102 and to acidify oxalate salt to oxalic acid 144. In one embodiment, anion exchanger 140 may include an anion exchange column. Oxalate salt 113 in solution may be passed through the column and oxalate salt may adsorb to the column material, causing another anion to desorb and combine with the cation(s) from the oxalate to form salt or salts. The anion would typically be the conjugate base of an acid. When an acid solution is introduced to the column, the oxalate may be desorbed as oxalic acid and the conjugate base of the acid, such as $Cl^-$, $Br^-$, or $I^-$ is adsorbed to the column. The overall effect may be to achieve acidification of oxalic acid and separation of the oxalic acid from the salt used in electrochemical cell 102. The oxalic acid 144 may then be utilized as a product or further processed to another chemical. The salt used in the first electrochemical cell may be recycled so there may be few byproducts of the process.

The separation, acidification, and solvent transfer process of anion exchanger 140 may be effected by a basic anion exchange resin. An embodiment of the process is illustrated in FIG. 4, which includes absorbing oxalate ions using a basic anion exchange resin and desorbing the oxalate with a desired mineral acid. Referring to FIG. 5, a more detailed series of flow diagrams illustrating the oxalate absorption, water rinsing, regeneration, and solvent rinse steps is shown.

Step 1: The process starts with primary inputs of solvent mix A which may be either a single solvent or mixture of solvents, oxalate ions of the form $M_nC_2O_4$ where M is a cation that is monovalent or divalent, and X is an anion such as $Cl^-$, $Br^-$, or $I^-$. The input solution may be passed through a strong base ion exchange resin in the $X^-$ form; oxalate is absorbed by the anion exchange resin, liberating $X^-$. The effluent recycle stream may include solvent A and salt $M_nX_m$.

Step 2: When the ion exchange bed is exhausted and oxalate begins to break through the bed, the bed may be drained and rinsed with water. Rinsing may remove solvent A from the resin bed.

Step 3: The bed may be regenerated with an aqueous HX solution of sufficient concentration to cause the desorption of oxalate ions. Regeneration may result in a mixed stream of oxalic acid and HX in water.

Step 4: After regeneration, the bed may be drained and rinsed with solvent A. The process may now be restarted by returning to Step 1.

In this embodiment, the oxalate salt may be removed from one solvent and re-dissolved as oxalic acid in an aqueous phase. This is specifically useful coupled with the electrochemical hydrogenation cells 620, 630 of FIG. 6 which may which require oxalic acid in an aqueous electrolyte.

In a different embodiment, a solvent used in the anion exchange process as the regenerate could be solvent A or another non-aqueous solvent. In this embodiment, oxalic acid may be re-dissolved in solvent A or another non-aqueous solvent followed by thermal catalytic hydrogenation of oxalic acid as shown in thermal hydrogenation device 610 of FIG. 6. Catalytic hydrogenation of oxalic acid may be performed in either aqueous or non-aqueous solution.

Figure 24:
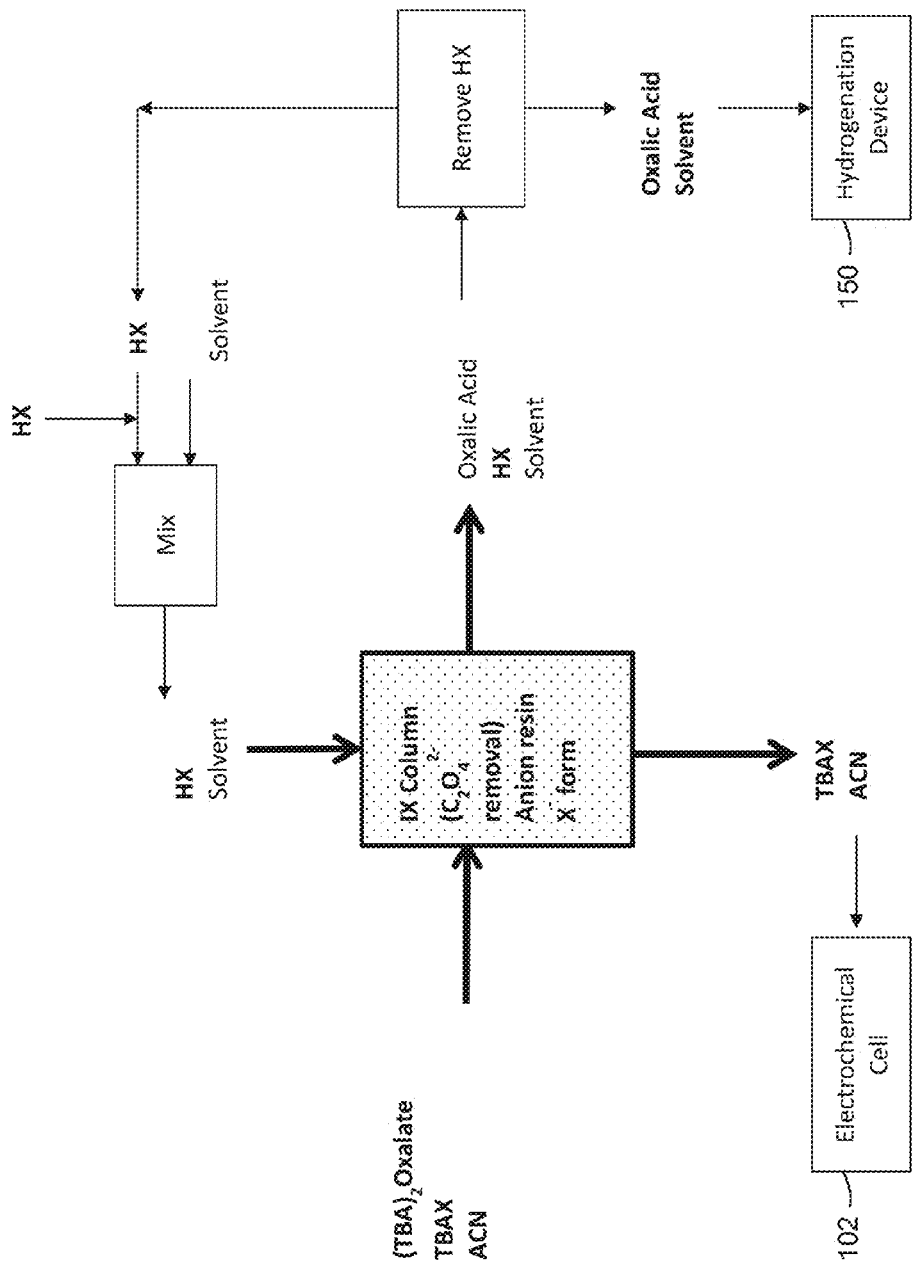
FIG. 24 is a schematic illustrating a process for the conversion of an oxalate salt to oxalic acid.

In another embodiment, the oxalate salt may be precipitated from the non-aqueous phase recovered from electrochemical cell 102 by using a combination of a cation and solvent to give low solubility oxalate salt. This may be described as shown in FIG. 24. After isolation of the salt it may be dissolved in an aqueous solution and acidified with HX. In order to recover the MX for reuse, an appropriate solvent may be added to the aqueous solution of oxalic acid and MX to cause MX precipitation. The MX may be dried and recycled, and a second solvent separated from the aqueous phase to recover the second solvent. This may provide oxalic acid in aqueous solution for use in electrochemical hydrogenation cells 620, 630 of FIG. 6B and FIG. 6C.

Figure 23:
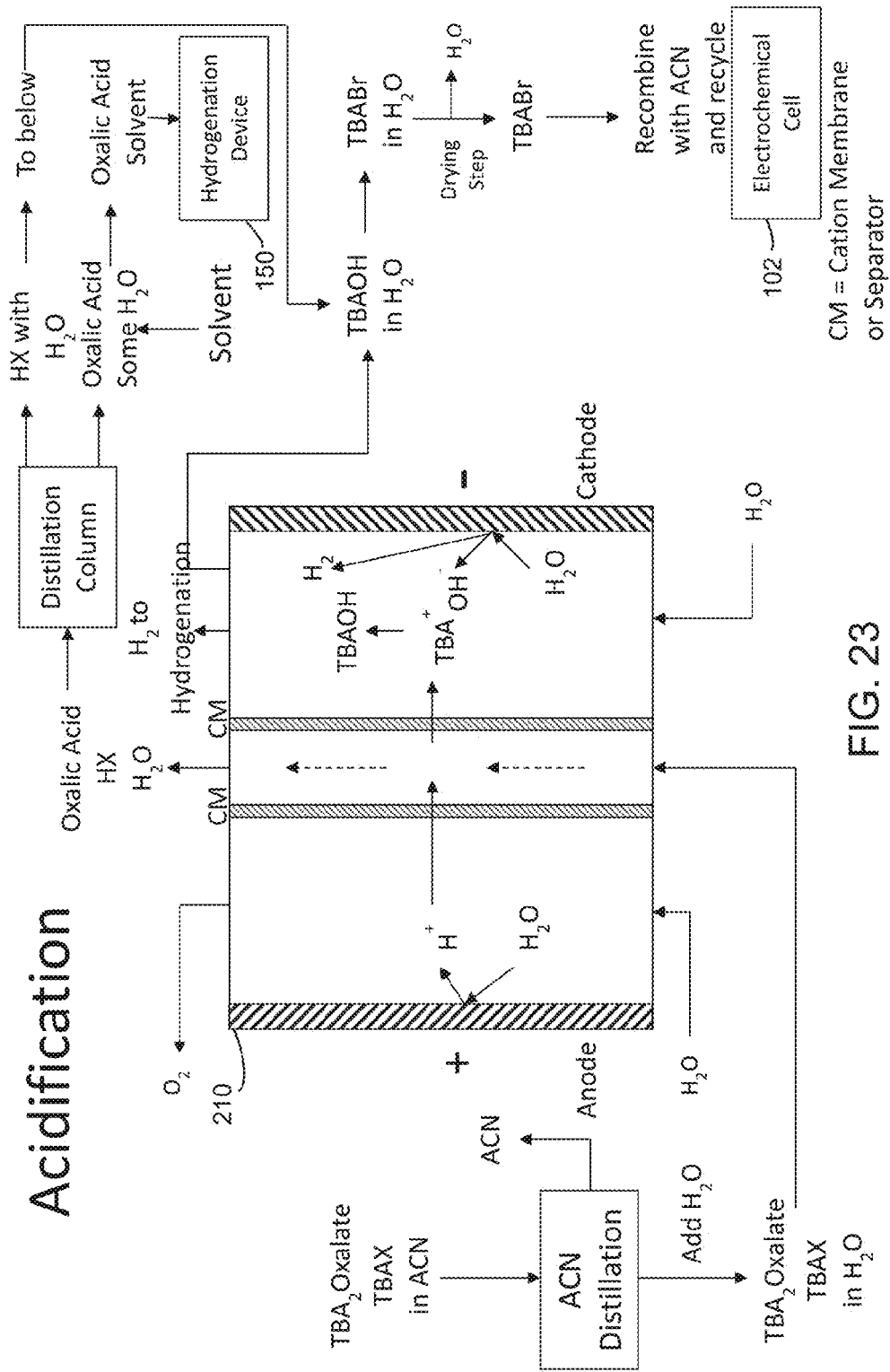
FIG. 23 is a schematic illustrating an electrochemical acidification cell and a process for the conversion of oxalate to oxalic acid.

In another embodiment, the oxalate salt may be precipitated from the non-aqueous phase from electrochemical cell 102 by using a combination of a cation and solvent to give a low solubility oxalate salt. After isolation this salt may be dissolved in an aqueous solution and acidified with HX. Using liquid-liquid extraction, oxalic acid may be extracted into a second phase, as shown in FIG. 23. The extraction solvent may be separated from the oxalic acid and recovered, leaving oxalic acid to be re-dissolved in an aqueous solution. The MX left in the aqueous phase may be dried and recycled, for example to electrochemical cell 102.

Oxalic acid may be recovered as a saleable product or may be further reduced to more reduced $C_2$ or $C_4$ chemicals. The methods of reduction may involve either thermal catalytic hydrogenation or electrochemical reduction as shown in FIGS. 6A, 6B and 6C.

It is contemplated that hydrogenation device 150 as depicted in FIGS. 1-3 and 10-14 may be implemented as one of devices 610, 620, 630 as shown in FIGS. 6A, 6B, 6C, and 16. Referring specifically to FIG. 6A, thermal catalytic hydrogenation device 610 may be configured to retain oxalic acid in a non-aqueous solvent through the anion exchanger 140. Oxalic acid may also be in an aqueous solution. It may then be hydrogenated to a more reduced chemical such as glyoxylic acid, glycolic acid, glycolaldehyde, ethylene glycol, ethanol, acetaldehyde, acetic acid, ethane, ethylene, or glyoxal via the addition of heat, pressure, and/or introduction of a hydrogenation catalyst. $C_4$ chemicals may also be produced. For instance, oxalic acid in propylene carbonate might be pumped into a high-pressure reactor, pressurized with $H_2$, and heated in the presence of a supported hydrogenation catalyst. Ethylene glycol, or glycolic acid, may then be recovered upon completion of the reaction.

The overall equation for hydrogenation device 610 for $C_2$ products is:

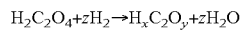

$$H_2C_2O_4 + zH_2 \rightarrow H_xC_2O_y + zH_2O$$

For hydrogenation device 610, catalysts may include cobalt, copper, ruthenium, ruthenium dioxide, cobalt nickel alloys, nickel, Pt group metals, rhenium, copper chromite, zinc copper chromite, barium chromite, ammonium copper chromate, zinc chromate, Raney nickel, manganese chromate, and alloys of copper and the other metals listed. These catalysts may be supported on carbon, alumina, silica, diatomaceous earth, pumice, zeolites, or molecular sieves.

Promotors such as trivalent phosphorus compounds, ammonia, and alkylammonium salts may be employed. The operation may be either batch mode or continuous flow mode with either a fixed bed or a fluidized bed. Contact time of the reactant with the catalyst may be greater than 0.1 seconds.

The reactant for hydrogenation device 610 may be either oxalic acid, an oxalate salt, oxalic acid dihydrate, or the diester of oxalic acid. The $H_2$ pressure may be greater than 10 atmospheres and may be between 10-1000 atmospheres. The $H_2$ concentration may be in excess of the stoichiometric amount required to reduce oxalic acid to ethylene glycol. The temperature may be between 50° C. to 500° C., preferably less than 150° C. to avoid thermal decomposition of oxalic acid.

It is contemplated that the oxalic acid carrier may include a non-aqueous solvent such as those which may be used in electrochemical cell 102. In one embodiment, the oxalate salt will be acidified where the solvent could include propylene carbonate or acetonitrile. The cations liberated from the oxalate salt may be recycled to the catholyte region of an electrochemical cell, while the oxalate salt is acidified to oxalic acid in a non-aqueous stream. A stream comprising oxalic acid, a non-aqueous solvent, with or without a further salt, may be directed to the hydrogenation device 610 for hydrogenation.

The hydrogenation of oxalic acid may take place in water, a non-aqueous solvent, or in the gas phase. Oxalic acid may also be contacted with an alcohol, such as methanol or ethanol or butanol, to form esters to include dimethyl oxalate or diethyl oxalate or dibutyl oxalate. These esters may then be hydrogenated, which allows for the production of higher order products and the recovery of the alcohol.

Figure 15:
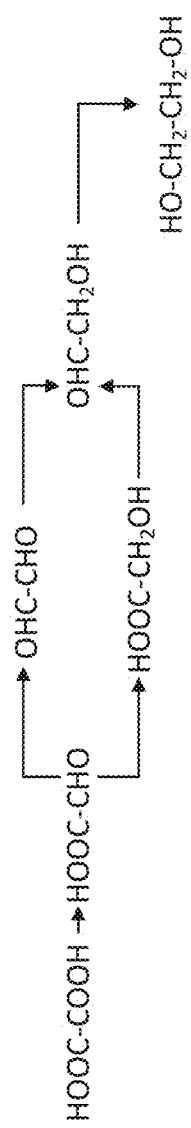
FIG. 15 is a schematic illustrating the possible intermediates in the catalytic hydrogenation of oxalic acid to mono-ethylene glycol.

Hydrogenation of the oxalic acid mono and diesters is well reported in the literature and is traditionally carried over supported NiO/CuO catalysts in both gas and in liquid phase. The liquid phase hydrogenation of oxalic acid may take place through a series of intermediates, as shown in FIG. 15, leading to ethylene glycol. According to this reaction scheme, the hydrogenation of oxalic acid generates glyoxylic acid, which may be converted to either glyoxal or glycolic acid, and further hydrogenation of either of these two intermediates generates the glycolic aldehyde, the glycolic aldehyde may be converted to ethylene glycol.

It is contemplated that the electrochemical hydrogenation cells 620, 630 of FIGS. 6B and 6C may be suitable for hydrogenation of oxalic acid to glyoxylic acid. It is further contemplated that thermal catalytic hydrogenation device 610 may be suitable for hydrogenation of oxalic acid to glycolic acid as a first possible product or ethylene glycol as a second possible product.

Figure 16:
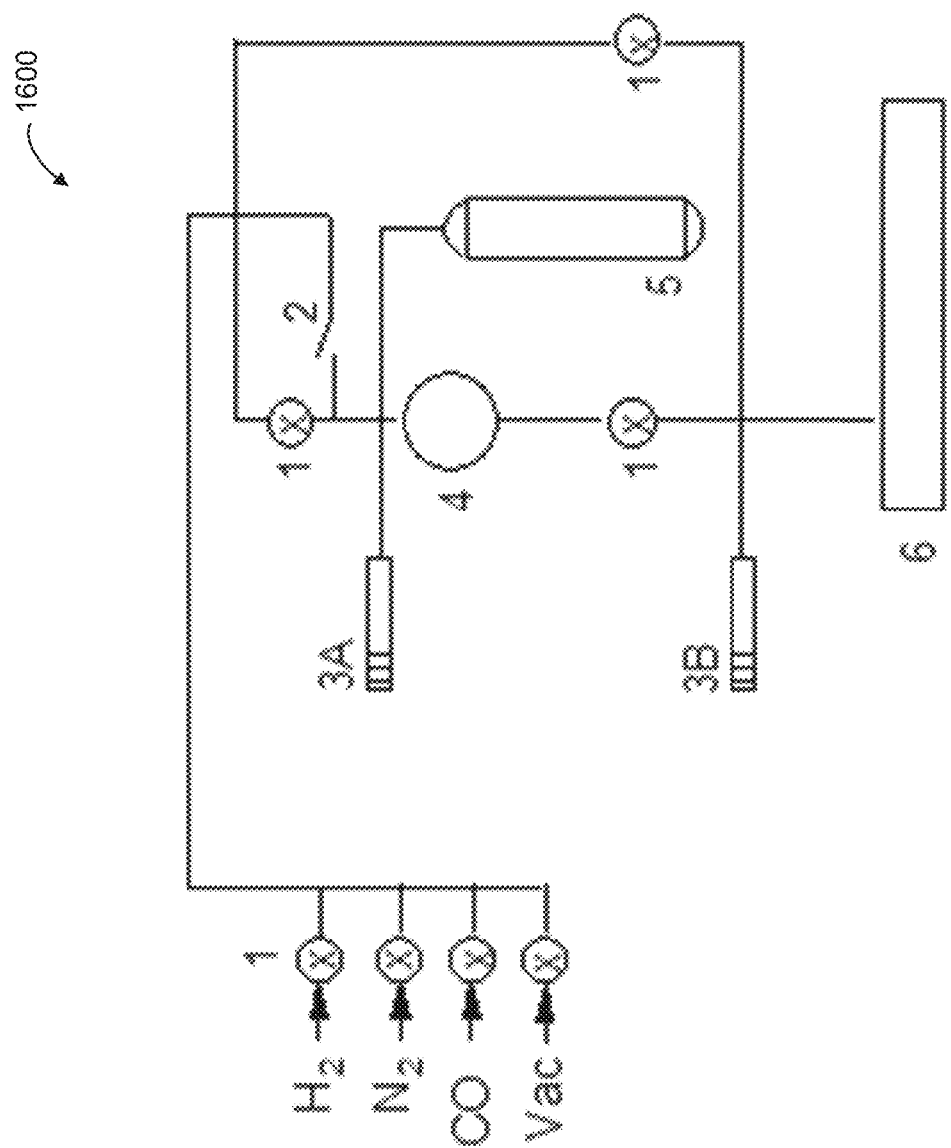
FIG. 16 is a schematic illustrating the components of a thermal catalytic hydrogenation system.

Referring to FIG. 16, a schematic illustrating the components of a thermal catalytic hydrogenation system is shown.

Thermal catalytic hydrogenation system 1600 may be one implementation of hydrogenation device 150 of FIGS. 1-3 and FIGS. 10-14. Thermal catalytic hydrogenation system 1600 may include a reactor configured for continuous monitoring of a hydrogen uptake rate. Reactor may include a standard 100 mL stainless steel PARR Autoclave 5. The entire vessel of the reactor may be removed from a stand as a complete assembly for either charging or product recovery. The reactor is equipped with a magnetically coupled drive with a permanent magnet for the inner rotor, to which the stirring shaft is attached. Additionally, a water cooling sleeve attached to the drive protects the components from excessive heat arising from a head of the reactor. The first port, 1 accommodates a safety rupture disc intended to release pressure if a critical level is exceeded. Port 2 is a combination port which holds liquid sampling and gas inlet valves. The sampling valve allows removal of liquid product samples without the need to open the reactor. A dip tube fitted with stainless steel frit at the tip allows extraction of liquid samples while allowing the catalyst to remain in the reactor. The catalyst may then be reused in subsequent reactions. Port 3A is a combination port configured to accommodate a pressure gauge and a ⅛" stainless steel needle valve. Port 3B is a second combination port accommodating a pressure gage and a ⅛" stainless steel needle valve. The latter is used as a primary gas inlet port for initially purging and pressurizing the reactor and the port itself is connected to the volumetric section of the reactor system through a ⅛" stainless steel tube. Port 4 comprises a J-type thermocouple while the remaining two ports can be fitted with a cooling coil for accurate control of the reactor temperature. The cooling coil may also be removed to produce two additional ports. A first additional port may be left blank while a second additional port, 6 may be fitted with ¼" on/off valve used for loading reaction solutions using gas-tight syringes.

For catalyst activation (pre-reduction), the reactor may be charged with 5 wt % Ru/C catalyst and 40 mL deionized water. The reactor may be alternately purged with argon 5 times and hydrogen also 5 times. The system 1600 may be pressurized to 800 psi, the reactor heated to the desired temperature and stirred for 3 hours at stirring rate of 200-300 RPM. The reactor may then be cooled to ambient temperature, and without opening the reactor, the water may be siphoned out through a dip tube, fitted with 2 mkm stainless still fritted filter.

After catalyst activation (pre-reduction), the reactor may be charged with 41.5 gm of 5% aqueous oxalic acid solution using a gas-tight syringe. To remove dissolved oxygen, the feed solution may be kept in a septa-sealed glass bottle and may be carefully purged with inert gas for at least 30 min before injection into the reactor. The reactor may be flushed 5 times and pressurized with hydrogen to 800 psi, the stirring rate may be set initially to 200 RPM and the reactor heated to desired temperature (between 50° C. and 170° C.) over a period of 60 minutes. The pressure may be adjusted to the desired setting, the stirring rate increased to 800-900 RPM and monitoring of the hydrogen uptake was initiated. During the first 6 hours, samples may be taken at 2 hour intervals and hydrogenations were typically continued for 21 hours.

Catalysts employed in the hydrogenation reactions of thermal catalytic hydrogenation system 1600 may include Ru/C, $Ru/SiO_2$, $Ru/Al_2O_3$, Pd/C, and Cu-Chromite. Temperatures may range from approximately 50° C. to approximately 170° C. Hydrogen may be employed at pressures of about 300 psi to about 1500 psi. Stirring rates may range from about 400 RPM to about 800 RPM. The hydrogenation reactor may be stainless steel, unlined or Teflon lined, or glass lined. The reactor may also be made of Hastelloy or Elgiloy or other corrosion resistant materials. Starting material concentrations of oxalic acid may range from about 5% by weight to about 50% by weight. Products from the thermal catalytic hydrogenation reaction may include mono ethylene glycol, glycolic acid, and acetic acid.

In one exemplary operation, to a container charged with 7.5% by weight of activated (pre-reduced) Ru/C catalyst was added 100 gm of a 25% by weight oxalic acid solution in water. The mixture was subjected to thermal catalytic hydrogenation conditions as described above at a temperature of 75° C., with a stirring rate of 400 RPM and a pressure of 1500 psi of hydrogen. After six hours, the reaction was worked up to provide by weight 76.4% glycolic acid, 6.6% mono-ethylene glycol, and 10.5% acetic acid with a total recovered carbon balance of 93.5%.

In another embodiment, the temperature of the hydrogenation may be initially held at a temperature between 50° C. to 85° C. for a period of 5 to 8 hours followed by an increase in temperature to between 110° C. and 150° C. for a period of 2 to 5 hours. At the end of the reaction monoethylene glycol may be isolated. Initial hydrogenation at a lower temperature may minimize thermal decomposition of oxalic acid.

In another embodiment, after the reaction mixture has reached a reaction temperature between 50° C. and 170° C., the oxalic acid may be slowly added to the reaction mixture in order to minimize the concentration of oxalic acid in the reaction mixture.

Figure 17:
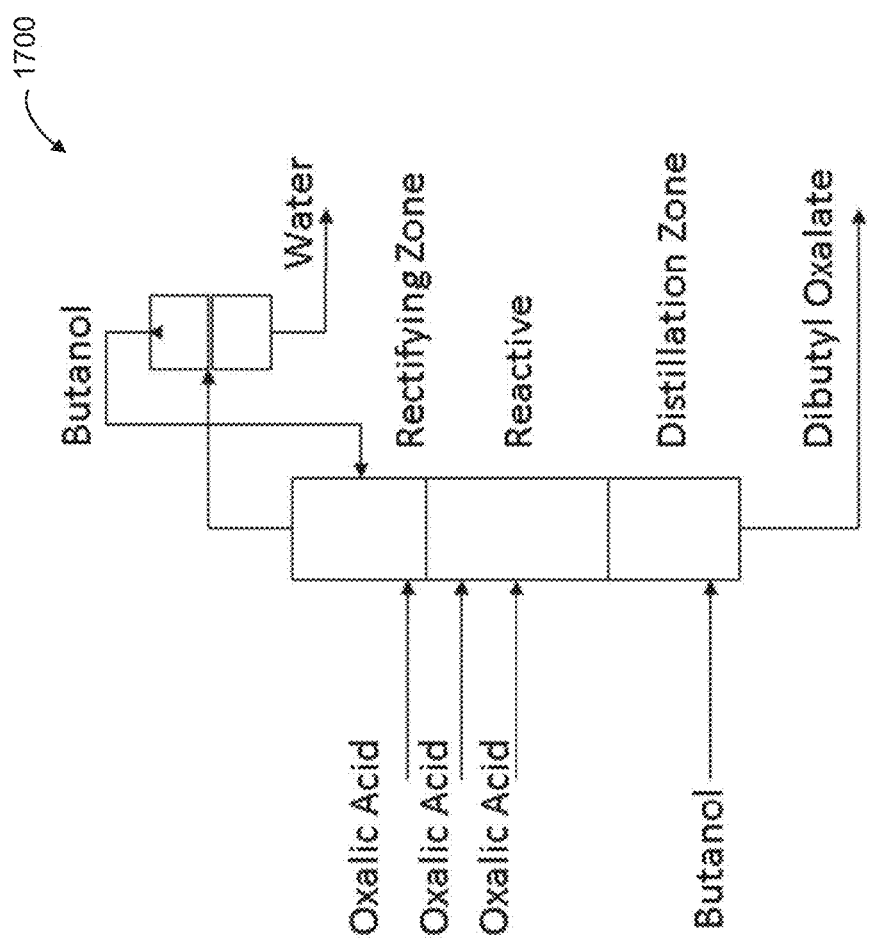
FIG. 17 is a schematic illustrating a reactive distillation column.

Referring to FIG. 17, a schematic illustrating a reactive distillation column is shown. Reactive distillation is a process technology with the potential to simultaneously perform chemical reactions and separations of product and reactants. The reactive distillation process performed by the reactive distillation column 1700 may be configured for esterification of oxalic acid with alcohol (1-butanol, ethanol and methanol) to produce dialkyl oxalate (dibutyl oxalate (DBO), diethyl oxalate (DEO), dimethyl oxalate (DMO), and the like.

Reactive distillation column 1700 may include a rectifying zone, a reactive zone and a distillation zone. Reactive distillation column 1700 may receive oxalic acid and an alcohol, such as butanol. Reactive distillation column may simultaneously reactive and separate the dibutyl oxalate which may then be hydrogenated to mono-ethylene glycol.

Oxalic acid has unique properties. It is highly acidic compared to other dicarboxylic acids and it is thermally unstable due to the presence of the adjacent carboxylic acid groups. Acidity and thermal stability must be carefully considered when designing a process to selectively synthesize a dialkyl ester and separate it from other chemical species.

Once formed, an oxalic acid diester may then be hydrogenated to mono-ethylene glycol (MEG) with great selectivity and efficiency. Oxalic acid diester may be obtained by condensing oxalic acid with low molecular weight alcohols such as methanol, ethanol, propanol, isopropanol, butanol or isobutanol using an acid. Protic Bronsted acids such as $H_2SO_4$, HCl, $H_3PO_4$, p-TsOH, and MsOH have been used as the acid catalysts in conventional esterification chemistry. Esterifications may also be catalyzed with solid acids such as Amberlyt-15, Amberlyst-35, Smopex 101, Zeolite-Y, H-USY, Zeolite-X, Zeolite-β, Zeolite Mordenite, Silica-Alumina, Molybdatophosphoric acid hydrate, sulfated zirconia, sulfated $SnO_2$, sulfated $TiO_2$, sulfated $Nb_2O_5$, Tungstated $ZrO_2$, Nafion $SiO_2$ composite (SAC-13), $Mo/ZrO_2$, $Nb/ZrO_2$ etc.

The use of solid acids for esterifications may be advantageous due to its simplicity at a process level. Solid acids may be placed in a fixed-bed type system thereby reducing the overall capital cost of the process by eliminating a need for a separation of the acid from the reaction mixture. In most of the cases, mineral acids that are used for esterification are lost without recovery due to low concentration, which in turn increases downstream purification and waste treatment costs.

Both conventional esterification methods (such as: Soxhlet extraction, liquid-liquid extraction, Dean-Stark, in situ drying methods, etc.) as well as advanced reactive distillation column (RDC) methods may be used to form oxalate esters. Various alcohols, catalysts, oxalic/alcohol ratio, catalyst loading, temperature and other reaction conditions have been considered in order to enhance the kinetics, product concentration, and yield.

Bench scale batch reactions of the esterification of oxalic acid with methanol, ethanol, and butanol using solid acids such as Amberlyst-15 and Silica-Alumina may be conducted to determine rate and conditions for the optimal yield of the esterification. Removal of water may generate optimal yields and rates. These parameters may be utilized to design the reactive distillation column 1700 for the esterification of oxalic acid with a solid acid catalyst, which shifts the esterification of dialkyl oxalate reactions both chemically and thermodynamically to overcome the theoretical limits imposed by both chemical and phase equilibria of the highly non-ideal systems.

Esterification Experiments
Diethyl Oxalate (In Situ Drying Agent):

An anhydrous oxalic acid (1 g, 11.1 mmol) was placed in a round bottom flask and was dissolved in anhydrous ethanol (50 mL, 39.45 gm, 85.6 mmol). The mixture was stirred at room temperature until the oxalic acid dissolved. Amberlyst 15 hydrogen form (2.00 gm) was added along with magnesium sulfate (2.5 gm, 20.77 mmol) and a rubber septum used to seal the flask. The mixture was allowed to stir at 60° C. under a nitrogen filled balloon. After 2.5 hours, additional magnesium sulfate (2.5 gm, 20.77 mmol) was added to the reaction mixture and then stirred for a total of 4.5 hours. The reaction was cooled and filtered. The crude liquid reaction mixture was concentrated via rotary evaporation affording a light brown oil containing a small amount of residual magnesium sulfate.

Dimethyl Oxalate (Soxhlet):

An anhydrous oxalic acid (12.22 gm, 0.135 mol) was dissolved in anhydrous methanol (110 mL, 86.5 gm, 2.7 mol) in a round bottom flask and stirred until the oxalic acid was dissolved. Toluene (110 mL) was added to the mixture along with p-toluene sulfonic acid (1.28 gm, 6.75 mmol). A Soxhlet extractor containing a glass thimble packed with magnesium sulfate was placed over the round bottom flask. The mixture was refluxed for 18 hours. At the end of this time, the reaction mixture was cooled to room temperature and solvent was concentrated via a rotary evaporation yielding a white solid (13.8 gm, 87% crude yield).

Dimethyl Oxalate (Dean-Stark)

An anhydrous oxalic acid (22.22 gm, 0.25 moles), p-toluene sulfonic acid monohydrate (2.34 gm, 0.123 moles) and methanol (100 mL, 79.1 gm, 2.47 moles) were added to a round bottom flask. The round bottom flask was attached to a dean-stark apparatus filled with toluene. The reaction was refluxed for 18 hours. At the end of this time, the reaction mixture was concentrated via a rotary evaporation affording white solid (30.17, 95.5% crude yield).

Dimethyl Oxalate (Liquid-Liquid Extractor):

An anhydrous oxalic acid (66.68 g, 0.74 moles), methanol (600 mL, 474.6 g, 14.81 moles) and deionized $H_2O$ (290 mL) were added to a body of the liquid-liquid extractor. P-toluene sulfonic acid monohydrate (27.06 gm, 0.142 moles) was added to a reactor body along with toluene (100 mL). Toluene (500 mL) may also be placed in the round bottom flask of the liquid-liquid extractor and heated in a 150° C. oil bath. The reaction was left to stir for several hours. The organic solution was concentrated via a rotary evaporation affording a white solid (44.3 gm, 51% crude yield).

Note on Catalyst Activation (Silica-Alumina):

Silica alumina (50 gm) was placed in 1M ammonium chloride (250 mL) and may be stirred for six hours at room temperature. The silica-alumina was filtered off with a fritted Buchner funnel, washed with deionized $H_2O$, and dried for several hours. Around 8.65 gm was left to calcine for 5.5 hours under argon gas at 450° C. in a tube oven. After cooling to room temperature, the silica-alumina may be placed in a vacuum oven at 60° C. for 45 minutes prior to use.

Reactive Distillation

Reactive distillation involves the simultaneous reaction as well as separation of the reaction components using a catalyst at proper system temperature. Esterification is an exothermic process and hence lot of heat is generated during the reaction. In conventional process, this majority of the heat is extracted using heat transfer methods and not utilized comprehensively. In RDC, the heat is utilized internally to heat the reaction components in order to carry out separation simultaneously. This advanced simultaneous process reduces thermal energy cost considerably. Based on the physical and chemical properties such as boiling point, stability, miscibility, affinity, reactivity of the reactants and products, RDC methods of producing dibutyl oxalate (DBO) and diethyl oxalate (DEO) have been designed and tested.

Reactive Distillation of Dibutyl Oxalate

As shown in FIG. 17, oxalic acid in 1-butanol solution at 95° C. or higher is fed into a location at the upper portion of the column, and the rest of 1-butanol (total of 1:5 molar ratio of oxalic acid to butanol) is fed at a location of the lower portion of the column close to the column bottom at a temperature of 100° C. to 130° C. The column is packed with solid acid catalyst in the middle section, the lower and upper sections of the column are packed with structural packing without catalytic reactivity for separations purpose only, identified as rectifying and distillation zones.

Esterification happens in the middle of the column. Water and unreacted butanol are recovered at the top of the column in a decanter, the butanol in the top phase is then recycled back for further esterification. The bottom stream has a dibutyl oxalate concentration of 46% wt to 75% wt, the rest of the mixture is butanol along with a minor amount of water, the product stream may be further separated to yield higher purity dibutyl oxalate for subsequent use.

Reactive Distillation of Diethyl Oxalate

Oxalic acid in ethanol (EtOH) solution at 79.4° C. may be fed into proper location at the upper portion 1710 of the column and the rest of ethanol (total of 1:5 molar ratio of OA to EtOH) may be fed at a proper location of the lower portion of the column 1720 at a temperature of 80.5° C. The column may be packed with acid catalyst in the middle section 1730, the lower and upper sections 1710, 1720 of the column are packed with structural packing without catalytic reactivity for separations purpose only.

Esterification happens in the middle of the column, 1730, the reactive zone. Unreacted ethanol is recovered at less than 93% weight at the top of the column 1710 (lower than the azeotrope composition with water), it is then dried and recycled back for further reaction. The bottom stream (product stream) has a diethyl oxalate concentration of 87% weight, the rest is water and a minor amount of ethanol, the stream may be further separated to yield higher purity diethyl oxalate for subsequent use.

TABLE

Comparison of the esterification rate of batch and RDC method:

| | Conventional batch method | RDC method |
|---|---|---|
| Rate of dialkyl ester formation | 30-150 gram/hour-liter | 150-400 gram/hour-liter |

Due to the efficient removal of water in RDC method, the rate may be much higher than that of conventional batch method.

The reactive distillation column 1700 may be designed in a way that it can separate reactive mixtures involving azeotropes to a large extent. Such separations may be difficult to achieve by conventional "distillation after reaction" mechanism where reactions are fully controlled by the equilibrium limit and phase behavior is controlled by azeotrope properties.

The heat released by esterification of oxalic acid may be used for vaporizing water without the need for heat exchange equipment and heating and cooling resources, and without thermal resistance.

Solid acid Amberlyst and Zeolites catalysts may be used, instead of $H_2SO_4$ or other liquid acids which may be lost in the process resulting in additional waste treatment costs. Solid acid catalysts may be packed in a bed and have a lifetime of several years.

The esterification reactions may occur at atmospheric pressure and temperature ranges from 100° C. to 160° C., depending on the catalyst used.

The oxalate esters obtained from reactive distillation may be used in subsequent processes. For example, the esters may be reduced to ethylene glycol via thermal catalytic hydrogenation.

Referring once again to FIGS. 6B and 6C, oxalic acid may be electrochemically reduced to $C_2$ and $C_4$ products at the cathode 122 of the electrochemical cell 620, 630. Various anodic reactions that liberate available H+ may be employed. As shown in FIG. 6B, electrochemical cell 620 may be configured for water oxidation to $H^+$ and $O_2$ if a benign side product is desired. This is given by the equation for $C_2$ products:

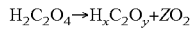
$$H_2C_2O_4 \rightarrow H_xC_2O_y + ZO_2$$

As shown in FIG. 6C, electrochemical cell 630 may be configured for HX oxidation to a halogen and $H^+$ if a halogen is desired as the product. This is given by the equation for $C_2$ products:

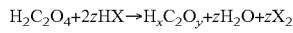
$$H_2C_2O_4 + 2zHX \rightarrow H_xC_2O_y + zH_2O + zX_2$$

Similarly, the oxidation of other organic and inorganic species may be employed as the anolyte reaction and are not limited to these variations.

As shown in FIGS. 6B and 6C, electrochemical cells 620, 630 may have cathodes that may include and are not limited to Pb, C, graphite, semiconductors, In, Sn, Zn, Cd, Hg, amalgams, Bi, Ga, alloys containing Pb, In, Sn, Zn, Cd, Hg, Bi, Ga, bimetallics containing Hg with another conductor, or other combinations of bimetallics, and metal carbides. The catholyte may include homogeneous catalysts. Homogeneous catalysts may include aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., Cl—C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxypyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

For bromine and iodine anode chemistry, carbon and graphite may be particularly suitable for use as anodes in electrochemical cells 620, 630. Polymeric bonded carbon sheets may also be used. For other chemistries, carbon, cobalt oxides, stainless steels, their alloys and combinations may be employed as well as coatings of precious metal oxides such as ruthenium and iridium oxides, as well as platinum and gold and their combinations as metals and oxides on valve metal substrates such as titanium, tantalum, or niobium.

A desired salt in the catholyte region 116 of electrochemical cells 620, 630 may include either HBr, HCl, HI, $H_2SO_4$, bromide, chloride, or sulfate salts where the cation is sodium, potassium, ammonium, tetraalkylammonium, or another single or divalent cation. Concentrations of salts may range from mM to M. A desired salt in the anolyte region may include either HBr, HCl, HI, $H_2SO_4$, bromide, chloride, or sulfate salts where the cation is sodium, potassium, ammonium, tetraalkylammonium or another single or divalent cation. The concentration may range from mM to M. The anodic chemistry may also be operated in the gas phase. In this embodiment, anhydrous HBr or HCl gas anolyte may be used as well as water vapor.

In a preferred embodiment, the solvent may be water with concentrations of oxalic acid near saturation levels of about 12% by weight. The solvent may also be a variety of non-aqueous solvents with specifically added quantities of water. These non-aqueous solvents could include but are not limited to propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, and ionic liquids. Oxalic acid may be soluble in the solvent chosen. In one embodiment, oxalic acid in propylene carbonate with the appropriate salt may be used as the catholyte.

A preferred oxalic acid concentration may range from 1 mM to about 12% by weight in aqueous solution. The solubility limit of oxalic acid may be increased by using solvents other than water. The solubility limit may also be increased by increasing the temperature of the reaction and/or through the use of electrolytes that have a salting effect on oxalic acid. These include thiocyanates, perchlorates, tetrafluoroborates, and hexafluorophosphates.

Generally, the solvent may be the same in both the catholyte region 116 and anolyte region 118 of electrochemical cells 620, 630. However, in certain embodiments, the solvent used in the catholyte region 116 and anolyte region 118 may differ. If a halogen is produced in the anolyte region 118 of electrochemical cell 630, the solvent of choice may be stable in the presence of $Br_2$, $Cl_2$, or $I_2$.

In the catholyte region 116, the pH may depend on the concentration of oxalic acid and the electrolyte salt or acid employed. In general, the pH may range from 0 to 5. In the anolyte region 118, the pH may depend on the concentration of the electrolyte acid employed. In general, the pH may range from 0 to 5.

The temperature used may depend on the solvent chosen. For aqueous solution, the preferred temperature range may be 5° C. to 80° C. Lower and higher temperature ranges may be employed by using various solvents. A catholyte cross sectional area flow rate range may be 2-3,000 gpm/ft$^2$ or more (0.0076-11.36 m$^3$/m$^2$). A flow velocity range may be 0.002 to 20 ft/sec (0.0006 to 6.1 m/sec).

Electrochemical cells 620, 630 may include zero-gap, flow-by, and flow-through designs with a recirculating catholyte electrolyte with various high surface area cathode materials. Also flooded co-current packed and trickle bed designs with the various high surface area cathode materials may be employed for the electrochemical cells 620, 630. Bipolar stack cell designs, high pressure cell designs and filter press, zero gap designs with gas phase anodic chemistries and either aqueous or non-aqueous cathodic chemistry may be employed for the electrochemical cell 620, 630.

In one embodiment, the catholyte may include oxalic acid, a solvent, and a salt, with a gas phase HBr anolyte. The cathode and anode materials may be in direct contact with the membrane and there may be less than a few millimeters of depth to the anode or cathode region. High surface area of the anode and cathode may be achieved through micro and nano-structuring of the electrode materials. Mixed Phase-Gas phase anodic chemistry with aqueous phase or non-aqueous phase cathodic chemistry may also be implemented.

The cathode/anode electrodes may include a preferred void volume, ranging from 30% to 98% and a specific surface areas from 2 cm$^2$/cm$^3$ to 500 cm$^2$/cm$^3$ or higher. Surface areas also may be defined as total area in comparison to the current distributor/conductor back plate, with a preferred range of 2× to 1000× or more.

Cation ion exchange type membranes may be preferred, especially those that have a high rejection efficiency to anions, for example perfluorinated sulfonic acid based ion exchange membranes such as DuPont Nafion brand unreinforced types N117 and N120 series, more preferred PTFE fiber reinforced N324 and N424 types, and similar related membranes manufactured by Japanese companies under the supplier trade names such as Flemion.

Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have much higher anion rejection efficiency. These are sold by DuPont under their Nafion trademark as the N900 series, such as the N90209, N966, N982, and the 2000 series, such as the N2010, N2020, and N2030 and all of their types and subtypes.

Hydrocarbon based membranes, which are made from of various cation ion exchange materials may also be used if the anion rejection is not as critical, such as those sold by Sybron under their trade name Ionac, ACG Engineering (Asahi Glass) under their Selemion trade name, and Tokuyama Soda among others on the market.

Microporous separators may also be employed in some system options such as microporous PVDF (polyvinylidiene difluoride), PTFE (polytetrafluoroethylene), or glass fiber based materials as well as commercial diaphragms. Other separators as describe elsewhere herein may also be used.

Figure 18:
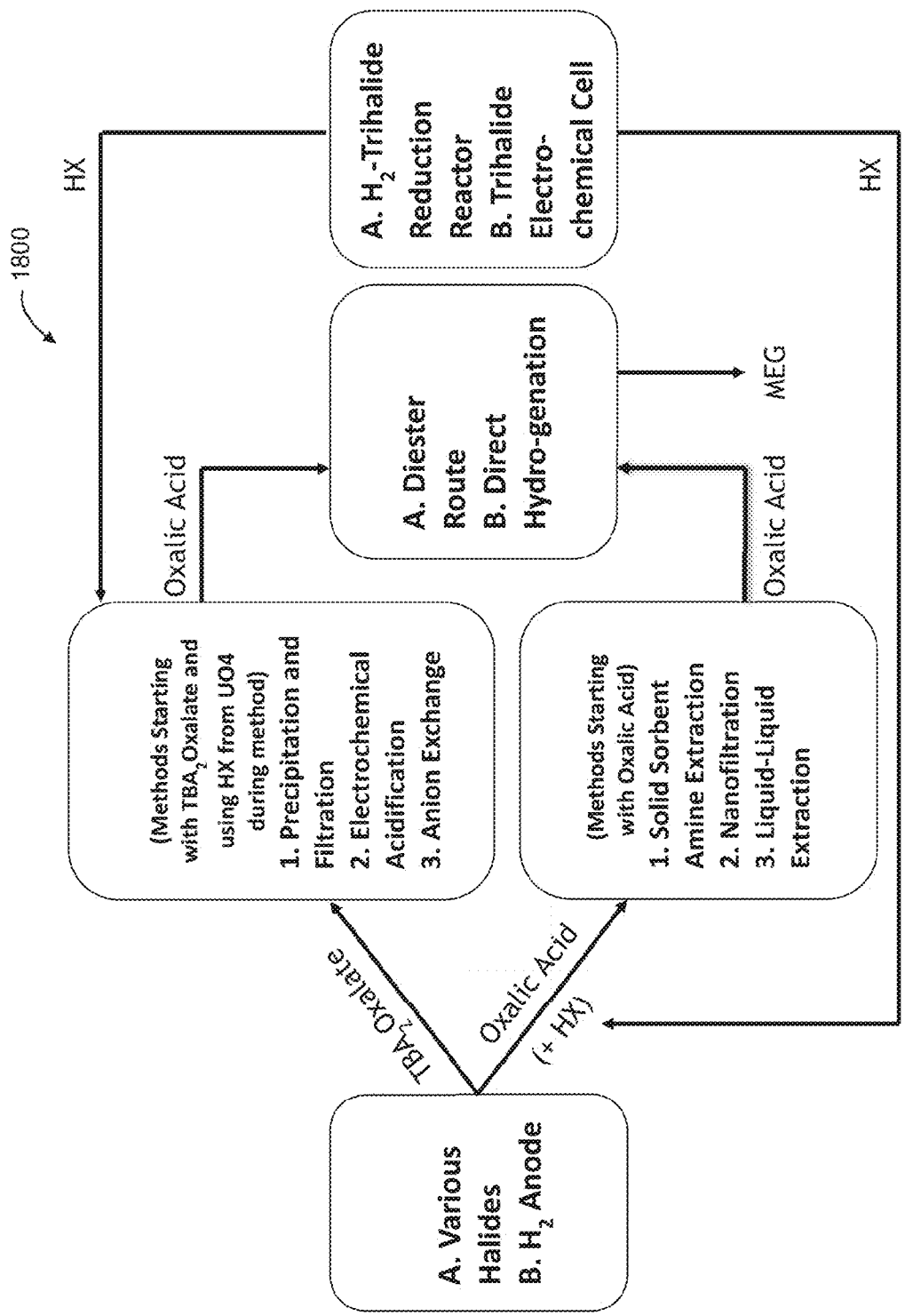
FIG. 18 is a schematic illustrating a process for the conversion of carbon dioxide to two-carbon products such as mono-ethylene glycol.

Referring to FIG. 18, a method 1800 for conversion of carbon dioxide to oxalate, oxalic acid and oxalic acid reduction products is shown.

Figure 22:
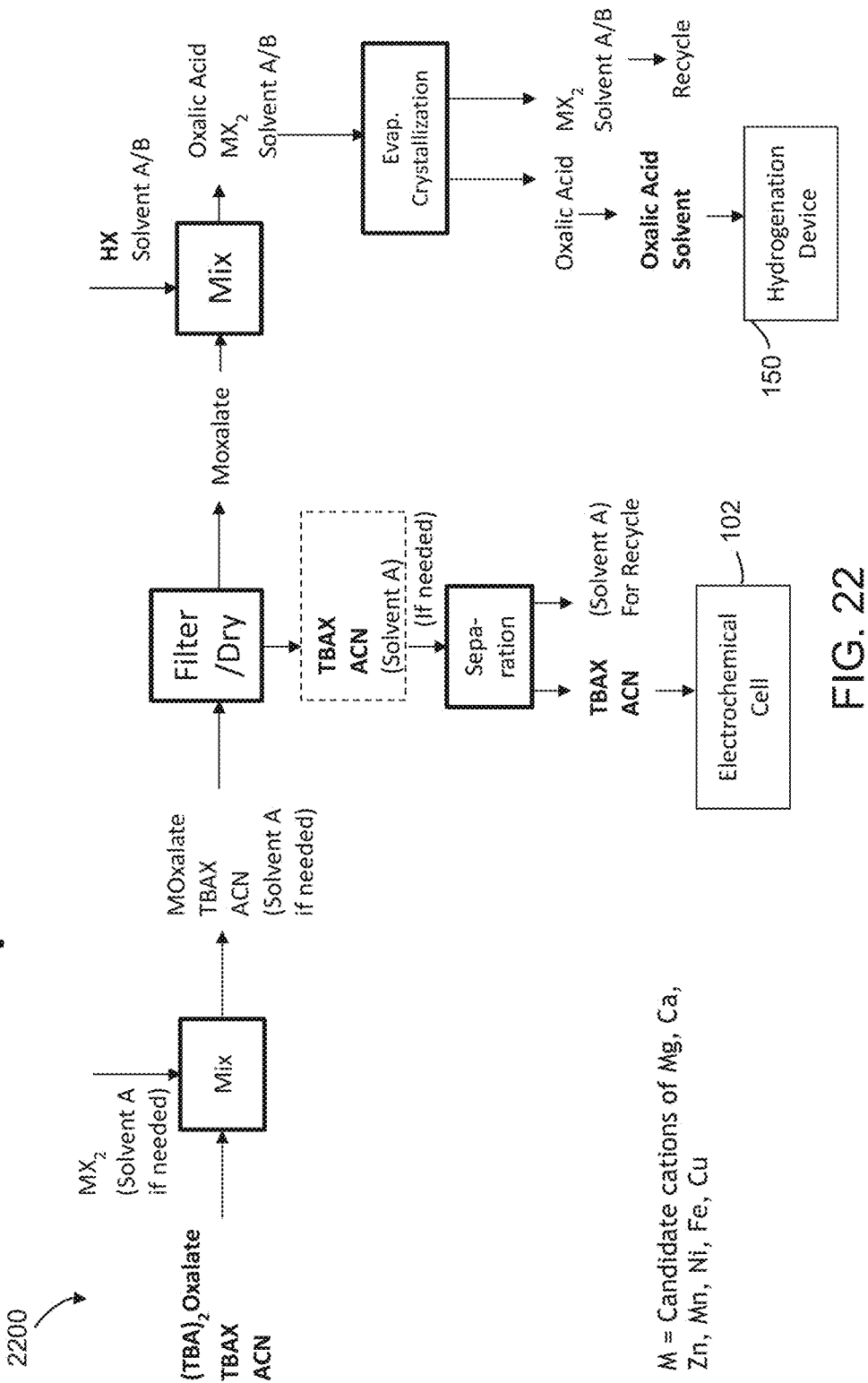
FIG. 22 is a schematic illustrating a process for purifying oxalic acid.

Referring to FIG. 22, a method 2200 for purifying an oxalate salt is shown. Method 2200 may begin with an oxalate salt, such as tetrabutylammonium oxalate or other oxalate salt in a non-aqueous aprotic solvent, such as acetonitrile, is received as a starting material. The oxalate salt may be purified by reacting the oxalate salt with a metal ion (MX$_2$), optionally dissolved in a second solvent (solvent A), to form a weakly soluble, or insoluble complex (M-Oxalate). For example, metal ions such as Mg, Ca, Zn, Mn, Ni, Fe, and Cu may be employed. The mixture may be filtered to yield the solid M-Oxalate and a solution of salt, such as tetraalkylammonium halide, in solvent or a mixture of solvents. The salt solution and solvent(s) may be recycled. The solid M-Oxalate may be treated with acid HX and solvent or a solvent mixture (solvent NB) to yield oxalic acid and salt MX. Oxalic acid may then be purified from the solution. Salt MX and solvent or solvent mixture (solvent A/B) may be recycled.

In another embodiment, an oxalate salt solution may be electrochemically acidified. Representative electrochemical acidification cells have been discussed previously and are illustrated in FIGS. 7, 8, 9A-C, and 23.

Figure 26:
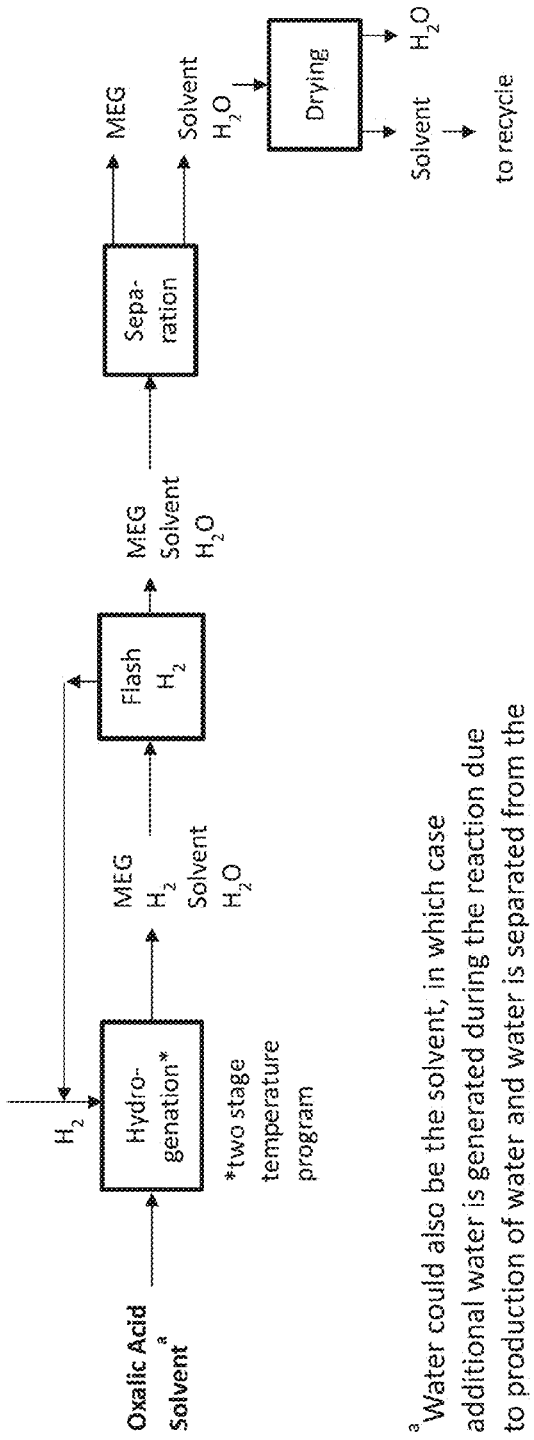
FIG. 26 is a schematic illustrating a process for the conversion of oxalic acid to mono-ethylene glycol.
Figure 27:
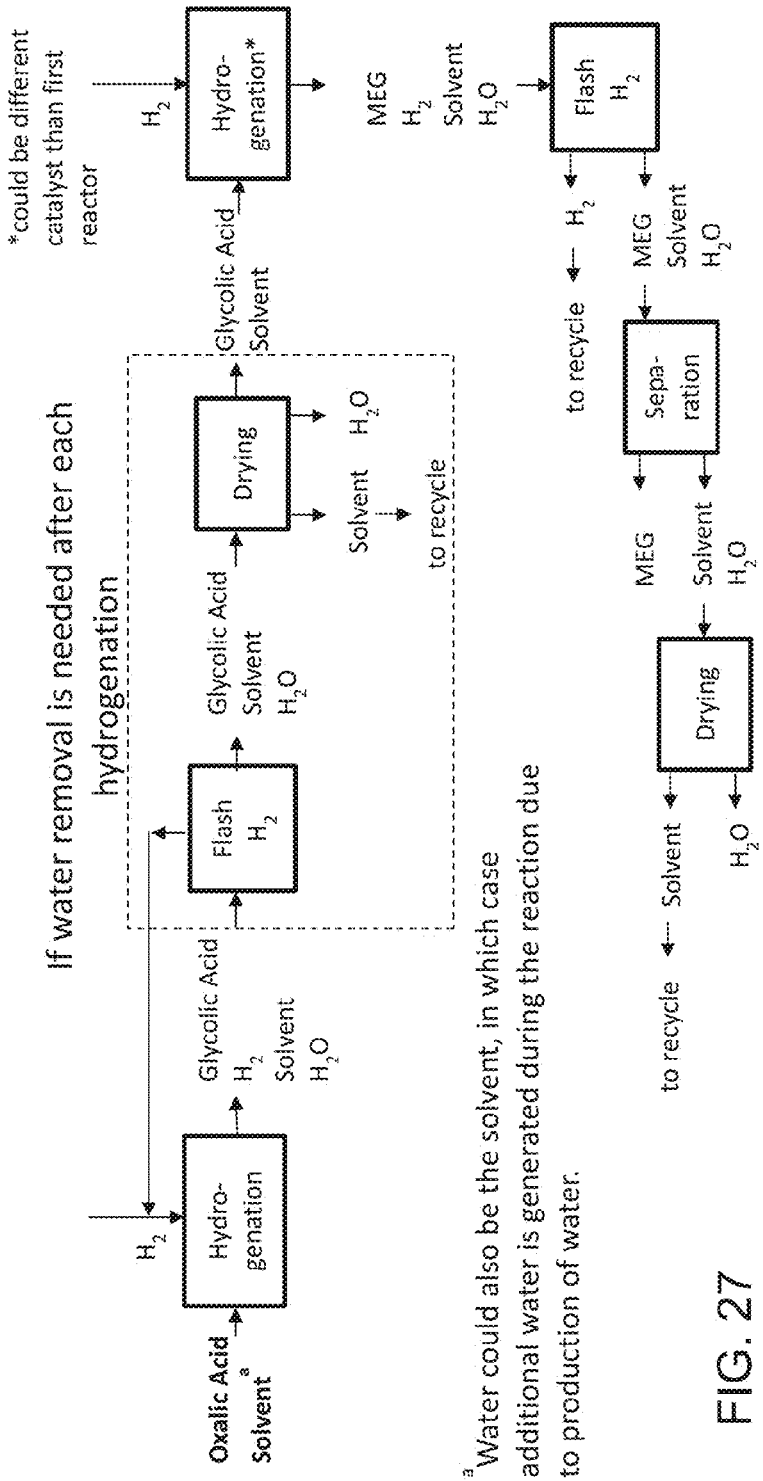
FIG. 27 is a schematic illustrating a process for the conversion of oxalic acid to mono-ethylene glycol.

In another embodiment, an oxalate salt may be purified through the use of an ion exchange column, such as an anion exchange column, as shown in FIG. 26. An oxalate salt, such as a tetraalkylammonium oxalate, in a non-aqueous aprotic solvent, such as acetonitrile, and optionally tetraalkylammonium halide may be flowed onto an ion exchange column to which the oxalate dianion adheres. Oxalate salt solution may be flowed onto the column until oxalate is detected flowing off the column, indicating column saturation. Tetraalkylammonium halide and solvent flowing off the column may be recovered and recycled, for example for use in an electrochemical carbon dioxide reduction cell 102 in FIG. 1. After oxalate salt has been adsorbed onto an ion exchange column, a solution of acid, such a HX, may be flowed onto the column. The acid may convert the oxalate salt to oxalic acid and oxalic acid may flow out of the column with the solvent and unreacted acid. The oxalic acid and acid HX may then be separated, with the HX being recycled, and oxalic acid being isolated or being reacted to form other products, such as further reduced two-carbon products.

In another embodiment, an oxalic acid and tetraallkylammonium halide solution in a non-aqueous aprotic solvent, such as acetonitrile, may be purified through solid sorbent amine extraction. Solid-phase column materials may comprise Dowex MWA-1, Amberlite IRA-910, Amberlite IRA-35, Reillex 425 or similar materials. An oxalic acid solution in a non-aqueous aprotic solvent, such as acetonitrile, and optionally tetraalkylammonium halide may be flowed onto a solid sorbent amine column to which the oxalic acid adheres. Oxalic acid solution may be flowed onto the column until oxalic acid is detected flowing off the column, indicating column saturation. Tetraalkylammonium halide and solvent flowing off the column may be recovered and recycled, for example, for use in an electrochemical carbon dioxide reduction cell 102 of FIG. 1. After oxalic acid has been adsorbed onto a solid sorbent amine column, forming a solid sorbent amine-oxalate salt, a solution of amine base may be flowed onto the column. The base may convert the solid sorbent amine-oxalate salt to soluble amine-oxalate salt and the soluble amine-oxalic acid salt may flow out of the column. The oxalic acid and soluble amine then be separated, for example through heating, with the amine being recycled and oxalic acid being isolated or being reacted to form other products, such as further reduced two-carbon products.

In another embodiment, an oxalic acid and tetraalkylammonium halide mixture may be purified through chromatography. The mixture may be flowed onto a chromatographic medium, such as a hydrophilic medium or a hydrophobic medium. Suitable chromatographic media include silica gel, alumina, polymers, reverse phase silica gel, and related chromatographic media. The oxalic acid and tetraalkylammonium halide mixture may be flowed onto the chromatographic medium in solution, or the mixture may be combined with the chromatographic medium as a solid. After the mixture has been flowed onto the chromatographic medium, or combined with the chromatographic medium, a solvent, or mixture of solvents, may be flowed onto the medium to separate the oxalic acid from the tetraalkylammonium halide. Suitable solvents include water, methanol, ethanol, 1-propanol, isopropanol, acetonitrile, hexane, petroleum ether, diethyl ether, formic acid, acetic acid, ammonia, and triethylamine. The separated oxalic acid may be further reduced to two carbon products, and the tetraalkylammonium halide may be recycled, for example for use in an electrochemical carbon dioxide reduction cell.

Figure 19:
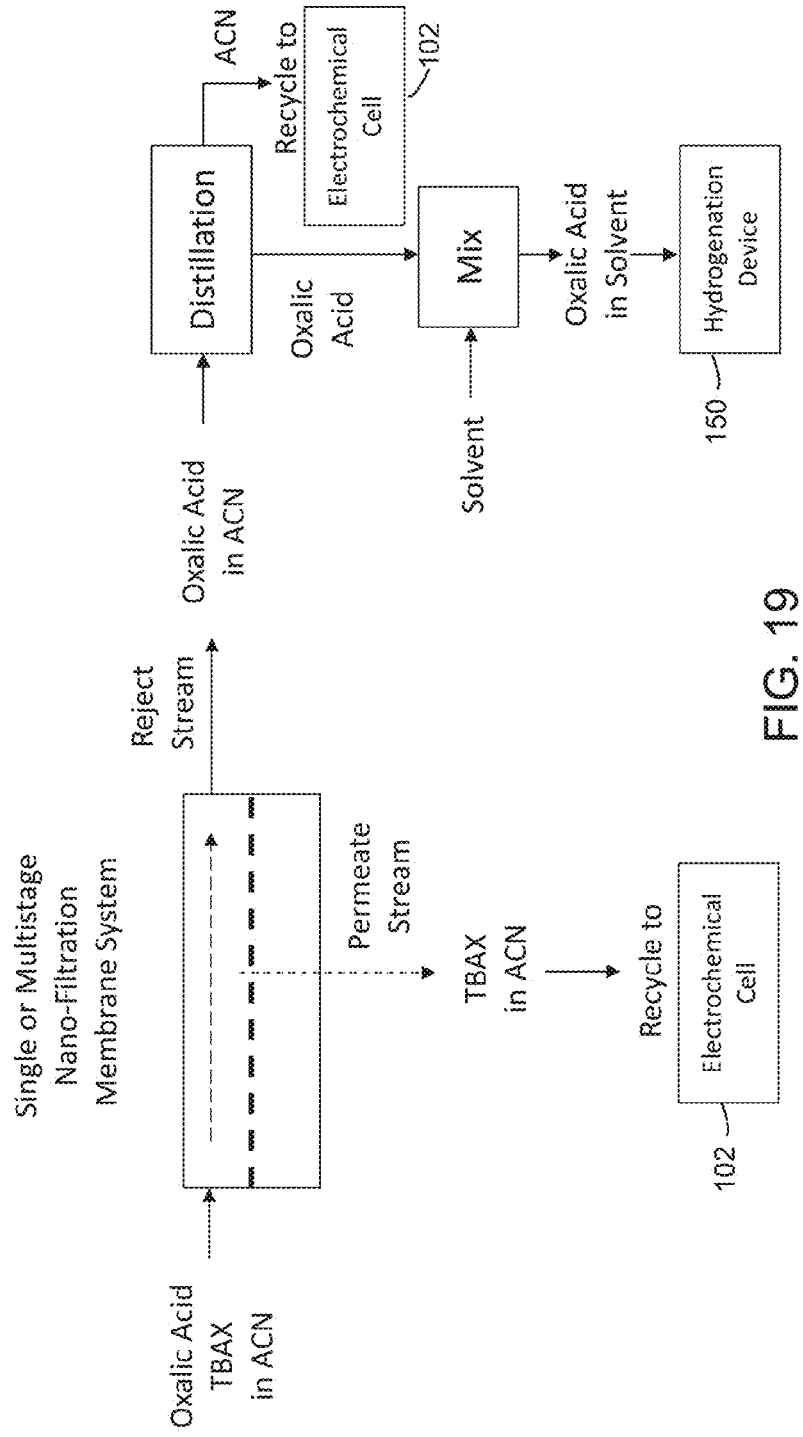
FIG. 19 is a schematic illustrating a process for purifying oxalic acid.

In another embodiment, an oxalic acid and tetraalkylammonium halide solution in a non-aqueous aprotic solvent, such as acetonitrile, may be purified through nano-filtration. Two different nano-filtration methods may be employed. Referring to FIG. 19, a method 1900 may employ nano-filtration that may reject oxalic acid and may allow tetraalkylammonium halide in solvent to pass through the filter. The resulting permeate stream may be recycled. The reject stream of oxalic acid in solvent may be sent to distillation to remove the solvent, which may be recycled, and yield purified oxalic acid. The purified oxalic acid may be further processed to yield other products such as other two-carbon containing compounds. Suitable nano-filtration membranes are solvent stable membranes, such those manufactured by Evonik under the trade name of DuraMem and PuraMem, which also come in different molecular weight cutoffs (i.e., 150, 200, etc. in Daltons) which may also improve the selected separations. The pH adjustment of the solvent solution may also have a pH range where the separation selectivity is also improved, with the addition of excess HX to the solution. In another embodiment, if the ACN is replaced by water, the salts may also be separated using nano-filtration membranes that are suitable for use in aqueous solutions.

Figure 20:
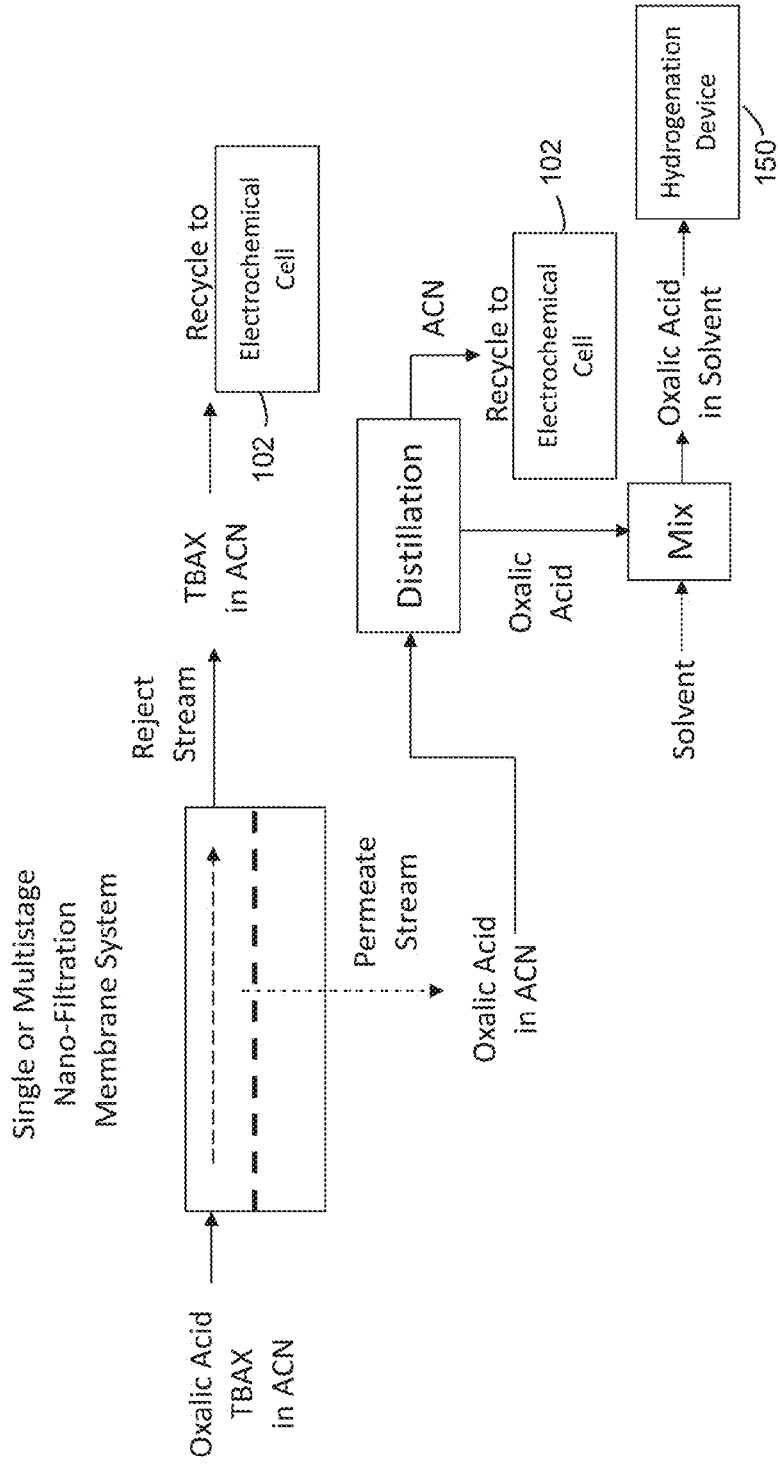
FIG. 20 is a schematic illustrating a process for purifying oxalic acid.

Referring to FIG. 20, a method 2000 may employ nano-filtration that may reject tetraalkylammonium halide and may allow passage of oxalic acid. The reject stream containing tetraalklyammonium halide in solvent may be recycled. The permeate stream containing oxalic acid may be sent to distillation to remove the solvent, which may be recycled, and yield purified oxalic acid. The purified oxalic acid may be further processed to yield other products such as other two-carbon containing compounds.

Figure 21:
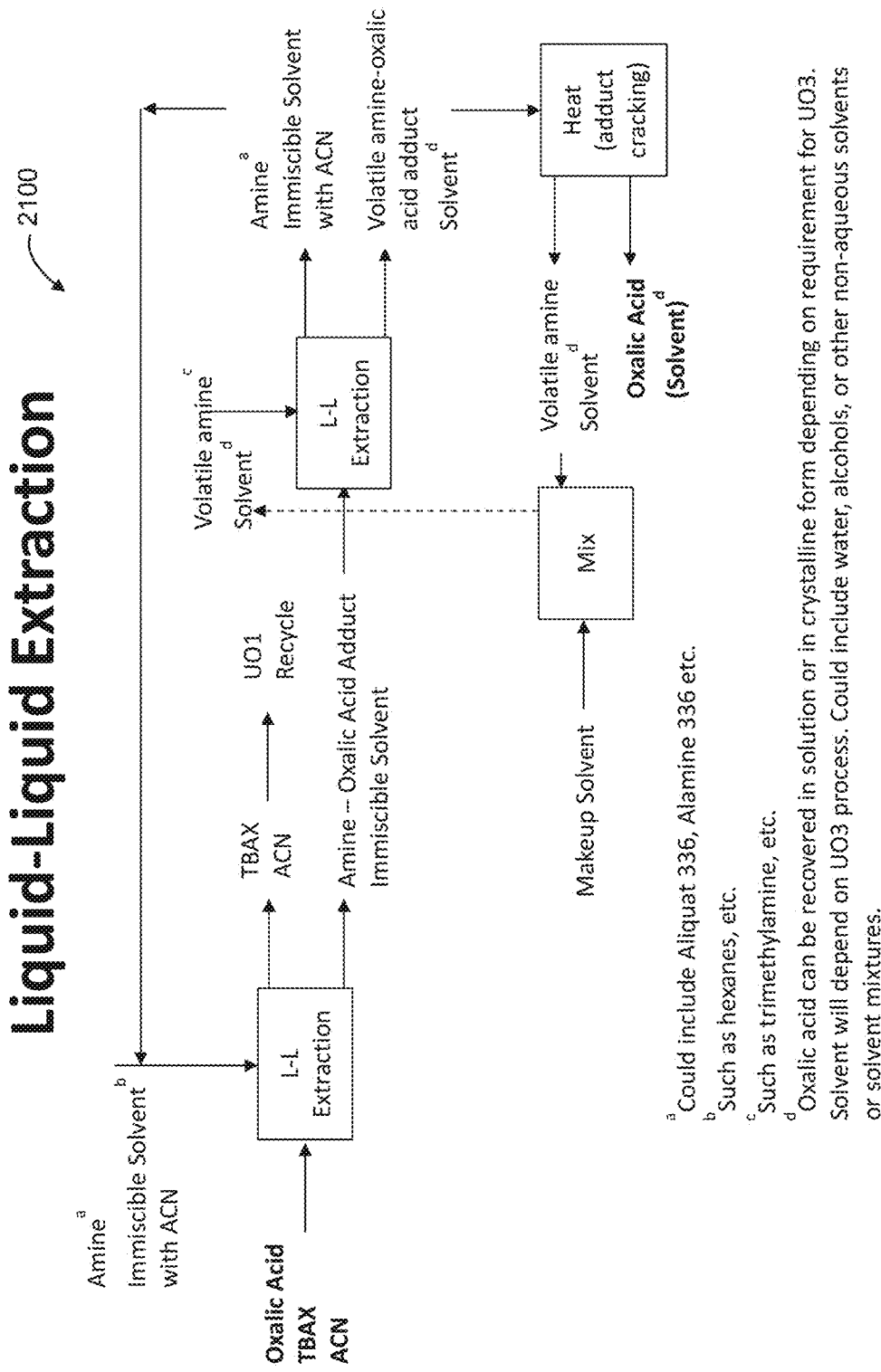
FIG. 21 is a schematic illustrating a process for purifying oxalic acid.

Referring to FIG. 21, a method 2100 for purifying an oxalic acid solution containing tetraalkylammonium halide through amine extraction is shown. A solution of oxalic acid in a non-aqueous aprotic solvent, such as acetonitrile, may be treated with an amine, such as a trialkylamine to form an amine-oxalate salt. An amine-oxalate salt may precipitate from solution or may form a two phase liquid solution. Addition of an amine salt immiscible solvent may optionally be added to achieve precipitation or phase separation. The amine salt may then be filtered or the two liquid phases may be separated to provide a solution of tetraalkylammonium halide for recycling and an oxalic acid-amine salt, which may be a solid or may be in solution. The oxalic acid-amine salt may then be heated to provide purified oxalic acid, which may be used in subsequent reactions, and amine, which may be recycled.

In another embodiment, an oxalic acid solution containing tetraalkylammonium halide may be purified by liquid-liquid extraction in an extractor apparatus. In this embodiment, either the oxalic acid or the tetralalkylammonium halide or other salt may have differing solubility in the different solvents employed. For the case where oxalic acid may have higher solubility in a second solvent, the oxalic acid concentration will increase in the second solvent and decrease in the initial solution. This may leave the tetralkylammonium halide salt in the solvent of the initial solution which may be recycled. A series of extractor apparatuses may be used to achieve the desired purity. For example, counter-current extraction or dropping counter-current extraction may be employed.

Referring again to FIG. 18, once purified oxalic acid has been obtained it may be used in further chemistry. For example, the oxalic acid may be reacted with alcohols to form the diester which can then be reduced to form mono-ethylene glycol. Alternatively, oxalic acid may be directly reduced via thermal catalytic hydrogenation to form glycolic acid, or to form mono-ethylene glycol. In addition, oxalic acid may be electrochemically reduced to form glyoxylic acid.

Figure 25:
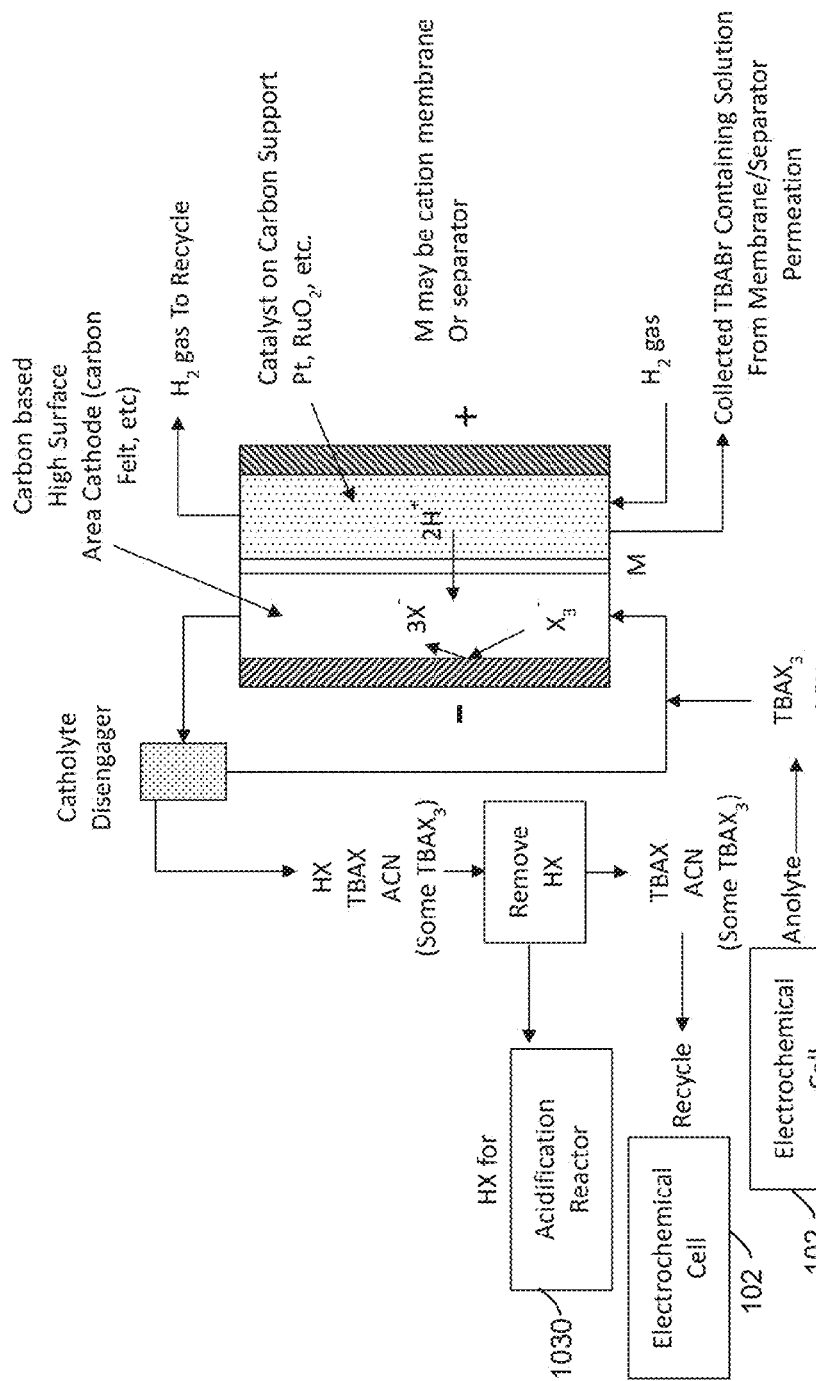
FIG. 25 is a schematic illustrating a process for the electrochemical reduction of halide and trihalide.

As shown in FIG. 18, halide or trihalide anion formed during the electrochemical reduction of carbon dioxide may be recycled through thermal, catalytic, or electrochemical reduction systems. For example, a stream of halogen may be reacted with a stream of hydrogen to form HX and heat. Once the halogen and hydrogen streams are mixed an ignition source would initiate the reaction. Alternatively, halide or trihalide anion may be reacted with hydrogen in the presence of a catalyst to form hydrogen halide and heat. Catalysts such as Pt, Pd, Rh, Ru, Ni, Ir, and other homogeneous or heterogeneous hydrogenation catalysts may be used. Heat from the reaction of hydrogen and halide or trihalide anion may be captured and used for energy production or to provide heat for other processes. As illustrated in FIG. 25, an electrochemical cell may be used to reduce halide or trihalide anion to HX. Finally, halide or trihalide anion may be reacted in a fuel cell to provide HX as well as electrical energy, which may be used in the electrochemical reduction of carbon dioxide.

Figure 28:
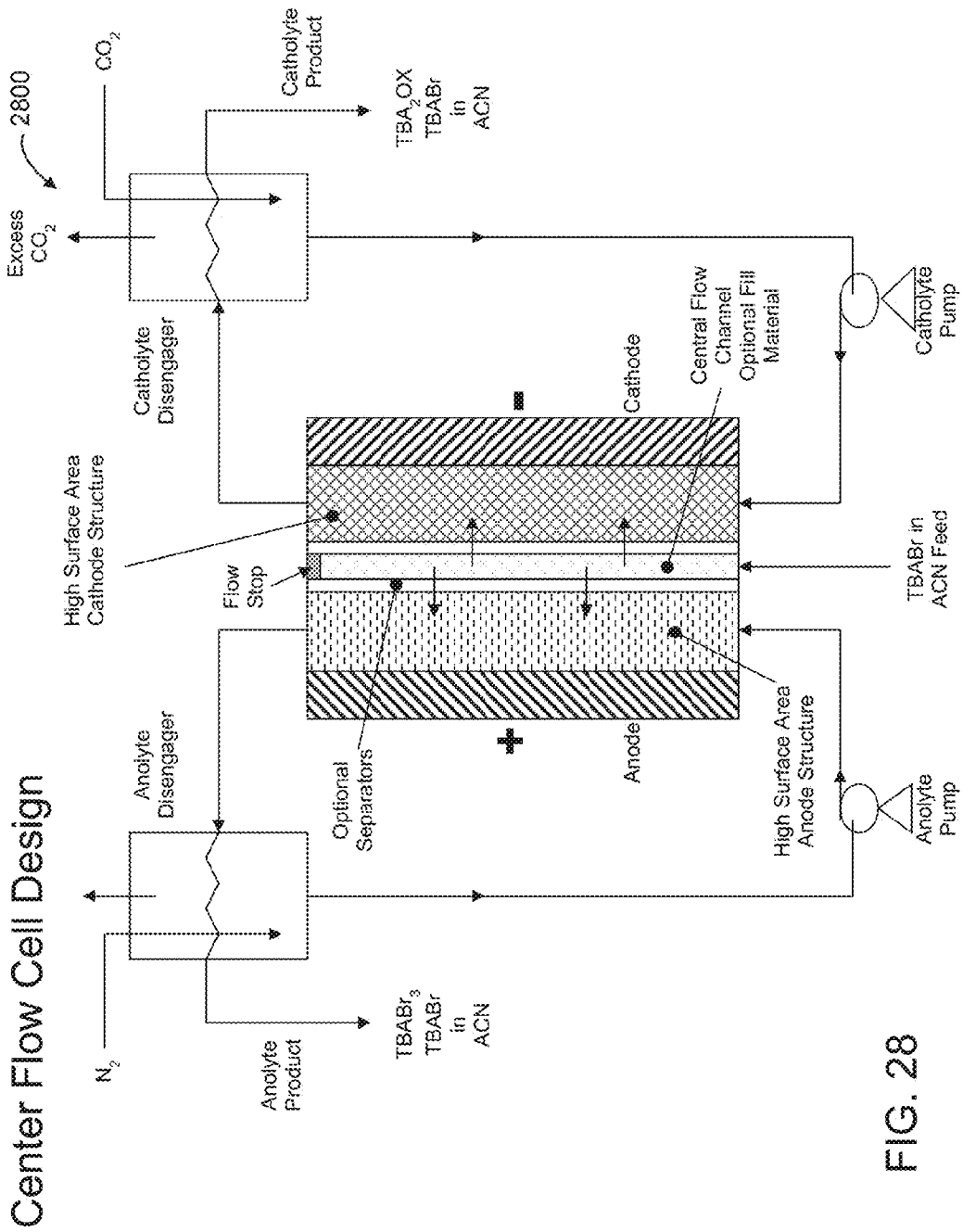
FIG. 28 is a schematic illustrating an electrochemical process for the conversion of carbon dioxide to oxalate.

Referring to FIG. 28, electrochemical cell 2800 for producing oxalate from the reduction of carbon dioxide in a non-aqueous solvent in accordance with an another embodiment is shown. An acetonitrile (ACN) solution with a dissolved conductive salt, for example TBABr, may be introduced into a thin central flow channel or compartment, such that all of the flow may be evenly distributed in width and height from the flow channel into the adjoining anolyte and catholyte regions containing the anode and cathode electrode structures respectively. The central flow channel may comprise a material, such as ionically conductive materials that may include ion exchange beads or inert nonconductive materials with a high open area such as plastic mesh screens, plastic beads, and the like. Advantageously, the flow channel may be kept open and preferably kept dimensionally stable in width or thickness through the height of the flow channel. A separator may be used on either side of the flow channel to help provide the flow resistance required to have an evenly distributed flow into the anolyte and catholyte regions. The separator may be a porous material with a small pore size in the range of 0.01 to 5 microns with an open area in the range of 20 to 80%. The separator may be made from an inert material, such as a plastic material. Plastic material may include PVDF (polyvinylidiene difluoride), HDPE (high density polyethylene), PP (polypropylene), or PTFE (polytetrafluoroethylene). The separator may also be made of an ion conducting material. Ion conducting materials may include ion exchange materials or membranes, such as sulfonated polystyrene, cation ion exchange sulfonated tetrafluoroethylene materials sold under the trade name of Nafion, as well as hydrocarbon based cation ion exchange materials sold under the trade names of Selemion, Flemion, Neosepta, and the like.

The use of the thin flow channel in this electrochemical cell design may allow for an alternative method for controlling a bulk flow of the solvent and salt into the cell 2800 which may not be possible when using just a single separator between the anolyte and catholyte regions and feeding in the required solvent into the anolyte and catholyte regions separately. The use of porous separators may allow a non-uniform bulk flow distribution from the anolyte to catholyte region, or vice versa, because of pressure differentials between the anolyte and catholyte region flow loops. The electrochemical cell 2800 may be employed to prevent or minimize any unwanted potential bulk flow from the anolyte to catholyte and vice versa.

The electrochemical cell catholyte loop may include a pumped recirculating catholyte solution where carbon dioxide is dissolved into the ACN-TBABr solution and the carbon dioxide may be reduced on a high surface area cathode structure. The high surface cathode structure may incorporate a cathode current distributor. Cathode materials include transition group metals and alloys, such as stainless steel 316 or nickel as examples. The oxalate formed at the cathode may then overflow the catholyte disengager as an ACN solvent containing $TBA_2$Oxalate and any excess or unreacted TBABr. The catholyte product may then be processed in the next unit operation where the oxalate is separated as oxalic acid from the TBABr.

The electrochemical cell anolyte loop may include a pumped recirculating anolyte solution where the dissolved bromide ion in the ACN-TBABr solution may be oxidized at the high surface area anode structure to bromine ($Br_2$). The formed bromine may react with any excess TBABr, such that the bromide ion may couple with the formed bromine to form a tribromide complex, such as $TBABr_3$. The high surface anode structure may incorporate an anode current distributor. Anode materials include carbon materials such as carbon and graphite, which may be in the form of felts, needled felts, or woven forms. These carbon based materials may have catalysts impregnated into and onto the surfaces of the high surface area carbon structure includes platinum group metals and their oxides, mixtures, and alloys, such as gold, platinum, ruthenium dioxide, iridium oxide, and the like that preferably may be chemically resistant to the anode bromine formation chemistry and may help to promote or catalyze the oxidation of bromide to bromine. Other suitable anode materials may be valve metals, such as titanium, niobium, and tantalum having an electrocatalyst surface coating of the various precious metal group metals and their oxides, mixtures, and their alloys. The $TBABr_3$ formed at the anode may then overflow the anolyte disengager as an ACN solvent containing $TBABr_3$ and any excess or unreacted TBABr. The anolyte product may then be processed in the next unit operation where the $TBABr_3$ may be reacted with organics to form brominated hydrocarbons, or reacted with hydrogen to form HBr, which may be used to convert oxalate to oxalic acid.

Figure 29:
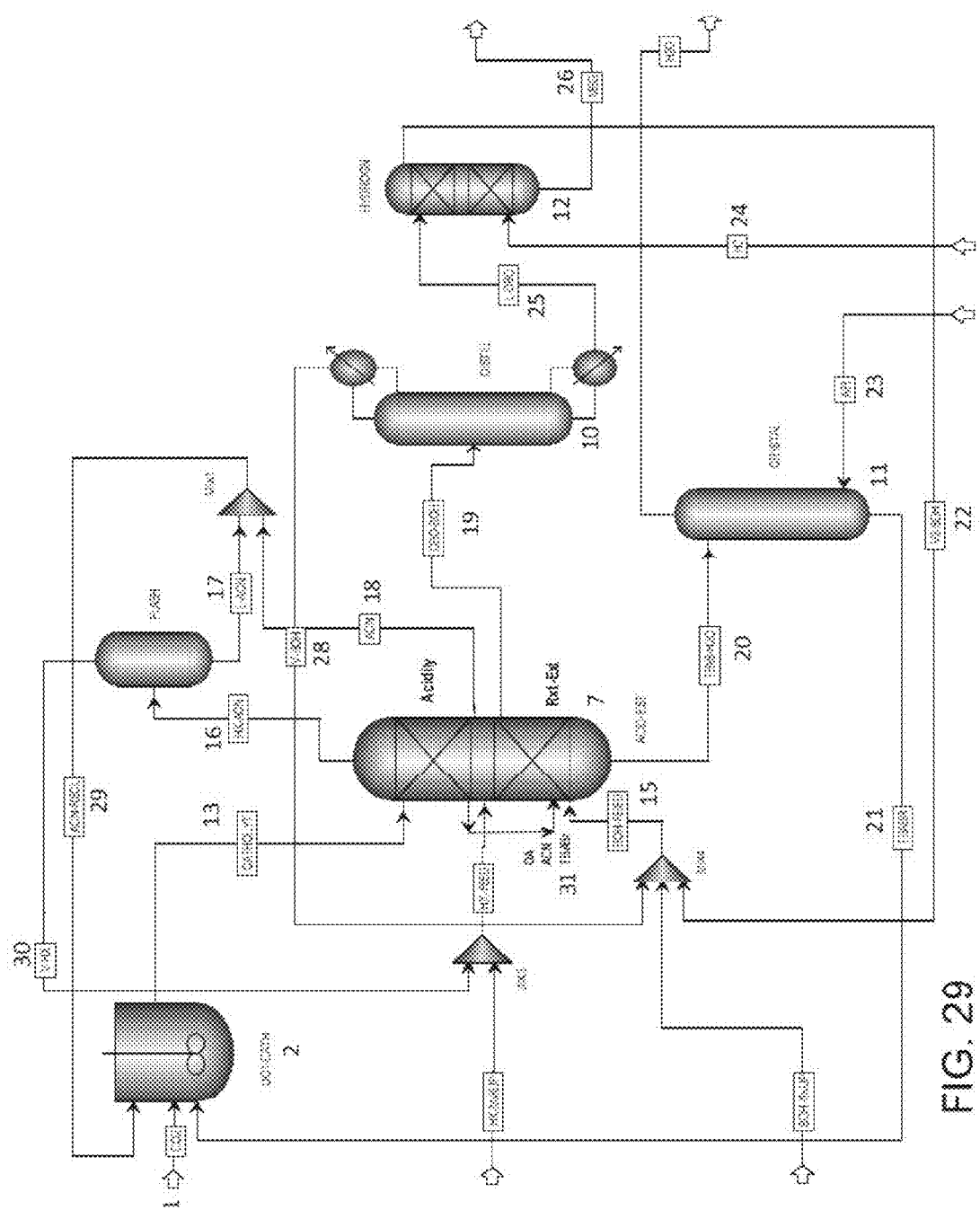
FIG. 29 is a schematic illustrating an integrated acidification-esterification-hydrogenation system.
Figure 30:
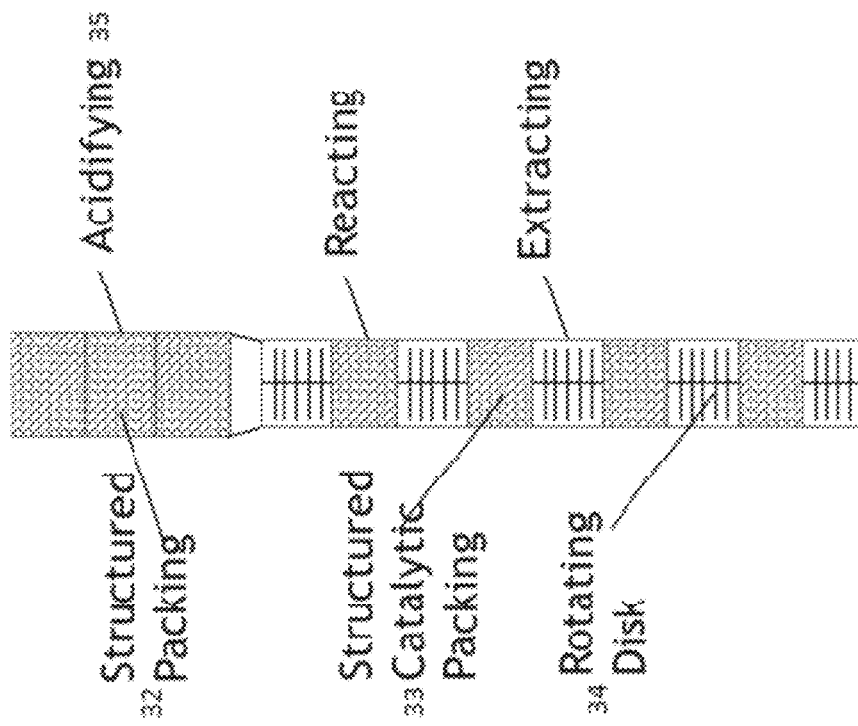
FIG. 30 is a schematic illustrating an integrated acidification-esterification-hydrogenation system is shown.

Referring to FIGS. 29 and 30, an integrated acidification-esterification-hydrogenation system is shown. Carbon dioxide, recycled acetonitrile (ACN) and tetrabutylammonium bromide (TBABr) or tetraalkylammonium halide (TBAX) may be fed into a catholyte region of an electrochemical cell 2, such as described above, where carbon dioxide 1 is electrochemically reduced to form tetra-butyl-ammonium oxalate (($TBA)_2$ oxalate, TBAO) or another oxalate salt. An ACN solution, or other aprotic solvent solution, of TBABr (TBAX) and TBAO from the cathode compartment of the electrochemical cell (i.e., stream CATHOLYT 13) is withdrawn and fed into a reactive extraction column 7. A halide or trihalide anion anolyte stream (not shown) may be withdrawn from the anode compartment of the electrochemical cell 2, or electrochemical cell 2 may comprise a hydrogen oxidizing anode as described above.

The reactive extraction column 7 comprises two sections ("Acidify" and "Rxt-Ext" as indicated in FIG. 29). The column performs three functions: acidification, esterification, and extraction. See FIG. 30 for an illustration of the column 7. As shown in FIG. 30, the upper part of the column is packed with structured packing 32, and it performs acidification of TBAO into oxalic acid (OA) using hydrogen halide vapor, HX, which flows in from the lower part of the Acidify section 35 of the column while the catholyte stream is fed from the top of the column through a liquid distributor to assure uniform distribution of the liquid. Pump-around can be applied from the bottom of this acidifying section to the top of the column to recycle fluids internally, as needed, to ensure complete reaction of TBAO. This section of the column has in-situ energy integration where the heat released by the acidification reaction is used to vaporize the ACN without using any heat transfer fluid or heat exchanger. ACN and unreacted HX 16 vents at the top of the column. After a two phase FLASH, HX 30 is returned to the Acidify 35 section of the column, ACN 18 in the liquid stream is merged with another ACN 17 stream to recycle 29 back to the cathode compartment of the cell 2.

The OA produced flows down with ACN to the lower section of the column 7 for esterification with alcohol, such as 1-butabol (BOH). The alcohol 15 is fed from the bottom of the column. As seen in FIG. 30, this section of the column does esterification and extraction simultaneously. The "Rxt-Ext" section of the column consists of alternative zones of packed solid catalytic bed 33 (with Amberlyst 15, 35 or Zeolite Y) and unpacked rotating disks 34 for extraction. OA and BOH react to produce DBO and $H_2O$. As the products are formed, extraction action takes place, which means that water continuously moves downwards with TBABr that has a favorable partitioning into aqueous phase while DBO, unreacted BOH and other trace organic species move up due to their lighter densities than that of water.

The side-drain feeding of OA+ACN+TBABr to RXT-EXT section 31 goes to the bottom of the reactive zone of the column for concurrent feeding of BOH with OA, which enhances the extraction efficiency of the system as well as the reaction efficiency due to the counter current flow of organic species and water. The downward flow of produced water concentrates BOH in organic phase that is moving up, which speeds up the esterification reaction. The side-drain feeding of OA+ACN+TBABr to RXT-EXT 31 section can also be split into more than one feeding points to optimize the column performance.

As shown in FIG. 29, the bottom stream of the column is TBABr+H2O 20, which is fed into the top of a spray-drying crystallization tower 11 through a liquid distributor with fine orifices. Hot air 23 is entering from the bottom of the tower to evaporate water. The pelleted crystal form of TBABr or TBAX 21 is then recycled back to the cathode compartment of electrochemical cell 2.

The intermediate product DBO 19 plus unreacted BOH 19 exits the upper end of the RXT-EXT section of the ACID-EST column, and enters DISTILL column 10. In this DISTILL column 10, BOH is vaporized and recycled back 28 to the Esterification section (Rxt-Ext section) of the ACID-EST column 7, while the DBO product 25 leaves at the bottom of the DISTILL column 10 and then feeds into a fixed bed reactive distillation column HYDROGN 12 for hydrogenation. This may be a reactive column that is packed with solid Cu—Cr-oxide catalyst, compressed hydrogen 24 at 20 to 50 atm entering from the bottom while DBO is fed from the top. The column has an optimum temperature profile. Product MEG 26 at fiber grade purity of 99.9% exits from the bottom and regenerated BOH 22 is recycled back to the feeding stage of RXT-EXT section of the ACID-EST column 7.

It is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for producing oxalic acid in an electrochemical cell, the electrochemical cell including a first region having a cathode and a second region having an anode, the method comprising the steps of:
    contacting the first region with a catholyte comprising carbon dioxide, an electrolyte and an aprotic solvent;
    contacting the second region with an anolyte, the anolyte comprising hydrogen, the electrolyte and the aprotic solvent;
    receiving the hydrogen in a gas stream at the second region; and
    applying an electrical potential between the anode and the cathode sufficient to produce oxalic acid recoverable from the second region.

2. The method according to claim 1, wherein the aprotic solvent includes at least one of propylene carbonate, ethylene carbonate, dimethyl carbonate, diethyl carbonate, dimethylsulfoxide, dimethylformamide, acetonitrile, acetone, tetrahydrofuran, N,N-dimethylacetamide, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, alkanes, cycloalkanes, perfluorocarbons, linear carbonates, aromatics, benzene, toluene, aromatic derivatives, dichloromethane, chloroform, ethers, chlorobenzene, polyols, glymes, diglymes, triglymes, tetraglymes, alcohols, alkenes, trifluorotoluene, anisole, m-cresol, and ionic liquids to include those containing cations: 1,3 dialkyimidazolium, N,N dialkylpyrrolidinium, and 1-alkyl-2,3-dimethylimidazolium, hexafluorophosphate, tetrafluoroborate, bis(trifluoromethanesulfonyl)imide, perfluoroalkylphosphate, or halide ions.

3. The method according to claim 1, wherein the cathode includes at least one of Al, Au, Ag, Bi, C, Cd, Co, Cr, Cu, $Cu_2O$, Cu, Fe, Ga, Hg, In, Mo, Nb, Ni, $NiCo_2O_4$, Ni—Fe, Pb, Pd Pt, Rh, Sn, Ti, V, W, Zn, stainless steel, austenitic steel, ferritic steel, duplex steel, martensitic steel, Nichrome, elgiloy Hastelloy, Hastelloy 276, Hastelloy C, metal carbides or alloys thereof.

4. The method according to claim 3, wherein said cathode includes nickel or a nickel alloy.

5. The method according to claim 1, wherein the electrolyte is at least one of MX, ionic liquids, cetyl trimethylammonium bromide (CTAB), hexadecyltributyl phosphonium bromide, or tricaprylmethylammonium chloride (Starks' catalyst), wherein M is Li+, Na+, K+, Ca++, Ba++, Sr++, Mg++, or a R1R2R3R4N+X− wherein each of R1-4 is independently selected from the group consisting of alkyl, branched alkyl, cyclo alkyl, and aryl, tetraalkyl ammonium, tetramethylammonium, tetraethylammonium, tetrabutylammonium, tetraphenylphosphonium, tetrabutylphosphonium, tetraethylphosphonium, tetrahexylammonium, tetraoctylammonium, methyl tributylammonium, butyltrimethylammonium, 1-n-butyl-3-methylimidazolium, 1-ethyl-3-methylimidazolium, 1-ethyl-1-methylpyrrolidinium, di-n-decyldimethylammonium, choline, and ammonium, X is F, Cl, Br, I, $BF_4$, $PF_6$, $ClO_4$, or an anion and mixtures thereof.

6. The method according to claim 1, further comprising a separator between the first region and the second region, the separator includes one or more of polymeric porous materials, inorganic filtration materials, perfluorinated ionomers, combination hybrid organic-inorganic organic membranes, hydrocarbon based membranes and solid state ion conductors.

7. The method according to claim 1, further comprising: extracting an oxalic acid solution from the second region.

8. The method according to claim 7, further comprising: receiving the oxalic acid solution at one of a chromatography device, a nano-filtration device, a solid sorbent amine column or liquid-liquid extractor to produce oxalic acid.

9. The method according to claim 8, further comprising: receiving an alcohol at an esterification device; and receiving the oxalic acid at the esterification device wherein the alcohol and the oxalic acid react to produce a dialkyl oxalate.

10. The method according to claim 9, wherein the alcohol and the oxalic acid react to produce a dialkyl oxalate in a reactive distillation column.

11. The method according to claim 9, further comprising: receiving the dialkyl oxalate at a hydrogenation device wherein a dialkyl oxalate reduction product is produced.

12. The method according to claim 8, further comprising; receiving the oxalic acid at a hydrogenation device wherein an oxalic acid reduction product is produced.

* * * * *